US006120994A

United States Patent [19]

Tam

[11] Patent Number: 6,120,994

[45] Date of Patent: Sep. 19, 2000

[54] ANTIOXIDANT RESPONSIVE ELEMENT

[75] Inventor: Shui-Pang Tam, Kingston, Canada

[73] Assignee: Queen's University at Kingston, Ontario, Canada

[21] Appl. No.: 08/862,431

[22] Filed: May 23, 1997

[51] Int. Cl.[7] ............................ C12Q 1/68; C07H 21/04

[52] U.S. Cl. ............................ 435/6; 536/24.1; 435/455; 435/325; 435/375; 435/320.1

[58] Field of Search ................................ 536/23.1, 24.1; 530/350, 358, 361; 435/320.1, 6, 7.21, 91.4, 455, 325, 375

[56] References Cited

U.S. PATENT DOCUMENTS 5,378,822 1/1995 Bradfield et al. ...................... 536/23.5
5,580,722 12/1996 Foulkes et al. ............................ 435/6

FOREIGN PATENT DOCUMENTS 2159532 3/1997 Canada .

OTHER PUBLICATIONS

Torrance, H. et al. Sequence–specific binidng of Ku Autoantigen . . . J. Biol. Chem. 273 (33) 20810–20819, Aug. 1998.

Paranjape, S. et. al. Role of chromatin structure in the regulation . . . Annu. Rev. Biochem. 63: 265–297, Jan. 1995.

Sogawa, K. et al., "Location of regulatory elements responsible for drug induction in the rat cytochrome P–450c gene," *Proc. Natl. Acad. Sci. USA 83*:8044–8048 (1986).

Assmann, G. et al., "The Effects of Cigarette Smoking on Serum Levels of HDL Cholesterol and HDL Apolipoprotein A–I," *J. Clin. Chem. Clin. Biochem. 22*:397–402 (1984).

Azrolan, N. et al., "Dietary Fat Elevates Hepatic ApoA–I Production by Increasing the Fraction of Apolipoprotein A–I mRNA in the Translating Pool," *J. Biol. Chem. 270*(*34*):19833–19838 (1995).

Bartalena, L. et al., "Effects of Interleukin–6 on the Expression of Thyroid Hormone–Binding Protein Genes in Cultured Human Hepatoblastoma–Derived (Hep G2) Cells," *Molec. Endocrinol. 6*(*6*):935–942 (1992).

Benoist, C. and Chambon, P., "In vivo sequence requirements of the SV40 early promoter region," *Nature 290*:304–310 (1981).

Bollen, A.P. and Stauver, M., "DNA Transformation Efficiency of Various Bacterial and Yeast Host–Vector Systems," *J. Clin. Hematol. Oncol. 10*(*2&3*):39–48 (1980).

Breslow, J.L. et al., "Isolation and characterization of cDNA clones for human apolipoprotein A–I," *Proc. Natl. Acad. Sci. USA 79*:6861–6865 (1982).

Broach, J.R., "The Yeast Plasmid 2$\mu$ Circle," *Cell 28*:203–204 (1982).

Bus, J.S. and Gibson, J.E., "Paraquat: Model for Oxidant–Initiated Toxicity," *Environ. Health Persp. 55*:37–46 (1984).

Chater, K.F. et al., "Streptomyces ØC31–Like Phages: Cloning Vectors, Genome Changes and Host Range," Sixth Int. Symp. on Actinomycetes Biology, Debrecen, Hungary, Aug. 26–30, 1985, Szabó, G. et al., eds., Akademiai Kiado, pub., Budapest, Hungary, pp. 45–53 (1987).

Chomczynski, P. and Sacchi, N., "Single–Step Method of RNA Isolation by Acid Guanidinium Thiocyanate–Phenol–Chloroform Extraction," *Anal. Biochem. 162*:156–159 (1987).

Colbère–Garapin, F. et al., "A New Dominant Hybrid Selective Marker for Higher Eukaryotic Cells," *J. Mol. Biol. 150*:1–14 (1981).

Cowan, D.B. et al., "Identification of Oxygen Responsive Elements in the 5'–Flanking Region of the Human Glutathione Peroxidase Gene," *J. Biol. Chem. 268*(*36*):26904–26910 (1993).

Dai, P.–h. et al., "Binding of nuclear proteins to the enhancer elements of the rat apolipoprotein A–I gene," *Eur. J. Biochem. 190*:305–310 (1990).

DeGray, J.A. et al., "Reduction of Paraquat and Related Bipyridylium Compounds to Free Radical Metabolites by Rat Hepatocytes," *Arch. Biochem. Biophys. 289*(*1*):145–152 (1991).

De Wet, J.R. et al., "Chromogenic Immunodetection of Human Serum Albumin and α–L–Fucosidase Clones in a Human Hepatoma cDNA Expression Library," *DNA 3*(*6*):437–447 (1984).

Duby, A.D. et al., "Hybridization with Radioactive Probes," in: *Short Protocols in Molecular Biology*, 2nd Ed., Ausubel, F.M. et al., eds., John Wiley & Sons, Inc., pub., New York, N.Y., pp. 6.6–6.10 (1992).

Esterbauer, H. et al., "Continuous Monitoring of In Vitro Oxidation of Human Low Density Lipoprotein," *Free Rad. Res. Comms. 6*(*1*):67–75 (1989).

Favreau, L.V. and Pickett, C.B., "Transcriptional Regulation of the Rat AND(P)H:Quinone Reductase Gene: Identification of Regulatory Elements Controlling Basal Level Expression and Inducible Expression by Planar Aromatic Compounds and Phenolic Antioxidants," *J. Biol Chem. 266*(*7*):4556–4561 (1991).

Friling, R.S. et al., "Xenobiotic–inducible expression of murine glutathione S–transferase Ya subunit gene is controlled by an electrophile–responsive element," *Proc. Natl. Acad. Sci. USA 87*:6258–6262 (1990).

Glick, B.R. and Whitney, G.K., "Factors affecting the expression of foreign proteins in *Escherichia coli*," *J. Indust. Microbiol. 1*:277–282 (1987).

(List continued on next page.)

*Primary Examiner*—David Guzo
*Assistant Examiner*—Jon Shuman
*Attorney, Agent, or Firm*—Sterne, Kessler, Goldstein & Fox P.L.L.C.

[57] ABSTRACT

The present invention relates, in general, to antioxidant responsive elements (AREs). In particular, the present invention relates to a DNA construct comprising an ARE having the DNA sequence 5'-RGR AC NNN GCT-3' (SEQ ID NO: 1) operably linked to a heterologous protein coding sequence; cells and non-human organisms comprising the DNA construct; a method of screening for a compound that increases transcription of an MRNA regulated by an antioxidant responsive element; and a purified compound that binds to an antioxidant responsive element.

8 Claims, 14 Drawing Sheets

OTHER PUBLICATIONS

Go, M.F. et al., "Regulation of Intestinal and Hepatic Apoprotein Synthesis after Chronic Fat and Cholesterol Feeding," *J. Clin. Invest. 81*:1615–1620 (1988).

Gorman, C.M. et al., "Recombinant Genomes Which Express Chloramphenicol Acetyltransferase in Mammalian Cells," *Mol. Cell. Biol. 2*(*9*):1044–1051 (1982).

Haffner, S.M. et al., "Epidemiological Correlates of High Density Lipoprotein Subfractions, Apolipoproteins A–I, A–II, and D, and Lecithin Cholesterol Acyltransferase: Effects of Smoking, Alcohol, and Adiposity," *Arteriosclerosis 5*:169–177 (1985).

Hamer, D.H. and Walling, M., "Regulation In Vivo of a Cloned Mammalian Gene: Cadmium Induces the Transcription of a Mouse Metallothionein Gene in SV40 Vectors," *J. Mol. Appl. Genet. 1*:273–288 (1982).

Hayek, T. et al., "Dietary Fat Increases High Density Lipoprotein (HDL) Levels Both by Increasing the Transport Rates and Decreasing the Fractional Catabolic Rates of HDL Cholesterol Ester and Apolipoprotein (Apo) A–I: Presentation of a New Animal Model and Mechanistic Studies in Human Apo A–I Transgenic and Control Mice," *J. Clin. Invest. 91*:1665–1671 (1993).

Januzzi, J.L. et al., "Characterization of the Mouse Apolipoprotein Apoa–1/Apoc–3 Gene Locus: Genomic, mRNA, and Protein Sequences with Comparisons to Other Species," *Genomics 14*:1081–1088 (1992).

Jasny, B.R., "Insect Viruses Invade Biotechnology," *Science 238*:1653 (1987).

Jeenah, M. et al., "G to A Substitution in the Promoter Region of the Apolipoprotein AI Gene is Associated With Elevated Serum Apolipoprotein AI and High Density Lipoprotein Cholesterol Concentrations," *Mol. Biol. Med. 7*:233–241 (1990).

Jimenez, A. and Davies, J., "Expression of a transposable antibiotic resistance element in Saccharomyces," *Nature 287*:869–871 (1980).

Johnston, S.A. and Hopper, J.E., "Isolation of the yeast regulatory gne GAL4 and analysis of its dosage effects on the galactose/melibiose regulon," *Proc. Natl. Acad. Sci. USA 79*:6971–6975 (1982).

Karathanasis, S.K. et al., "Linkage of human apolipoproteins A–I and C–III genes," *Nature 304*:371–373 (1983).

Klimov, A.N. et al., "Protective effect of high density lipoproteins, their subfractions and lecithin–cholesterol–acyltransferases on the peroxidation modification of low density lipoproteins," *Biokhimiia 54*(*1*):118–123 (1989), English language abstract.

Laemmli, U.K., "Cleavage of Structural Proteins during the Assembly of the Head of Bacteriophage T4," *Nature 227*:680–685 (1970).

Li, Y. and Jaiswal, A.K., "Regulation of Human AND(P)H:Quinone Oxidoreductase Gene: Role of Ap1 Binding Site Contained Within Human Antioxidant Response Element," *J. Biol. Chem. 267*(*21*):15097–15104 (1992).

Lin–Lee, Y.–C. et al., "Role of thyroid hormone in the expression of apolipoprotein A–IV and C–III genes in rat liver," *J. Lipid Res. 34*:249–259 (1993).

Maître, B. et al., "Effects of inhibition of catalase and superoxide dismutase activity on antioxidant enzyme mRNA levels," *Am. J. Physiol. 265*:L636–L643 (1993).

McKnight, S.L., "Functional Relationship between Transcriptional Control Signals of the Thymidine Kinase Gene of Herpes Simplex Virus," *Cell 31*:355–365 (1982).

Michaelis, L. and Hill, E.S., "The Viologen Indicators," *J. Gen. Physiol. 16*:859–873 (1933).

Michaelis, L. and Hill, E.S., "Potentiometric Studies on Semiquinones," *J. Am. Chem. Soc. 55*(*4*):1481–1494 (1933).

Miller, D.W. et al., "An Insect Baculovirus Host–Vector System for High–Level Expression of Foreign Genes," *Genet. Eng. 8*:277–298 (1986).

Morrison, H.G. and Desrosiers, R.C., "A PCR–Based Strategy for Extensive Mutagenesis of a Target DNA Sequence," *BioTechniques 14*(*3*):454–457 (1993).

Nguyen, T. and Pickett, C.B., "Regulation of Rat Glutathione S–Transferase Ya Subunit Gene Expression: DNA–Protein Interaction at the Antioxidant Responsive Element," *J. Biol. Chem. 267*(*19*):13535–13539 (1992).

Okayama, H. and Berg, P., "A cDNA Cloning Vector That Permits Expression of cDNA Inserts in Mammalian Cells," *Mol. Cell. Biol. 3*(*2*):280–289 (1983).

Pagnani, F. et al., "Human apolipoprotein A–I gene promoter polymorphism: association with hyperalphalipoproteinemia," *J. Lipid Res. 31*:1371–1377 (1990).

Pan, T.–c. et al., "Rabbit apolipoprotein A–I mRNA and gene: Evidence that rabbit apolipoprotein A–I is synthesized in the intestine but not in the liver," *Eur. J. Biochem. 170*:99–104 (1987).

Papazafiri, P. et al., "Promoter Elements and Factors Involved in Hepatic Transcription of the Human ApoA–I Gene Positive and Negative Regulators Bind to Overlapping Sites," *J. Biol. Chem. 266*(*9*):5790–5797 (1991).

Pryor, W.A. et al., "Electron–Spin Resonance Study of Mainstream and Sidestream Cigarette Smoke: Nature of the Free Radicals in Gas–Phase Smoke and in Cigarette Tar," *Env. Health Persp. 47*:345–355 (1983).

Ross, R., "The Pathogenesis of Atherosclerosis—An Update," *New Engl. J. Med. 314*(*8*):488–500 (1986).

Rushmore, T.H. et al., "The Antioxidant Responsive Element: Activation by Oxidative Stress and Identification of the DNA Consensus Sequence Required for Functional Activity," *J. Biol. Chem. 266*(*18*):11623–11639 (1991).

Sambrook, J. et al., "Plasmid Vectors," in: *Molecular Cloning: A Laboratory Manual,* $2^{nd}$ Ed., Cold Spring Harbor Laboratory Press, Cold Spring Harbor, N.Y., pp. 1.12–1.20 (1989).

Sastry, K.N. et al., "Different cis–Acting DNA Elements Control Expression of the Human Apolipoprotein AI Gene in Different Cell Types," *Mol. Cell. Biol. 8*(*2*):605–614 (1988).

Sigurdsson, G., Jr., et al., "Interaction Between a Polymorphism of the Apo A–I Promoter Region and Smoking Determines Plasma Levels of HDL and Apo A–I," *Arteriosclerosis and Thrombosis 12*:1017–1022 (1992).

Silver, P.A. et al., "Amino terminus of the yeast GAL4 gene product is sufficient for nuclear localization," *Proc. Natl. Acad. Sci. USA 81*:5951–5955 (1984).

Smith, J.D. et al., "Polymorphism in the Human Apolipoprotein A–I Gene Promoter Region: Association of the Minor Allele with Decreased Production Rate In vivo and Promoter Activity in Vitro," *J. Clin. Invest. 89*:1796–1800 (1992).

Sorci–Thomas, M. et al., "Apolipoprotein (Apo) A–I Production and mRNA Abundance Explain Plasma ApoA–I and High Density Lipoprotein Differences between Two Nonhuman Primate Species with High and Low Susceptibilities to Diet–induced Hypercholesterolemia," *J. Biol. Chem. 263*(*11*):5183–5189 (1988).

Sorci–Thomas, M. and Kearns, M.W., "Transcriptional Regulation of the Apolipoprotein A–I Gene: Species–Specific Expression Correlates With Rates of Gene Transcription," *J. Biol. Chem. 266*(*27*):18045–18050 (1991).

Sorci–Thomas, M. and Kearns, M.W., "Species–specific polymorphism in the promoter of the apolipoprotein A–I gene: restoration of human transcriptional efficiency by substitution at positions—189, —144 and —48 bp," *Biochim. Biophys. Acta 1256*:387–395 (1995).

Srivastava, R.A.K. et al., "Dietary fatty acids and dietary cholesterol differ in their effect on the in vivo regulation of apolipoprotein A–I and A–II gene expression in inbred strains of mice," *Biochim. Biophys. Acta 1125*:251–261 (1992).

Strobi, W. et al., "Role of Thyroid Hormones in Apolipoprotein A–I Gene Expression in Rat Liver," *J. Clin. Invest. 85*:659–667 (1990).

Thomsen, D.R. et al., "Promoter–regulatory region of the major immediate early gene of human cytomegalovirus," *Proc. Natl. Acad. Sci. USA 81*:659–663 (1984).

Trieu, V.N. et al., "Sequences and expression of the porcine apolipoprotein A–I and C–III mRNAs," *Gene 123*:173–179 (1993).

Trieu, V.N. et al., "Sequence of the porcine apoA–I gene," *Gene 134*:267–270 (1993).

Tuteja, R. et al., "Transcription efficiency of human apolipoprotein A–I promoter varies with naturally occurring A to G transition," *FEBS Letts. 304*(*1*):98–101 (1992).

Ward, J.M. et al., "Construction and characterization of a series of multi–copy promoter–probe plasmid vectors for Streptomyces using the aminoglycoside phosphotransferase gene from Tn5 as indicator," *Mol. Gen. Genet. 203*:468–478 (1986).

Widom, R.L. et al., "Synergistic Interactions between Transcription Factors Control Expression of the Apolipoprotein AI Gene in Liver Cells," *Mol. Cell. Biol. 11*(*2*):677–687 (1991).

Wilhelmsson, C. et al., "Smoking and Myocardial Infarction," *Lancet 7904*(*1*):415–419 (1975).

Wu, C. et al., "Purification and Properties of Drosophila Heat Shock Activator Protein," *Science 238*:1247–1253 (1987).

GenBank Accession No. M20656.

Izaki, K., "Plasmid–determined resistance to heavy metals," *Nippon Saikingaku Zasshi* (*Japanese Journal of Bacteriology*) *33*(*6*):729–742 (1978).

Relative Luciferase Activity

| Control | Gramoxone |
|---|---|
| 2.3±0.1 | 4.5±0.2 * |
| 2.4±0.1 | 4.8±0.1 * |
| 2.1±0.1 | 2.2±0.2 |
| 3.8±0.2 | 7.9±0.2 ** |
| 1.1±0.1 | 1.2±0.2 |
| 4.0±0.2 | 8.2±0.2 ** |
| 1.0±0.1 | 1.0±0.1 |

FIGURE 7

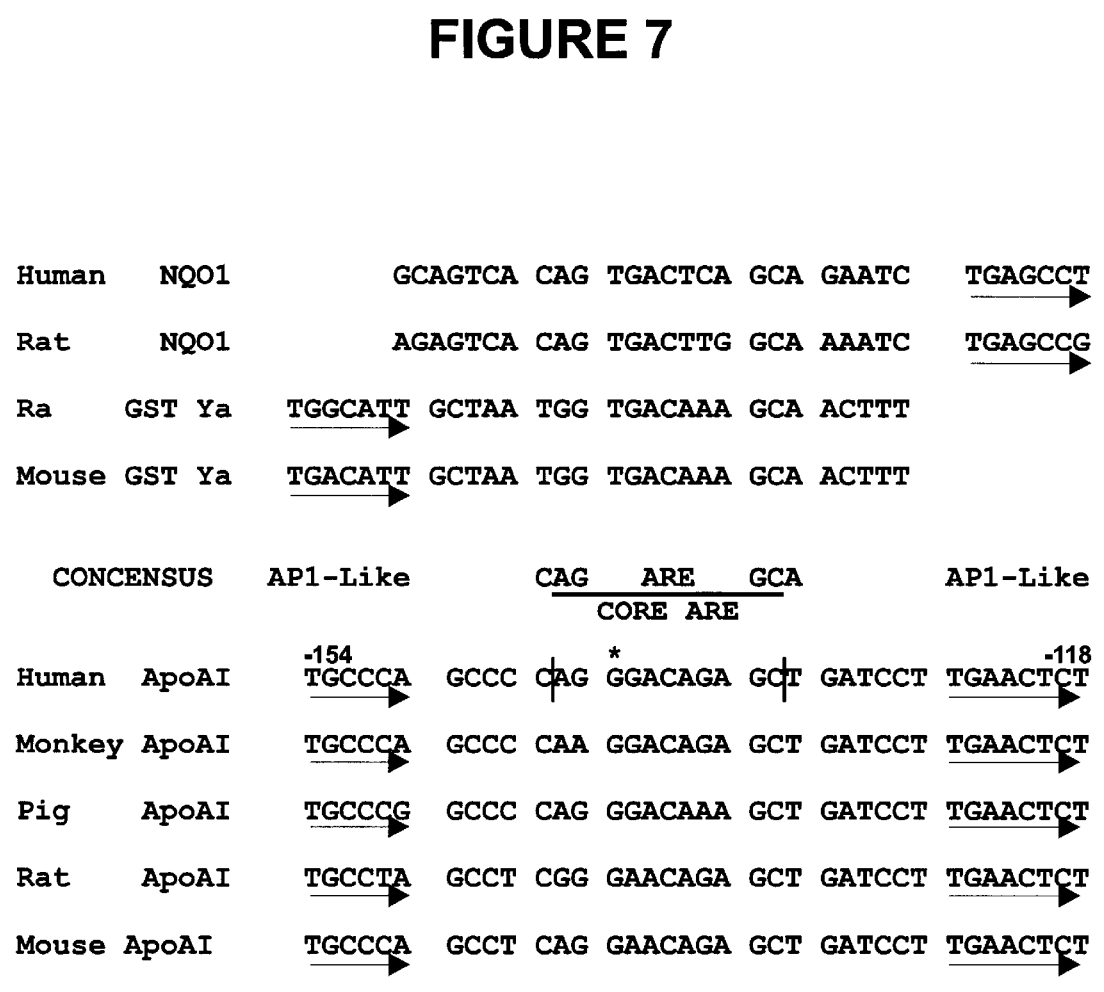

| | | | | | | | | | |
|---|---|---|---|---|---|---|---|---|---|
| Human NQO1 | | | GCAGTCA | CAG | TGACTCA | GCA | GAATC | | TGAGCCT |
| Rat NQO1 | | | AGAGTCA | CAG | TGACTTG | GCA | AAATC | | TGAGCCG |
| Ra GST Ya | TGGCATT | GCTAA | TGG | | TGACAAA | GCA | ACTTT | | |
| Mouse GST Ya | TGACATT | GCTAA | TGG | | TGACAAA | GCA | ACTTT | | |
| CONCENSUS | AP1-Like | | | CAG | ARE (CORE ARE) | GCA | | | AP1-Like |
| Human ApoAI | -154 TGCCCA | GCCC | | CAG | * GGACAGA | GCT | GATCCT | | TGAACTCT -118 |
| Monkey ApoAI | TGCCCA | GCCC | | CAA | GGACAGA | GCT | GATCCT | | TGAACTCT |
| Pig ApoAI | TGCCCG | GCCC | | CAG | GGACAAA | GCT | GATCCT | | TGAACTCT |
| Rat ApoAI | TGCCTA | GCCT | | CGG | GAACAGA | GCT | GATCCT | | TGAACTCT |
| Mouse ApoAI | TGCCCA | GCCT | | CAG | GAACAGA | GCT | GATCCT | | TGAACTCT |

pGL2(apo AI-491)luc pGL2(apo AI-250)luc pGL2(apoAI-250-mutant ARE)luc pGL2(apo AI-mARE)SV40/luc pGL2(GST-ARE)SV40/luc

ANTIOXIDANT RESPONSIVE ELEMENT

BACKGROUND OF THE INVENTION

1. Field of the Invention

The present invention relates, in general, to antioxidant responsive elements (AREs). In particular, the present invention relates to a DNA construct comprising an ARE having the DNA sequence 5'-RGR AC NNN GCT-3' (SEQ ID NO: 1) operably linked to a heterologous protein coding sequence; cells and non-human organisms comprising the DNA construct; a method of screening for a compound that increases transcription of an mRNA regulated by an antioxidant responsive element; and a purified compound (for example, a protein) that binds to an antioxidant responsive element.

2. Related Art

Epidemiological studies have demonstrated that lowering low density lipoprotein-cholesterol (LDL-C) or raising high density lipoprotein-cholesterol (HDL-C) reduces cardiovascular risk (Waters D., and Lesperance, *Am. J. Med.* 91(1B) :10S–17S (1991)). However, among myocardial infarction survivors, greater than one half have normal lipid levels, suggesting that factors other than lipoprotein profiles contribute to the disease process (Wissler, R.W., *Am. J. Med.* 91(1B):3S–9S (1991)). One such factor appears likely to be the oxidation of LDL (Steinberg, D., et al., *N. Engl. J. Med.* 320:915–924 (1989); Parthasarathy, S., and Rankin, S. M., *Prog. in Lipid Res.* 31:127–143 (1992); Esterbauer, H., et al., *Free Radical Res. Commun.* 6:67–75 (1989)). Oxidized LDL has been implicated in the formation of foam cells and thus may play an important role in the etiology of atherosclerosis (Sparrow, C. P., et al., *J. Biol. Chem.* 264:2599–2604 (1989); Ross, R., *N. Engl. J. Med.* 314:488–500 (1986)). In contrast, oxidized HDL is not avidly taken up by macrophages, does not lead to foam cell formation (Parthasarathy, S., et al., *Biochim. Biophys. Acta.* 1044:275–283 (1990)) and may actually inhibit endothelial cell-mediated LDL modification (Parthasarathy, S., et al., *Biochim. Biophys. Acta.* 1044:275–283 (1990); van Hinsbergh, V. W., et al., *Biochim. et Biophys. Acta.* 878:49–64 (1986)). HDL is also capable of protecting against LDL peroxidation in vitro (Parthasarathy, S., et al., *Biochim. Biophys. Acta.* 1044:275–283 (1990); Klimov, A. N., et al., *Biokhimiia* 54:118–123 (1989); Mackness, M. I., et al., *FEBS Lett.* 286:152–154 (1991)). The antioxidative activity of HDL has been demonstrated in vivo (Klimov, A. N., et al., *Atherosclerosis* 100:13–18 (1993)). These properties suggest another protective role for HDL (in addition to its involvement in 'reverse cholesterol transport') in reducing atherosclerotic risk.

Reduced levels of plasma HDL are observed in cigarette smokers (Haffner, S. M., et al., *Arteriosclerosis* 5:169–177 (1985); Assmann, G., et al., *J. Clin. Chem. & Clin. Biochem.* 22:397–402 (1984)). However, the mechanisms responsible for the decrease are not known. During cigarette smoking, the oxidation of polycyclic aromatic hydrocarbons produces free radicals (Pryor, W. A., et al., *Environ. Health Perspect.* 47:345–355 (1983)). The presence of quinone and hydroquinone complexes in the particulate phase of cigarette smoke can result in generation of reactive species such as superoxides and hydrogen peroxide. If a metal catalyst is present, hydroxyl radicals will also form. Consequently, the smoker has a higher free radical burden and a lower HDL level than the nonsmoker and it has been suggested that this may contribute to the smoker's higher risk of developing atherosclerosis (Wilhelmsson, C., et al., *Lancet* 1:415–420 (1975)).

The major protein component of HDL is apolipoprotein (apo) AI, which is believed to promote the process of "reverse cholesterol transport" (Gotto et al., *Methods Enzymol.* 128: 3–41 (1986); Miller et al., *Nature* (London) 314: 109–111 (1985); Glomset, *Adv. Intern. Med.* 25: 91–116 (1980)). In this process, excess cholesterol is liberated from the peripheral tissues and carried, via HDL, to the liver for degradation. In addition, apo AI acts as a cofactor for the enzyme lecithin-cholesterol acyltransferase (LCAT), which is also involved in reverse cholesterol transport (Gotto et al., *Methods Enzymol.* 128: 3–41 (1986); Miller et al., *Nature* (London) 314: 109–111 (1985); Glomset, *Adv. Intern. Med.* 25: 91–116 (1980)). Further evidence that apo AI is a strong negative factor for atherosclerosis comes from experiments in which transgenic mice carrying the human apo AI gene were fed a high fat diet. Here, expression of the apo AI transgene and the resulting high levels of human apo AI in the animals' blood appeared to protect against development of fatty streak lesions (Rubin et al., *Nature* (London) 353: 265–267 (1991)).

The human apo AI gene is located on the long arm of chromosome 11. The DNA sequence of this gene is identified in Karathanasis et al., *Nature* (London) 304: 371–373 (1983); Breslow et al., *Proc. Nat. Acad. Sci. USA* 79: 6861–6865 (1982); and GenBank accession no. M20656. Cis- and trans-acting elements involved in the regulation of transcription of the apo AI gene have been studied by several groups (Sastry et al., *Mol. Cell. Biol.* 8. 605–614 (1988); Widom et al., *Mol. Cell. Biol.* 11: 677–687 (1991); Papazafiri et al., *J. Biol. Chem.* 266: 5790–5797 (1991); Pagani et al., *J. Lipid Res.* 31: 1371–1377 (1990); Smith et al., *J. Clin. Invest.* 89. 1796–1800 (1992); Sigurdsson et al., *Arteriosclerosis and Thrombosis* 12: 1017–1022 (1992); Tuteja et al., *FEBS Letters* 304: 98–101 (1992); Jeenah et al., *Mol. Biol. Med.* 7: 233–241(1990); and Tam et al., Canadian Patent Application No. 2,159,532, filed on Sep. 29, 1995 and laid open for public inspection on Mar. 30, 1997).

A consensus antioxidant responsive element (ARE) with the sequence 5'-RGTGACNNNGC-3' (SEQ ID NO: 33) is present in the rat glutathione S-transferase (GST) Ya subunit gene and the rat NAD(P)H:quinone reductase genes (Rushmore et al., *J. Biol. Chem.* 266:4556–4561 (1991)). Similarly, Li and Jaiswal (*J. Biol. Chem.* 267:15097–15104 (1992)) found within the human NAD(P)H:quinone oxidoreductase gene a sequence corresponding to the ARE described by Rushmore et al., supra.

Although a great deal of work has been done to date on the regulation of expression of the human apo AI gene and on antioxidant responsive elements in other genes, the mechanisms by which various antioxidants influence apo AI expression are heretofore unknown. Given the protection that high plasma apo AI levels provide, it would be extremely desirable to understand how a particular compound could increase apo AI expression. Additionally, novel AREs and convenient methods for screening for compounds which increase transcription of an mRNA regulated by an ARE would also be extremely desirable.

SUMMARY OF THE INVENTION

The invention provides, in general, an antioxidant responsive element.

The invention further provides a DNA construct comprising an antioxidant responsive element (ARE) having a DNA sequence 5'-RGR AC NNN GCT-3' (SEQ ID NO:1) operably linked to a heterologous protein coding sequence.

The invention also provides a recombinant DNA molecule comprising a vector and the above-described DNA construct.

The invention further provides a cell comprising the above-described DNA construct.

The invention also provides a non-human organism comprising the above-described DNA construct.

The invention further provides a method of screening for a compound that increases transcription of an mRNA regulated by an antioxidant responsive element, comprising the steps of:

(a) assaying a first cellular extract for the amount of transcription of the mRNA wherein the mRNA is expressed from a DNA construct, the transcription being in the absence of a candidate compound and the DNA construct comprising:

an antioxidant responsive element (ARE) having a DNA sequence 5'-RGR AG NNN GCT-3' (SEQ ID NO:1) operably linked to a protein coding sequence;

(b) assaying a second cellular extract for the amount of transcription of the mRNA wherein the mRNA is expressed from the DNA construct, the transcription being in the presence of the candidate compound; and (c) comparing the amounts of transcription of the first extract and the second extract, wherein a greater amount of transcription in the second extract as compared to the first extract indicates that the candidate compound increases transcription of the mRNA regulated by the antioxidant responsive element.

The invention also provides a method of screening for a compound that increases transcription of an mRNA regulated by an antioxidant responsive element, comprising the steps of:

(a) assaying a first cellular extract for the amount of protein produced from an mRNA wherein the mRNA is expressed from a DNA construct, the expression being in the absence of a candidate compound and the DNA construct comprising:

an antioxidant responsive element (ARE) having a DNA sequence 5'-RGR AC NNN GCT-3' (SEQ ID NO:1) operably linked to a protein coding sequence;

(b) assaying a second cellular extract for the amount of protein produced from an mRNA wherein the mRNA is expressed from the DNA construct, the transcription being in the presence of the candidate compound; and (c) comparing the amounts of protein of the first extract and the second extract, wherein a greater amount of protein in the second extract as compared to the first extract indicates that the candidate compound increases transcription of the mRNA regulated by the antioxidant responsive element.

The invention also provides a method of identifying a transcription factor that binds to an antioxidant responsive element (ARE) having the DNA sequence 5'-RGR AC NNN GCT-3' (SEQ ID NO:1) comprising:

screening a mixture of cellular components for binding of a transcription factor to the ARE and identifying a transcription factor which binds the ARE.

The invention further provides a purified transcription factor identified using the above-described method.

The invention also provides a compound that increases transcription of an mRNA regulated by an antioxidant responsive element having the DNA sequence 5'-RGR AC NNN GCT-3' (SEQ ID NO:1). In a preferred embodiment, the compound is a protein (or protein complex) that binds to the ARE.

In summary, the invention provides a convenient, efficient and rapid system for screening and identifying compounds that increase transcription of an mRNA regulated by an antioxidant responsive element, for example, apoAI. Thus, the invention additionally provides a method of treating a human being or an animal with such a compound.

Further objects and advantages of the present invention will be clear from the description that follows.

Definitions

In the description that follows, a number of terms used in recombinant DNA (rDNA) technology are extensively utilized. In order to provide a clear and consistent understanding of the specification and claims, including the scope to be given such terms, the following definitions are provided.

Recombinant DNA. Any DNA molecule formed by joining DNA segments from different sources and produced using recombinant DNA technology (aka. molecular genetic engineering).

DNA Segment. A DNA segment, as is generally understood and used herein, refers to a molecule comprising a linear stretch of nucleotides wherein the nucleotides are present in a sequence that can encode, through the genetic code, a molecule comprising a linear sequence of amino acid residues that is referred to as a protein, a protein fragment or a polypeptide.

Gene. A nucleic acid sequence related to a single polypeptide chain or protein, and as used herein includes 5' and 3' untranslated ends. The polypeptide can be encoded by a full-length sequence or any portion of the coding sequence, so long as the functional activity of the protein is retained.

Complementary DNA (cDNA). Recombinant nucleic acid molecules synthesized by reverse transcription of messenger RNA ("mRNA").

Structural Gene. A DNA sequence that is transcribed into mRNA that is then translated into a sequence of amino acids characteristic of a specific polypeptide.

Protein Coding Sequence. A nucleic acid sequence that encodes a protein or polypeptide.

Protein Complex. Two or more proteins bound together by covalent or non-covalent linkage or a protein and another compound (ex. an inducer or drug).

Reporter Gene. A gene encoding a protein that is easily assayed, wherein the assay provides a quantitative measure of the amount of protein (gene product) present. A first example of a useful reporter gene that can be used in a DNA construct according to the invention is the firefly luciferase gene. The protein encoded by this gene catalyzes a reaction that produces light as one of its reaction products. The amount of light emitted can be easily quantitated (*GeneLight*™ *Plasmids Technical Manual*, Promega) and correlates with the amount of luciferase protein present. A second example of a useful reporter gene according to the invention is the *E. coli* lacZ gene, which can be quantitated by a calorimetric assay (*GeneLight*™ *Plasmids Technical Manual*, Promega; *Molecular Cloning: A Laboratory Manual*, second edition, edited by Sambrook, Fritsch, & Maniatis, Cold Spring Harbor Laboratory, 1989)). A third example of a useful reporter gene according to the invention is the chloramphenicol acetyltransferase (CAT) gene. Here too, the reaction products of the CAT enzyme can be conveniently assayed to provide a quantitative measure of the amount of enzyme present (Gorman el al., *Mol. Cell. Biol.* 2: 1044–105 1). Other convenient reporter genes would be known to a person skilled in the art.

Vector. A plasmid, phage, or virus DNA or other DNA sequence into which DNA can be inserted to be cloned. The vector can replicate autonomously in a host cell, and can, in some cases, be further characterized by one or a small number of endonuclease recognition sites at which such DNA sequences can be cut in a determinable fashion and into which other DNA can be inserted. The vector can further comprise a marker suitable for use in the identification of cells transformed with the vector. Markers, for example, are tetracycline resistance, ampicillin resistance and G418 resistance. The words “cloning vehicle” are sometimes used for “vector.”

Expression. Expression is the process by which a structural gene produces a polypeptide. It involves transcription of the gene into mRNA, and the translation of such mRNA into polypeptide(s).

Expression Vector. A vector or vehicle similar to a cloning vector but which is capable of expressing a gene which has been cloned into it, after transformation into a host. The cloned gene is usually placed under the control of (i.e., operably linked to) certain control sequences such as promoter sequences.

Expression control sequences will vary depending on whether the vector is designed to express the operably linked gene in a prokaryotic or eukaryotic host and can additionally comprise transcriptional elements such as enhancer elements, termination sequences, tissue-specificity elements, and/or translational initiation and termination sites.

Nucleic Acid Hybridization. Nucleic acid hybridization depends on the principle that two single-stranded nucleic acid molecules that have complementary base sequences will reform the thermodynamically favored double-stranded structure if they are mixed under the proper conditions. The double-stranded structure will be formed between two complementary single-stranded nucleic acids even if one is immobilized on a nitrocellulose filter. In the Southern hybridization procedure, the latter situation occurs. The DNA of the individual to be tested is digested with a restriction endonuclease, fractionated by agarose gel electrophoresis, converted to the single-stranded form, and transferred to nitrocellulose membrane, making it available for annealing to a hybridization probe. Examples of hybridization conditions can be found in Ausubel, F. M. et al., *Current Protocols in Molecular Biology*, John Wiley & Sons, Inc., New York, N.Y. (1989). In one such example, a nitrocellulose filter is incubated overnight at 68° C. with labeled probe in a solution comprising 50% formamide, high salt (either 5× SSC [20×: 3M NaCl/0.3M trisodium citrate] or 5× SSPE [20×: 3.6M NaCl/0.2M $NaH_2PO_4$/0.02M EDTA, pH 7.7]), 5× Denhardt's solution, 1% SDS, and 100 $\mu$g/ml denatured salmon sperm DNA. This is followed by several washes in 0.2× SSC/0.1% SDS at a temperature selected based on the desired stringency: room temperature (low stringency), 42° C. (moderate stringency) or 68° C. (high stringency). The temperature selected is determined based on the melting temperature (Tm) of the DNA hybrid.

Polyacrylarnide Gel Electrophoresis (PAGE). The most commonly used technique (though not the only one) for achieving a fractionation of polypeptides on the basis of size is polyacrylamide gel electrophoresis. The principle of this method is that polypeptide molecules migrate through the gel as though it were a sieve that retards the movement of the largest molecules to the greatest extent and the movement of the smallest molecules to the least extent. Note that the smaller the polypeptide fragment, the greater the mobility under electrophoresis in the polyacrylamide gel. Both before and during electrophoresis, the polypeptides typically are continuously exposed to the detergent sodium dodecyl sulfate (SDS), under which conditions the polypeptides are denatured. Native gels are run in the absence of SDS. The polypeptides fractionated by polyacrylamide gel electrophoresis can be visualized directly by a staining procedure.

Western Transfer Procedure. The purpose of the western transfer procedure (also referred to as immunoblotting) is to physically transfer polypeptides fractionated by polyacrylamide gel electrophoresis onto a nitrocellulose filter or another appropriate surface, while retaining the relative positions of polypeptides resulting from the fractionation procedure. The blot is then probed with an antibody that specifically binds to the polypeptide(s) of interest.

Purified. A “purified” protein or nucleic acid is a protein or nucleic acid that has been separated from a cellular component. “Purified” proteins or nucleic acids have been purified to a level of purity not found in nature.

Substantially Pure. A “substantially pure” protein or nucleic acid is a protein or nucleic acid preparation that is lacking in essentially all other cellular components.

Induction of expression of a particular coding sequence or gene by a compound. Such induction may occur according to one or more of a number of different mechanisms, as are known to persons skilled in the art:

1. The compound may bind directly to a cis-acting regulatory element (preferably, the cis-acting regulatory element described herein is an ARE) of the gene, causing an increase in transcription of the gene.
2. The compound may bind to a transcription factor (protein or protein complex) that is already present in the cell in an inactive form, thus activating or derepressing it. The derepressed transcription factor may then be able to bind, generally with the compound, to a cis-acting regulatory element of the gene, consequently increasing transcription.
3. The compound may bind an inhibitor of the gene, rendering the inhibitor ineffective. For example, the inhibitor may be bound to a cis-acting repressor element of the gene, and binding of the compound to the inhibitor causes it to be released from the repressor element.
4. The compound may stabilize mRNA transcribed from the gene against degradation by the cellular machinery, thus lengthening its persistence in the cell and increasing the number of times it may be translated to protein.
5. The compound may cause increased synthesis of a transcription factor that positively regulates the gene. This may occur by any of mechanisms 1–4 operating on a second gene that encodes the transcription factor. Increased abundance of the transcription factor results in increased expression of the first gene, on which it acts.

BRIEF DESCRIPTION OF THE FIGS.

FIG. 1. Kinetic studies of apoAI, apoB and apoE mRNA levels in response to gramoxone.

FIG. 2. Time course of transcription rates of the apoAI gene in HepG2 cells cultured in the absence or presence of gramoxone.

FIG. 3. Determination of apoAI mRNA half-lives in the absence or presence of gramoxone.

FIGS. 4A and B. Schematic representations of pGL2-apoAI and pGL2-ARE SV40/luciferase reporter gene plasmids and analysis of luciferase activity on transfected HepG2 cells. FIG. 4A describes the pGL2-apoAI-luciferase chimeric construct series which comprises sequences −491 to +1 and −250 to +1 of the human apoAI proximal promoter region. The pGL2 (apoAI-250 mutant ARE) (SEQ ID NO: 42) comprises a DNA sequence in which point mutations eliminated the apoAI-ARE in the apoAI promoter. The pGL2-ARE SV40/luc series was constructed with synthetic apoAI-ARE (SEQ ID NO: 34), apoAI mutant ARE (SEQ ID NO: 35) and GST-ARE (SEQ ID NO: 36) as described infra. Freshly seeded HepG2 cells were transfected with the reporter plasmid and lacZ as an internal control to normalize for differences in transfection efficiency. Cells were then cultured in the absence or presence of gramoxone (0.1 $\mu$M) for 8 h prior to harvesting. FIG. 4B represents relative luciferase activity in transfected HepG2 cells cultured in the absence (control) or presence of gramoxone. Luciferase activities of the constructs are expressed relative to that of the pGL2 promoter vector. Results are mean ±S.E.M. for five independent experiments carried out in duplicate. * and ** represent significant differences from control, P<0.001 and P<0.01, respectively.

FIGS. 5A and B. Gel mobility shift assay of the apoAI-ARE and GST-ARE, respectively, in response to gramoxone.

FIGS. 6A, B and C. UV cross-linking analysis of the apoAI-ARE and GST-ARE binding nuclear proteins.

FIG. 7. Nucleic acid sequence comparison of antioxidant responsive elements from the human NAD(P)H:quinone oxidoreductase gene (SEQ ID NO: 43) (Li and Jaiswal, *J. Biol. Chem.* 267.15097–15104 (1992)), the rat NAD(P)H:quinone reductase gene (SEQ ID NO: 44) (Rushmore et al., *J. Biol. Chem.* 266:4556–4561 (1991), rat glutathione S-transferase (GST) Ya subunit gene (SEQ ID NO: 45) (Rushmore et al., *J. Biol. Chem.* 266:4556–4561 (1991), the mouse glutathione S-transferase (GST) Ya subunit gene (SEQ ID NO: 46) (Friling et al., *Proc. Natl. Acad. Sci. USA* 87:6258–6262 (1990)), and the human (SEQ ID NO: 47) (Sastry et al., *Mol. Cell. Biol.* 8(2):605–614 (1988)), African green monkey (SEQ ID NO: 48) (Sorci-Thomas and Kearns, *J. Biol. Chem.* 266:18045–18050 (1991)), pig (SEQ ID NO: 49) (Trieu et al., *Gene* 123(2):173–179 (1993) and *Gene* 134(2):267–270), rat (SEQ ID NO: 50) (Dai et al., *Eur. J. Biochem.* 190(2): 305–310 (1990) and Sastry et al., *Mol. Cell. Biol.* 8(2):605–614 (1988)) and mouse (SEQ ID NO: 51) (Stoffel et al., *Biol. Chem.* 373(4): 187–193 (1992) and Januzzi et al., *Genomics* 14:1081–1088 (1992)) apoAI genes.

FIG. 8. pGL2 (apo AI-491)luc is shown (SEQ ID NO: 26).

FIG. 9. pGL2 (apo AI-250)luc is shown (SEQ ID NO: 27).

FIG. 10. pGL2 (apo AI-250-mutant ARE)luc is shown (SEQ ID NO: 28).

FIG. 11. pGL2 (apo AI-ARE)SV40/luc is shown (SEQ ID NO: 29).

FIG. 12. pGL2 (apo AI-mARE)SV40/luc is shown (SEQ ID NO: 30).

FIG. 13. pGL2 (GST-ARE)SV40/luc is shown (SEQ ID NO: 31).

FIG. 14. pGL2 promoter is shown (SEQ ID NO: 32).

DETAILED DESCRIPTION OF THE PREFERRED EMBODIMENTS

Figure 1:
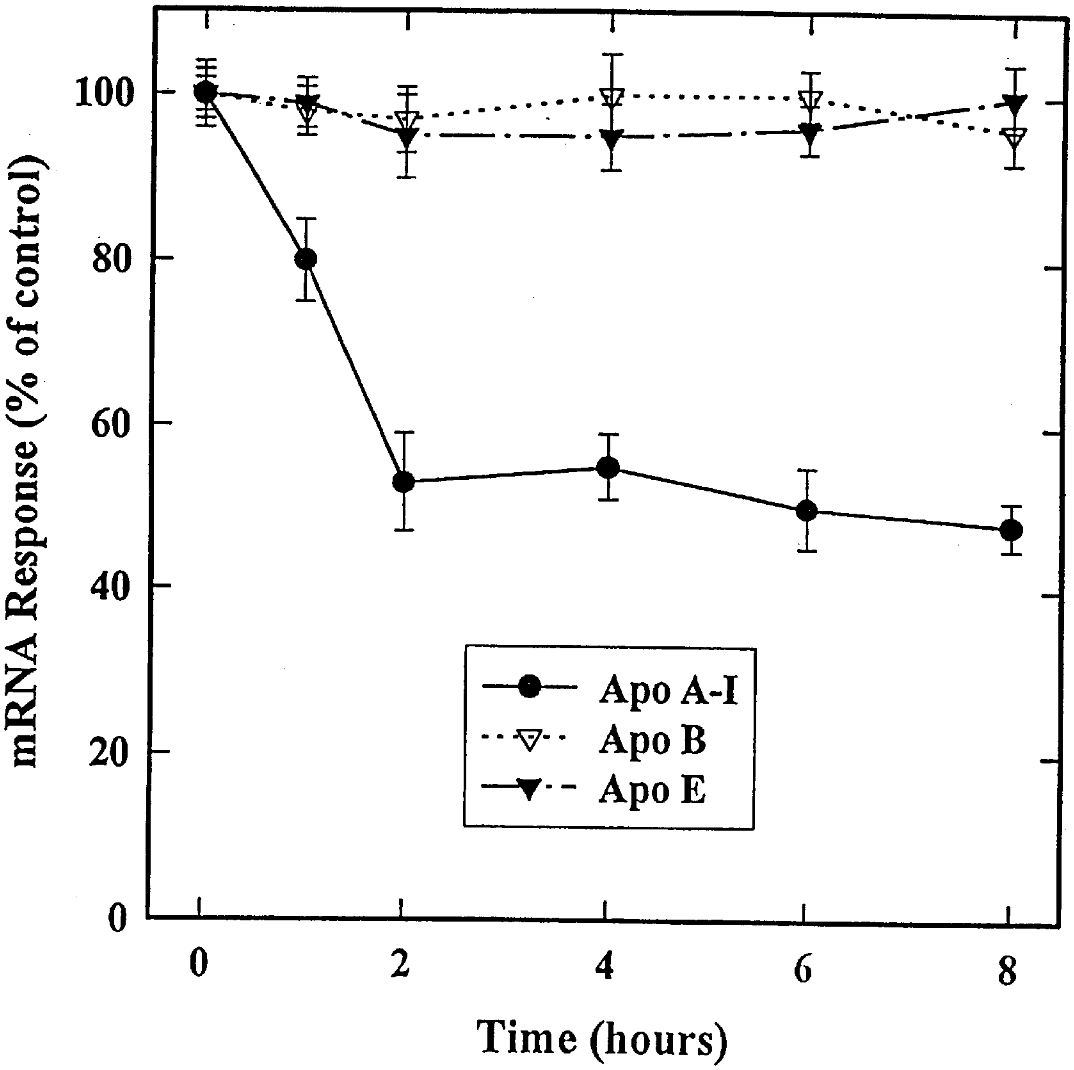

For purposes of clarity of disclosure, and not by way of limitation, the detailed description of the invention is divided into the following subsections:

I. Antioxidant Responsive Elements

II. DNA Constructs, Vectors, Cells and Organisms

III. A Method of Screening for a Compound that Increases Transcription of an mRNA Regulated by an ARE IV. Compounds (Including Proteins) that Bind an ARE I. Antioxidant Responsive Elements In one embodiment, the present invention relates to an antioxidant responsive element (ARE).

The present invention demonstrates herein that oxidative stress does affect the synthesis of apoAI, the major protein constituent of HDL. To induce oxidative stress, the human hepatoma cell line, HepG2, was exposed to gramoxone (also called paraquat and methyl viologen). This compound is a quaternary dipyridyl that is not metabolized but undergoes a one-electron reduction to form a stable free radical (Michaelis, L. and Hill, E. S., *J. Gen. Physiol.* 16:859–873 (1933); Michaelis, L. and Hill, E. S. *J. Am. Chem. Soc.* 55:1481–1494 (1933)). Redox cycling of the free radical decreases the levels of reducing equivalents in the cell and it is the critical biomedical event in gramoxone toxicity (Bus, J. S., and Gibson, J. E., *Environ. Health Perspect* 55:37–46 (1984)). Gramoxone has no other known mechanism of cytotoxicity (DeGray, J. A., et al., *Arch. Biochem. Biophys.* 129:145–152 (1991)).

Exposure of HepG2 cells to gramoxone (0.1 $\mu$M) resulted in a two-fold decrease in apoAI mRNA with no significant change in apoB and apoE mRNA levels. To examine if increased rates of mRNA degradation were responsible for the reduction in apoAI mRNA levels, mRNA half-lives were measured in the presence of actinomycin D with and without gramoxone treatment. These studies revealed a 4-fold increase in the rate of apoAI mRNA degradation in cells exposed to gramoxone. In similarly treated cells, nuclear run-off assays indicated that the transcription rate of the apoAI gene was also increased 2-fold. Consistent with nuclear run-off assays, transient transfection experiments using a series of pGL2-derived luciferase reporter plasmids comprising the human apoAI proximal promoter demonstrated that gramoxone treatment increased apoAI promoter activity 2-fold.

When the apoAI promoter region was examined, an antioxidant response element (ARE) that is responsible for the increase in apoAI transcriptional activity triggered by gramoxone was identified.

Thus, in one embodiment, the present invention relates, in general, to an antioxidant response element. More specifically, the present invention relates to an ARE comprising the DNA sequence 5'-RGR AC NNN GCT-3' (SEQ ID NO:1) or an ARE having all of the functional properties of this ARE (preferably, the complement of which under stringent hybridization conditions hybridizes to SEQ ID NO:1 or any of the herein characterized AREs). In another embodiment, the present invention relates to an ARE comprising a DNA sequence selected from the group consisting of those sequences set forth in Table 1.

TABLE 1

PREFERRED ANTIOXIDANT RESPONSE ELEMENTS

| SEQUENCE | SEQ ID NO |
|---|---|
| 5'-GGG AC NNN GCT-3' | SEQ ID NO:2 |
| 5'-GGG AC AGA GCT-3' | SEQ ID NO:3 |
| 5'-RGG AC NNN GCT-3' | SEQ ID NO:4 |
| 5'-GGR AC NNN GCT-3' | SEQ ID NO:5 |
| 5'-RRGR AC NNN GC-3' | SEQ ID NO:6 |
| 5'-RRGR AC NNN GCT-3' | SEQ ID NO:7 |
| 5'-YRRGR AC NNN GC-3' | SEQ ID NO:8 |
| 5'-YRRGR AC NNN GCT-3' | SEQ ID NO:9 |

TABLE 1-continued

| PREFERRED ANTIOXIDANT RESPONSE ELEMENTS | |
|---|---|
| SEQUENCE | SEQ ID NO |
| 5'-AGGG AC AGAGC-3' | SEQ ID NO:10 |
| 5'-AGGG AC AGAGCT-3' | SEQ ID NO:11 |
| 5'-CAGGG AC AGAGC-3' | SEQ ID NO:12 |
| 5'-CAGGG AC AGAGCT-3' | SEQ ID NO:13 |
| 5'-AGG AC AGAGCT-3' | SEQ ID NO:14 |
| 5'-AAGG AC AGAGC-3' | SEQ ID NO:15 |
| 5'-AAGG AC AGAGCT-3' | SEQ ID NO:16 |
| 5'-CAAGG AC AGAGC-3' | SEQ ID NO:17 |
| 5'-GGG AC AAAGCT-3' | SEQ ID NO:18 |
| 5'-A GGG AC AAAGCT-3' | SEQ ID NO:19 |
| 5'-CA GGG AC AAAGCT-3' | SEQ ID NO:20 |
| 5'-GGA AC AGAGCT-3' | SEQ ID NO:21 |
| 5'-G GGA AC AGAGCT-3' | SEQ ID NO:22 |
| 5'-CG GGA AC AGAGCT-3' | SEQ ID NO:23 |
| 5'-A GGA AC AGAGCT-3' | SEQ ID NO:24 |
| 5'-CA GGA AC AGAGCT-3' | SEQ ID NO:25 |

In one preferred embodiment, the present invention relates to an antioxidant response element consisting essentially of one of the above-described sequences. In another preferred embodiment, the present invention relates to an antioxidant response element consisting of one of the above-described sequences.

One skilled in the art will realize that organisms other than humans will also contain AREs (for example, eukaryotes; more specifically, mammals, rodents, worms (preferably, *C. elegans*), insects (preferably, fruit flies, Drosophila) birds, fish, yeast, and plants; more specifically, gorillas, rhesus monkeys, and chimpanzees). Species-specific polymorphism is known to exist in the promoter region of the human vs. African green monkey apolipoprotein AI gene (Sorci-Thomas and Kearns, *Biochimica et Biophysics Acta* 1256:387–395 (1995); Thomas and Kearns, *J. Biol. Chem.* 254:18045–18060 (1991)). Thus, the invention is intended to include, but not be limited to, ARE nucleic acid molecules isolated from the above-described organisms.

One copy of an antioxidant responsive element which differs from the element described by Rushmore et al., *J. Biol. Chem.* 266:4556–4561 (1991) in that it has a T rather than a G atposition -141 bp, is present in the apoAI promoter between nucleotides −142 to −132 relative to the transcription start site (+1) of the gene. This element is highly conserved across species including human, pig, rabbit, monkey, rat and mouse (See, FIG. 7 for comparison and references; Pan et al., *Eur. J. Biochem.* 170(1-2):99–104 (1 987) (rabbit ApoAI)).

The African green monkey, a species which typically shows a low response to dietary cholesterol, has a higher plasma apoAI concentration and apoAI mRNA abundance than human. Studies carried out by Sorci-Thomas and coworkers (*J. Biol. Chem.* 266:18045–18050 (1991) and *Biochem. Biophys. Acta* 1256: 387–395 (1995)) have indicated that species-specific differences in apoAI expression could be explained by cis-acting factors located within or near the 5' flanking region (−231 to −15 bp).

A G/A substitution at −142 bp of the human apoAI promoter raised the human apoAI promoter activity to approximately 60–65% of the African green monkey promoter. Taken together, these data suggest that the ARE region of the apoAI promoter plays an important role in the transcriptional regulation of the apoAI gene.

II DNA Constructs, Vectors, Cells and Organisms

In another embodiment, the present invention relates to a DNA construct comprising an above-described antioxidant responsive element operably linked to a heterologous protein coding sequence. In a preferred embodiment, the DNA construct is an isolated, recombinant, purified, or substantially pure DNA construct. The ARE is operably linked to the heterologous protein coding sequence when the ARE increases transcription of the heterologous protein coding sequence in vivo in the presence of an appropriate compound (for example, an antioxidant).

Two DNA sequences (such as an ARE and a heterologous protein coding sequence) are said to be operably linked if the nature of the linkage between the two DNA sequences does not (1) result in the introduction of a frame-shift mutation, (2) interfere with the ability of a promoter region sequence to direct the transcription of the heterologous protein coding sequence, or (3) interfere with the ability of the heterologous protein coding sequence to be transcribed by a promoter region sequence. Thus, an ARE would be operably linked to an heterologous protein coding sequence if the ARE were capable of effecting increased transcription of that sequence relative to an appropriate control.

In a preferred embodiment, the above-described DNA construct further comprises a promoter (which does not include an ARE) operably linked to the heterologous protein coding sequence. In another preferred embodiment, the DNA construct further comprises an untranslated region which includes a functional polyadenylation signal operably linked to the heterologous protein coding sequence.

In some embodiments of the invention, the DNA construct includes at least two AREs upstream of the heterologous protein coding sequence. The two AREs can be arranged in a tandem or inverted repeat relative to each other. A spacer region can be interposed between the two copies of the ARE (preferably, the spacer region is about 10 nucleotides long).

In another embodiment, the present invention relates to a recombinant DNA molecule comprising a vector and the above-described ARE or DNA construct.

In another embodiment, the present invention relates to a cell or non-human organism that comprises an above-described ARE or DNA construct.

In the context of this disclosure, the term "heterologous" protein coding sequence is defined as a protein coding sequence wherein the regulatory elements of this protein coding sequence do not naturally include a copy of the ARE.

In one preferred embodiment, the heterologous protein coding sequence refers to a gene encoding a protein that is easily assayed (e.g., a reporter gene), wherein the assay provides a quantitative measure of the amount of protein (gene product) present.

A nucleic acid molecule, such as DNA, is said to be "capable of expressing" a polypeptide (encoded by a protein coding sequence) if it comprises nucleotide sequences which comprise transcriptional and translational regulatory information and such sequences are "operably linked" to nucleotide sequences which encode the polypeptide. The precise nature of the regulatory regions needed for gene sequence expression can vary from organism to organism, but shall in general include a promoter region which, in prokaryotes, comprises both the promoter (which directs the initiation of RNA transcription) as well as DNA sequences which, when transcribed into RNA, will signal protein synthesis initiation. Such regulatory regions will normally include those 5'-non-coding sequences involved with initiation of transcription and translation, such as the TATA box, capping sequence, CAAT sequence, and the like. Additional elements can also be needed for optimal synthesis of the heterologous protein. These elements can include splice signals, as well as transcription promoters, enhancer signal sequences, and termination signals. cDNA expression vectors incorporating such elements include those described by Okayama, *Molec. Cell. Biol.* 3:280 (1983).

The present invention encompasses the expression of the heterologous protein coding sequence operably linked to the ARE in either prokaryotic or eukaryotic cells.

Prokaryotes most frequently are represented by various strains of *E. coli*. However, other microbial strains can also be used, including other bacterial strains. In prokaryotic systems, plasmid vectors that contain replication sites and control sequences derived from a species compatible with the host can be used. Preferred prokaryotic vectors include plasmids such as those capable of replication in *E. coli* (such as, for example, pBR322, ColE1, pSC101, pACYC 184, πVX). Such plasmids are, for example, disclosed in *Molecular Cloning: A Laboratory Manual*, second edition, edited by Sambrook, Fritsch, & Maniatis, Cold Spring Harbor Laboratory, NY 1989; for Bacillus plasmids see, Gryczan, In: *The Molecular Biology of the Bacilli*, Academic Press, NY (1982), pp. 307–329; for Streptomyces plasmids see, Kendall et al., *J. Bacteriol.* 169:4177–4183 (1987)); for Streptomyces bacteriophages see, Chater et al., In: *Sixth International Symposium on Actinomycetales Biology*, Akademiai Kaido, Budapest, Hungary, pp. 45–54 (1986); for Pseudomonas plasmids see, John et al. *Rev. Infect. Dis.* 8:693–704 (1986) and Izaki, *Jpn. J. Bacteriol.* 33:729–742 ((1978). "Plasmids" as used herein encompasses cosmids.

Recognized prokaryotic hosts include bacteria such as *E. coli*, Bacillus, Streptomyces, Pseudomonas, Salmonella, Serratia, and the like. The prokaryotic host must be compatible with the replicon and control sequences in the expression plasmid.

To express the heterologous protein coding sequence in a prokaryotic cell, it is necessary to operably link the heterologous protein coding sequence to a functional prokaryotic promoter. Such promoters can be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pBR325, and the like.

Prokaryotic promoters are reviewed by Glick (*J. Ind. Microbiol.* 1:277–282 (1987)); Cenatiempo (*Biochimie* 68:505–516 (1986)); and Gottesman (*Ann. Rev. Genet.* 18:415–442 (1984)).

Proper expression in a prokaryotic cell also requires the presence of a ribosome binding site upstream of the protein-encoding sequence. Such ribosome binding sites are disclosed, for example, by Gold et al., *Ann. Rev. Microbiol.* 35:365–404 (1981).

Preferred eukaryotic hosts include, for example, yeast, fungi, insect cells, and mammalian cells either in vivo, or in tissue culture. Preferred mammalian cells include hepatic cells (preferably, human hepatoma cell lines Hep3B and HepG2 (Tam, *Atherosclerosis* 91:51–61 (1991); human hepatoma cell lines HH01, HH02, HH09, and HH25 (Roberts et al., *Hepatology* 19(6):1390–9 (1994); See also, Roberts et al., *Biochem. & Biophy. Res. Comm.* 201(2):559–66 (1994)). In the examples described in detail below, DNA constructs according to the invention were introduced into hepatoma cells, in view of the fact that the human apo AI gene is expressed in liver cells. However, it may for some reason be desirable to practice the invention in a non-hepatic cell type, such as, for example, intestinal cells, in which the apo AI gene is also expressed (Gotto et al., *Methods Enzymol.* 128: 3–41(1986)).

Different host cells have characteristic and specific mechanisms for the translational and post-translational processing and modification (e.g., glycosylation, cleavage) of proteins. Appropriate cell lines or host systems can be chosen for the presence of appropriate transcription factors—as set forth herein—for screening of compounds which increase transcription.

Any of a series of yeast gene sequence expression systems can be utilized which incorporate promoter and termination elements from the actively expressed gene sequences coding for glycolytic enzymes. These enzymes are produced in large quantities when yeast are grown in mediums rich in glucose. Known glycolytic gene sequences can also provide very efficient transcriptional control signals.

A wide variety of transcriptional and translational regulatory sequences can be employed, depending upon the nature of the host. The transcriptional and translational regulatory signals can be derived from viral sources, such as adenovirus, bovine papilloma virus, simian virus, or the like, where the regulatory signals are associated with a particular gene sequence which has a high level of expression. Alternatively, promoters from mammalian expression products, such as actin, collagen, myosin, and the like, can be employed.

As discussed above, expression of heterologous protein in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., *J. Mol. Appl. Gen.* 1:273–288 (1982)); the TK promoter of Herpes virus (McKnight, *Cell* 31:355–365 (1 982)); the SV40 early promoter (Benoist et al., *Nature* (London) 290:304–310 (1981)); the yeast gal4 gene sequence promoter (Johnston et al., *Proc. Natl. Acad. Sci.* (*USA*) 79:6971–6975 (1982); Silver et al., *Proc. Natl. Acad. Sci.* (*USA*) 81:5951–5955 (1984)) and the CMV immediate-early gene promoter (Thomsen et al., *Proc. Natl. Acad. Sci* (*USA*) 81:659–663 (1984).

A nucleic acid construct comprising a promoter and an ARE operably linked to a heterologous protein coding sequence can be introduced into a recipient prokaryotic or eukaryotic cell either as a non-replicating DNA (or RNA) molecule, which can either be a linear molecule or, more preferably, a closed covalent circular molecule. Since such molecules are incapable of autonomous replication without an origin of replication, the expression of the gene can occur through the transient expression of the introduced sequence. Alternatively, permanent expression can occur through the integration of the introduced DNA sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the ARE. The marker can provide for prototrophy to an auxotrophic host, biocide resistance, e.g., resistance to antibiotics, or heavy metals, such as copper, or the like. The selectable marker gene sequence can either be directly linked to the DNA gene sequences to be expressed, or introduced into the same cell by co-transfection. Preferably, expression of the marker can be quantitated and plotted linearly.

In a preferred embodiment, the introduced nucleic acid molecule will be incorporated into a plasmid or viral vector capable of autonomous replication in the recipient host. Any of a wide variety of vectors can be employed for this purpose. Factors of importance in selecting a particular plasmid or viral vector include: the ease with which recipient cells that contain the vector can be recognized and selected from those recipient cells which do not contain the vector; the number of copies of the vector which are desired in a particular host; and whether it is desirable to be able to "shuttle" the vector between host cells of different species.

Preferred eukaryotic vectors include, for example, BPV, vaccinia virus, SV40, retroviruses, adenoviruses, AAV, 2-micron circle, and the like, or their derivatives. Such vectors are well known in the art (Botstein et al., *Miami Wntr. Symp.* 19:265–274 (1982); Broach, In: *The Molecular Biology of the Yeast Saccharomyces: Life Cycle and Inheritance*, Cold Spring Harbor Laboratory, Cold Spring Harbor, N.Y., p. 445–470 (1981); Broach, *Cell* 28:203–204 (1982); Bollon et al., *J. Clin. Hematol. Oncol.* 10:39–48 (1980); Maniatis, In: *Cell Biology: A Comprehensive Treatise*, Vol. 3, Gene Sequence Expression, Academic Press, NY, pp. 563–608 (1980); *Current Protocols in Molecular Biology*, Eds. Ausubel et al., John Wiley and Sons, Inc. (1997, including up to Suppl. 37)); *Gene Therapy*, Eds. Lemoine et al., BIOS Scientific Publishers, Oxford (1996)).

Once the vector or nucleic acid molecule containing the construct(s) has been prepared for expression, the DNA construct(s) can be introduced into an appropriate host cell by any of a variety of suitable means, i.e., transformation, transfection, viral infection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene molecule(s) results in the production of the heterologous protein.

Introduced DNA being "maintained" in cells should be understood as the introduced DNA continuing to be present in essentially all of the cells in question as they continue to grow and proliferate. That is, the introduced DNA is not diluted out of the majority of the cells over multiple rounds of cell division. Rather, it replicates during cell proliferation and at least one copy of the introduced DNA remains in almost every daughter cell. Introduced DNA may be maintained in cells in either of two fashions. First, it may integrate directly into the cell's genome. (This occurs at a rather low frequency.) Second, it may exist as an extrachromosomal element, or episome. In order for an episome not to be diluted out during cell proliferation, a selectable marker gene can be included in the introduced DNA and the cells grown under conditions where expression of the marker gene is required. Even in the case where the introduced DNA has integrated in the genome, a selectable marker gene may be included to prevent excision of the DNA from the chromosome.

III. A Method of Screening for a Compound That Increases Transcription of an mRNA Regulated by an Antioxidant Responsive Element According to the invention, the transfected cell line described above would provide a convenient tool for screening candidate compounds which increase transcription of an mRNA regulated by an antioxidant responsive element. Preferably, the cell line is stably transfected. However, in another embodiment of the invention, the cell is transiently transfected. A culture of the transfected cell line could be grown in the presence of the candidate compound, lysed and the lysate assayed for increased expression of the heterologous protein coding sequence which is operably linked to the ARE, as described herein. In parallel, a culture grown in the absence of the candidate compound could be lysed and assayed. The assay results would then be compared to determine whether the candidate compound increased expression of the heterologous protein. The advantage of this method is the convenience provided by not having to introduce a DNA construct transiently every time a candidate compound is screened. In a preferred embodiment, the structural gene encoding the heterologous protein is a reporter gene.

In a further embodiment, the present invention relates to a method of screening for a compound (preferably, a drug; also preferably, an antioxidant, further preferred compounds are described infta) that increases transcription of an mRNA regulated by an antioxidant responsive element (preferably by interacting with the antioxidant responsive element; such interaction may be direct or indirect as discussed herein), comprising the steps of:

(a) assaying a first cellular extract for the amount of transcription of the mRNA wherein the mRNA is expressed from a DNA construct, the transcription being in the absence of a candidate compound and the DNA construct comprising:
  an antioxidant responsive element (ARE) having a DNA sequence 5'-RGR AC NNN GCT-3' (SEQ ID NO:1) operably linked to a protein coding sequence;
(b) assaying a second cellular extract for the amount of transcription of the mRNA wherein the mRNA is expressed from the DNA construct, the transcription being in the presence of the candidate compound; and
(c) comparing the amounts of transcription of the first extract and the second extract, wherein a greater amount of transcription in the second extract as compared to the first extract indicates that the candidate compound increases transcription of the mRNA regulated by the antioxidant responsive element.

In another embodiment, the present invention relates to a method of screening for a compound (preferably, a drug; also preferably, an antioxidant, further preferred compounds are described infra) that increases transcription of an mRNA regulated by an antioxidant responsive element (preferably by interacting with the antioxidant responsive element; such interaction may be direct or indirect as discussed herein), comprising the steps of:

growing a first culture of the cells comprising an above-described DNA construct in the absence of the candidate compound (e.g., the antioxidant), lysing the first culture to produce a first extract;

assaying the first extract for the amount of transcription of an mRNA which comprises the structural coding sequence;

growing a second culture of the cells comprising an above-described DNA construct in the presence of the candidate compound;

lysing the second culture to produce a second extract;

assaying the second extract for the amount of transcription of an mRNA which comprises the structural coding sequence; and comparing the amounts of transcription of the first extract and the second extract, wherein a greater amount of transcription in the second extract as compared to the first extract indicates that the candidate compound increases transcription of an mRNA regulated by the antioxidant responsive element. The above described method can include the first step of introducing into an above-described cell an above-described DNA construct.

In one preferred embodiment, the candidate compound is identified or created via combinatorial chemistry. For example, the compound may mimic the structure of an antioxidant but is not known to be an antioxidant itself. In another preferred embodiment, the compound is a transcription factor which binds the ARE. The transcription factor may be a protein or protein complex. It may be bound to a small molecule, such as, for example, an antioxidant.

Assays for transcription are meant to include, but not be limited to, (1) the direct analysis of the amount of mRNA present in the extract, (2) analysis of the amount of protein present in the extract (which is indicative of the amount of transcription present, though RNA stability is also involved here) and (3) analysis of a chemical or phenotypic change which is indicative of the amount of transcription of a protein coding sequence. Preferably, a linear response is obtained. Preferably, the compound is a drug. More preferably, the compound is an antioxidant.

Thus, in a further embodiment, the present invention relates to a method of screening for a compound (preferably, a drug; also preferably, an antioxidant, further preferred compounds are described infra) that increases transcription of an mRNA regulated by an antioxidant responsive element (preferably by interacting with the antioxidant responsive element; such interaction may be direct or indirect as discussed herein), comprising the steps of:

(a) assaying a first cellular extract for the amount of protein produced from an mRNA wherein the mRNA is expressed from a DNA construct, the expression being in the absence of a candidate compound and the DNA construct comprising:
  an antioxidant responsive element (ARE) having a DNA sequence 5'-RGR AC NNN GCT-3' (SEQ ID NO:1) operably linked to a protein coding sequence;
(b) assaying a second cellular extract for the amount of protein produced from an mRNA wherein the mRNA is expressed from the DNA construct, the transcription being in the presence of the candidate compound; and
(c) comparing the amounts of protein of the first extract and the second extract, wherein a greater amount of protein in the second extract as compared to the first extract indicates that the candidate compound increases transcription of the mRNA regulated by the antioxidant responsive element.

In another embodiment, the present invention relates to a method of screening for a compound that increases transcription of an mRNA regulated by an antioxidant responsive element, comprising the steps of:

growing a first culture of cells comprising an above-described DNA construct in the absence of a candidate compound, lysing the first culture to produce a first extract;

assaying the first extract for the amount of protein encoded by the heterologous protein coding sequence;

growing a second culture of the cells in the presence of the candidate compound, lysing the second culture to produce a second extract;

assaying the second extract for the amount of protein encoded by the heterologous protein coding sequence; and comparing the amounts of the protein of the first extract and the second extract, wherein a greater amount of the protein in the second extract as compared to the first extract indicates that the candidate compound increases transcription of an mRNA regulated by the antioxidant responsive element. The above-described method can include the step of first introducing into a cell an above-described DNA construct.

The construct could also include an additional functional selectable marker gene whose expression is required under certain culture conditions to maintain the introduced DNA in the cells. For example, expression of the marker gene could provide resistance to hygromycin B (Wilson et al., *Plasmid* 33: 198–207 (1995)). If the cells were consistently cultured in the presence of hygromycin B (Boehringer-Mannheim), only cells comprising this marker gene would survive selection. Thus, the introduced DNA would be stably maintained in essentially all surviving cells. Similarly, if the marker gene coded for neomycin resistance (Colbere-Garapin et al., *J. Mol. Biol.* 150: 1–14 (1981)) and the cells were cultured in the presence of G418 (Geneticin, Life Technologies), the introduced DNA would be stably maintained. Other genes of this type, such as, for example, aminoglycoside phosphotransferase (APH) (Jimenz et al., *Nature* (London) 287: 869–871 (1980)) would be known to a person skilled in the art.

It is important to note that the present invention as described herein is the first demonstration of antioxidant-induced protein-DNA interactions involved in the regulation of expression of the apo AI gene, as well as the first description of a specific ARE involved in regulation of apo AI. The invention (described herein) provides convenient DNA constructs, and convenient, rapid and efficient methods for screening for candidate compounds that may be involved in increasing expression of the apo AI gene through the mediation of the ARE.

The invention contemplates the assembly of a kit including reagents with which one could conveniently practice the invention. The kit would include a DNA construct comprising a reporter gene as described herein, as well as a substrate of the reporter gene so that reporter gene activity could be quantitated. The invention also contemplates automation of the methods described herein. That is, a machine could be constructed that would practice the invention, further increasing convenience and efficiency.

IV. Compounds (Including Proteins) that Bind an ARE

In another embodiment, the present invention relates to a purified compound (preferably, a transcription factor) (preferably, a protein) that binds to an above-described antioxidant responsive element (ARE). Preferably, the present invention relates to a substantially pure compound. Gel mobility shift assays with an ARE oligonucleotide revealed increased levels of a specific protein-DNA complex that formed with nuclear extracts from gramoxone-treated cells. UV cross-linking experiments with the ARE and nuclear extracts from either untreated or gramoxone-treated cells detected proteins of approximately 100 and 115 kDa. Accordingly, in one preferred embodiment the purified compound is a protein having a molecular weight as determined by SDS-PAGE electrophoresis of about 100 or about 115 kDa.

Thus, the invention additionally contemplates use of the ARE as a reagent for the purification of a compound (preferably, a transcription factor) with which it interacts. For example, an oligonucleotide including the ARE could be conjugated to a resin to produce an affinity resin (de Wet et al., *DNA* 3. 437–447 (1984)). A crude cell extract, such as a nuclear extract, could be incubated with the affinity resin under conditions where a transcription factor or factors would bind to the ARE moiety. After first washing the complexed resin to dissociate free and non-specifically bound proteins or protein complexes, a more stringent buffer would then be applied to elute specifically bound factors. This procedure could be performed using column chromatography or batchwise extraction as is known in the art. The transcription factors could be further purified by SDS-PAGE electrophoresis. The amino acid sequence of the transcription factors could be determined using protein isolated from the SDS-PAGE gel as is known in the art.

One skilled in the art can readily follow other known methods for isolating proteins in order to obtain the transcription factor free of natural contaminants. These include, but are not limited to: size-exclusion chromatography, HPLC, ion-exchange chromatography, and immuno-affinity chromatography.

In a preferred embodiment, the purification procedures comprise ion-exchange chromatography and size exclusion chromatography. Any one of a large number of ion-exchange resins known in the art can be employed, including for example, phosphocellulose, DEAE-Sephadex, monoQ, sepharose Q, macro-prepQ, AG1-X2, or HQ. Examples of suitable size exclusion resins include, but are not limited to, Superdex 200, Superose 12, and Sephycryl 200. Elution can be achieved, for example, with aqueous solutions of potassium chloride or sodium chloride at concentrations ranging from 0.01M to 2.0M.

The present invention is described in further detail in the following non-limiting examples.

EXAMPLES

The following protocols and experimental details are referenced in the examples that follow.

Materials

Complementary pairs of oligonucleotides were synthesized using the Beckman Oligo 1000 DNA Synthesizer according to the manufacturer's instructions. The following oligonucleotides (and their complementary strands) were prepared:

| | |
|---|---|
| ApoAI-ARE (SEQ ID NO: 34) | 5'-CAGCCCCAGGGACAGAGCTG-3' |
| Mutated ARE (SEQ ID NO: 35) | 5'-CAGCCCCATTTGAGTGTATG-3' |
| GST-ARE (SEQ ID NO: 36) | 5'-CTAATGGTGACAAAGCAG-3' |
| Xenobiotic response element (XRE) (SEQ ID NO: 37) | 5'-AGTGCTGTCACGCTAG-3' |

Cell culture and drug treatments

The human hepatoma cell line, HepG2, was obtained from the American Type Culture Collection (Rockville, Md.). Cells were grown in T75 flasks comprising 20 ml of Eagle Minimal Essential Medium (MEM) supplemented with 10% fetal bovine serum (FBS) as described previously (Tam, S. P., et al., *J. Biol. Chem.* 260:1670–1675 (1985)). Freshly confluent monolayers were washed twice with MEM and then incubated with fresh medium for 0 to 8 hours in the absence or presence of gramoxone, dissolved in phosphate buffered saline (PBS), ranging from 0.1 μM to 10 μM. In some experiments, gramoxone and cycloheximide were added to cells to give final concentrations of 0.1 μM and 10 μg/ml, respectively. Where noted, HepG2 cells were also treated with or without gramoxone and in the presence of actinomycin D (1 μg/ml), for various time periods as described in the figure legends. Cell viability was routinely monitored by trypan blue exclusion and lactate dehydrogenase leakage as described previously (Tam, S- P. and Deeley, R. G., *Atherosclerosis* 105:235–243 (1994)). In all experiments the number of dead cells never exceeded 5% of the total number of cells.

RNA isolation and detection

Total cellular RNA was isolated using the acid guanidinium thiocyanate-phenol-chloroform extraction method described by Chomczynski, P. and Sacchi, N., *Anal. Biochem.* 162:156–159 (1987). RNA detection and quantitation were achieved by slot blot analyses. For slot blots, multiple RNA samples (0.5 to 5.0 μg) from cells cultured under a variety of conditions were denatured with formaldehyde and applied to wells of a slot blot apparatus (Bio-Rad) onto Zeta-probe GT membranes. Blots were prehybridized and hybridized with nick- translated apoAI, apoB and apoE cDNA probes as described (Tam, S- P., *Atherosclerosis* 91:51–61 (1991)). Detection of catalase mRNA levels was essentially under the same conditions as described for apolipoprotein mRNAs (Tam, S- P., *Atherosclerosis* 91:51–61 (1991)). The catalase cDNA probe was obtained from the American Type Culture Collection (ATCC). All results were normalized using densitometric analyses of slot blots probed with radiolabelled oligo-dT to correct for loading variations.

Nuclear run-off transcription assay and preparation of nuclear extracts

Nuclei were prepared according to the procedure of Bartalena, L., et al., *Mol. Endocrinol.* 6:935–942 (1992). An in vitro nuclear run-off transcription assay was carried out as described (Bartalena, L., et al., *Mol. Endocrinol.* 6:935–942 (1992)) with minor modifications (Tam, S- P. and Deeley, R. G., *Atherosclerosis* 105:235–243 (1994)). Procedures for nuclear run-off transcription assays and preparation of nuclear extracts from HepG2 cells have been described in detail previously (Zhang, X., et al., *J. Biol. Chem.* 271:27152–27160 (1996)).

Bandshift assays

For bandshift assays, nuclear extracts (1.0 μg) were incubated with 100 μg of poly (dI-dC) in binding buffer comprising 5 mM DTT and 5 μM $ZnCl_2$, on ice for 30 minutes. Then 2 fmoles (10,000 cpm) 5' end labelled synthetic oligonucleotides corresponding to either the apoAI-ARE or GST-ARE were added to the reaction mixtures and incubated on ice for another 30 minutes. Procedures for bandshift assays have been described in detail previously (Zhang et al., *J. Biol. Chem.* 271:27152–27160 (1996)). Competition assays were performed by adding the unlabelled competitor DNA 15 minutes prior to the addition of either labelled apoAI-ARE or GST-ARE.

Ultraviolet irradiation cross-linking experiments

Ultraviolet (UV) cross-linking experiments were carried out as described by Wu, C., et al., *Science* 238:1247–1253 (1987) with minor modifications. Briefly, the binding reactions were first carried out as described above for bandshift assays, except that the reaction was scaled up 25-fold. The binding reactions were irradiated on ice for 30 min. with a 254 nm wavelength ultraviolet source (Stratalinker). Equal amounts of 2× SDS sample buffer were added to the irradiated reactions. The samples were then heated at 90° C. for 10 min. and electrophoresed on an 8% polyacrylamide/SDS denaturing gel by the method of Laemmli, U. K., *Nature* 227:680–685 (1970). The gel was dried and autoradiographed.

Preparation of luciferase constructs

Two GeneLight™ vectors (Promega, LifeTechnologies) were used: pGL2-Basic (pGL2-B) and pGL2-Promoter (pGL2-P). A 491 bp DNA fragment of the human apoAI promoter between nucleotides −491 to +1 was generated by polymerase chain reaction (PCR) amplification described in detail previously (Zhang, X., et al., *J. Biol. Chem.* 271:27152–27160 (1996) and Tam et al., Canadian Patent Application No. 2,159,532). The sequence of this DNA fragment was confirmed by DNA sequencing. The fragment was inserted into the XhoI site of the pGL2-Basic vector, upstream of the luciferase gene. This plasmid is hereafter referred to as pGL2(apoAI-491)luc. Plasmid pGL2(apoAI-250)luc was constructed by releasing a DNA fragment (−491 to −251 of the apoAI promoter) from pGL2(apoAI-491) luc using SmaI. The vector was gel purified and re-ligated.

Plasmid pGL2 (apoAI-250 mutant ARE) luc was prepared by a PCR-based protocol as described by Morrison, H. G. and Desrosiers, R. C., *BioTechniques* 14:454–457 (1993). To generate this mutated ARE plasmid, two sets of primers were used. One set of primers, designated GL and LUC, was hybridized to specific regions of the plasmid pGL2. The other set of primers which comprised the mutagenic ARE residues was named primers FOR and REV. The primers GL (5'-TGTATCTTATGGTACTGTAACTG-3') (SEQ ID NO: 38) and REV (5'-GATCATACACTCAAATGGGGCTGGG-3') (SEQ ID NO: 39) were complementary to the non-coding strand of DNA, while primers FOR (5'-CCCATTTGAGTGTATGATCCTTGAAC-3') (SEQ ID NO: 40) and LUC (5'-GGCGTCTTCCATTTTACC-3') (SEQ ID NO: 41) were complementary to the coding strand of DNA. The plasmid pGL2 (apoAI-250) luc was used as the PCR template. Amplification was carried out as described previously (Zhang, X., et al., *J. Biol. Chem.* 271:27152–27160 (1996) and Tam et al., Canadian Patent Application No. 2,159,532). The DNA fragment generated was then digested with Sma I and Hind III and the resulting DNA fragment was purified from an agarose gel. The purified DNA fragment was cloned into the Sma I and Hind III sites of the pGL2-basic (Promega Inc.) to generate pGL2 (apoAE-250 mutant ARE) and used to transform competent *E. coli* cells. DNA was prepared from individual clones by the alkaline lysis miniprep procedure and the entire DNA insert including the area of mutagenesis was sequenced using the Sequenase version 2.0 system (United States Biochemicals).

A series of pGL2-P vectors comprising apoAI-ARE, GST-ARE and mutated ARE (sequences given above under "Materials") were also constructed. pGL2-P was digested with the restriction enzymes KpnI and NheI. The restriction digest was electrophoresed and the digested plasmid was gel purified. Synthetic oligomers corresponding to the putative ARE from the apoAI promoter (apoAI-ARE), the consensus GST-ARE (Rushmore et al., *J. Biol. Chem.* 266:4556–4561 (1991)), and mutated ARE were inserted individually into the KpnI and NheI sites of the linearized pGL2-P vectors, all synthetic oligomers comprising a 5'-KpnI and a 3'-NheI site to facilitate unidirectional cloning into the pGL2-P vector. The sequence of all pGL2-P constructs was confirmed by DNA sequencing.

Transfection and luciferase assay

The human hepatoma cell line, HepG2, was maintained as monolayers on 100 mm plates in MEM supplemented with 10% FBS. Transient DNA transfections were performed by the calcium phosphate precipitation procedure described by Gorman, C. M., et al., *Mol. Cell. Biol.* 2:1044–1051 (1982) and detailed previously (Zhang, X., et al., *J. Biol. Chem.* 271:27152–27160 (1996) and Tam et al., Canadian Patent Application No. 2,159,532). The cells were then cultured in the absence or presence of gramoxone (0.1 $\mu$M) ranging from 0–8 hours.

Transfected HepG2 cells were harvested by washing three times in PBS and assayed for luciferase activity as described in the Luciferase Assay Kit Technical Manual, Promega, Inc. (Genelight™ Plasmids Technical Manual Promega Corporation, WI, (1991), pp. 1–39). This assay has also been described in detail previously (Zhang, X., et al, *J. Biol. Chem.* 271:27152–27160 (1996) and Tam et al., Canadian Patent Application No. 2,159,532). In all transfections, 5 82 g of an internal control plasmid (pSGΔLacZ) comprising the *E. coli* LacZ gene under the control of the SV40 early promoter and enhancer, were included in order to correct for differences in transfection and harvesting efficiency. Transfected cells were harvested and β-galactosidase activities in the cell lysates determined as described (Zhang, X., et al., *J. Biol. Chem.* 271:27152–27160 (1996) and Tam et al., Canadian Patent Application No. 2,159,532). The pGL2-promoter vector which comprises a SV40 promoter was used as a reference for both transfection and luciferase assays. All luciferase activities are reported as mean ±S.E.M. Significance of group differences was determined by Student's t-test, using two-tailed P values.

The present invention is described in further detail in the following non-limiting examples.

Example 1

Modulation of Steady State Apolipoprotein mRNA Levels by Gramoxone

The effects of gramoxone on levels of apolipoprotein mRNAs were examined by slot blot analysis using the level of total polyA$^+$ RNA determined by oligo dT hybridization to control for variation in RNA loading. Exposure of HepG2 cells to gramoxone at concentrations of either 0.1, 1.0 or 10.0 $\mu$M for 8 hours resulted in a 2-fold reduction in apoAI mRNA levels. However, there were no significant changes in the levels of apoB and apoE mRNA at any of the above concentrations of drug tested. At a concentration >10 $\mu$M, gramoxone decreased cell viability significantly. Therefore, in all further experiments, the drug was used at 0.1 $\mu$M.

Example 2

Analysis of Gramoxone Temporal Response Profiles

Time course studies of the effect of gramoxone on apoAI mRNA levels in HepG2 cells were performed to determine whether or not the decline in steady state levels of apoAI mRNA could be seen earlier than 8 hours. Newly confluent HepG2 cells were grown in media comprising 10% FBS. Cell were then cultured in the presence of gramoxone (0.1 $\mu$M) for various time periods. Total RNA was isolated at 0, 1, 2, 4, 6, and 8 h. The levels of apoAI, apoB and apoE mRNAs were determined by slot blot analysis (FIG. 1). All results were normalized using densitometric analyses of slot blots probed with radiolabelled oligo dT to correct for loading variations. Steady state levels of apoAI, apoB and apoE mRNAs from untreated cells were arbitrarily set at 100%. Results are mean ±S.E.M. of four experiments (FIG. 1).

After 2 hours of exposure to gramoxone, apoAI mRNA levels decreased to 50% of control values and this decrease was maintained for the duration of the remaining 6 hours (FIG. 1). No significant differences in apoB and apoe mRNA levels were observed when HepG2 cells were cultured in the presence of gramoxone over the 8 hour period. To ensure that the cells were under oxidative stress, the levels of catalase mRNA were also determined. Exposure of HepG2 cells to gramoxone resulted in a 4- and 10-fold increase in steady state levels of catalase mRNA at 6 h and 8 h, respectively. This induction could be suppressed by simultaneously exposing the cells to 1% (v/v) dimethyl sulfoxide (DMSO), a free radical scavenger.

Example 3

Figure 2:
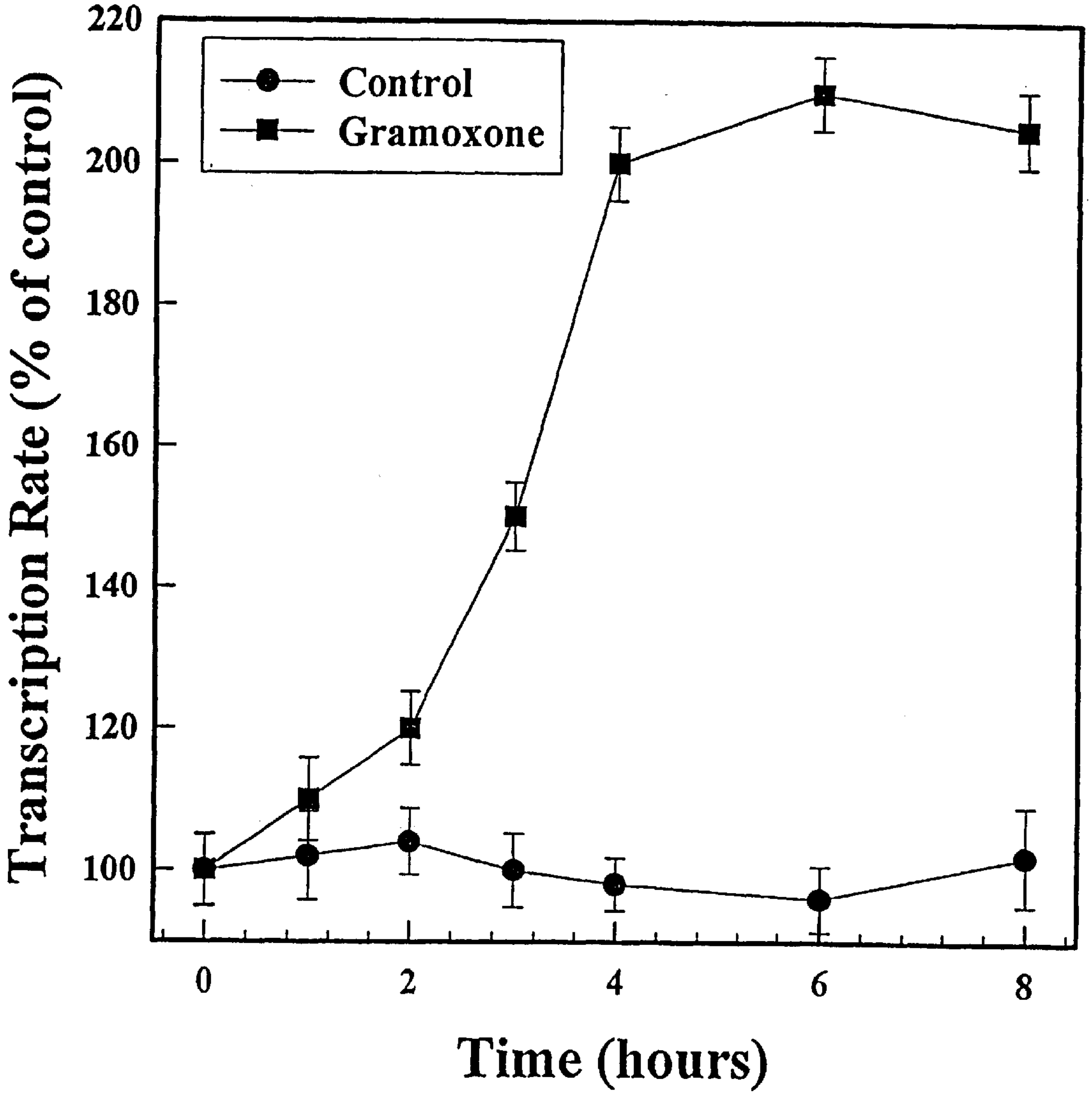

Analysis of the Effect of Gramoxone on Transcription of the apoAI Gene and Half-Life of apoAI mRNA The two-fold decrease in apoAI mRNA levels could be the result of either a decrease in rates of transcription or an increased degradation of the apoAI mRNA. Therefore, the transcription rate of the apoAI gene was measured using isolated nuclei from HepG2 cells cultured in the presence of gramoxone for 0 to 8 h. Rates of transcription of apoAI gene were determined by nuclear run-off assays using nuclei isolated from HepG2 cells cultured in the absence or presence of gramoxone (0.1 $\mu$M). Nuclei (2–3×$10^7$) were isolated at 0, 1, 2, 3, 4, 6 and 8 h. Hybridization of the newly synthesized $^{32}$P-RNA to plasmids comprising the apoAI-insert were carried out in triplicate. Nonspecific hybridization to each filter was determined by performing transcription assays with labelled pGEM 3Z control vector. Filters were washed extensively and bound radioactivity was measured by a liquid scintillation counter. Relative transcription rates were calculated as part per million (ppm)/filter=(counts/min. per filter−counts/min. background)÷amount of $^{32}$P-RNA used in hybridization (input count). These numbers were then normalized for hybridization efficiency as measured by binding of known amounts of $^3$H-riboprobes added to the hybridization mixture. This was then corrected for the size of the specific gene=ppm/gene=(ppm/filter÷% hybridization)×(gene size÷CDNA insert size). Sizes of the apoAI gene and apoAI cDNA fragments were 2.0 and 0.6 kilobases, respectively. Results are mean ±S.E.M. expressed in percentage of the 0 h time point of three independent experiments (FIG. 2). The nuclear run-off assays indicated that the rate of transcription of apoAI gene increased approximately 2-fold between 4 to 8 h after gramoxone treatment (FIG. 2).

Figure 3:
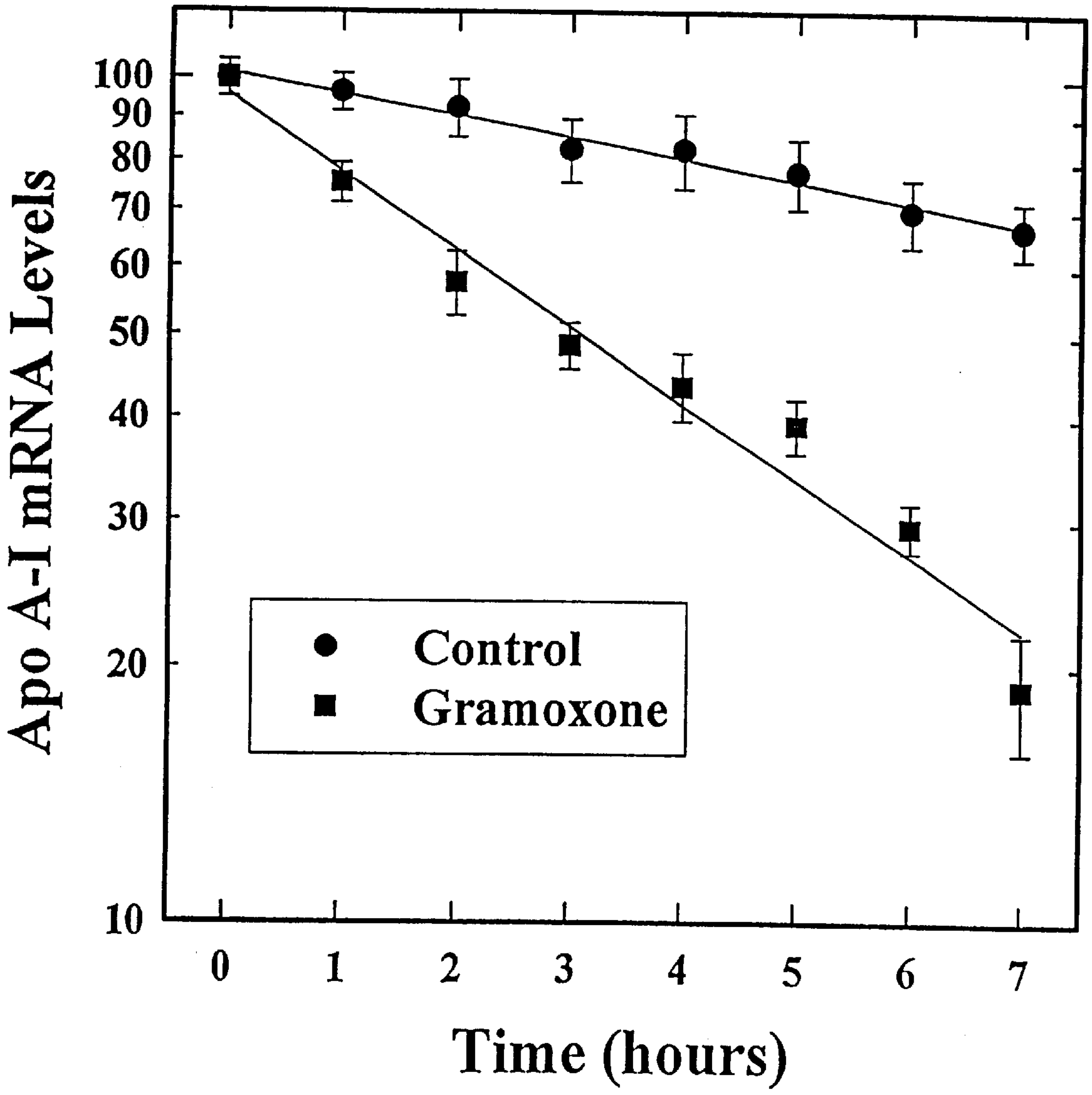

To determine if the rate of apoAI mRNA degradation also changed in response to gramoxone treatment, the turnover of apoAI mRNA was determined in the presence of actinomycin D (1 $\mu$g/ml) with and without gramoxone. Newly confluent HepG2 cells were pre-treated with actinomycin D (1 $\mu$g/ml) for half an hour. The cells were then cultured either in the presence of actinomycin D (1 $\mu$g/ml) alone (control) or in combination of actinomycin D and gramoxone (0.1 $\mu$M) for various time periods. Total RNA was isolated at 0, 1, 2, 3, 4, 5, 6 and 7 h. Time zero is represented as half an hour after actinomycin D pretreatment. The levels of apoAI mRNA under various conditions were determined. Steady state levels of apoAI mRNA at time zero were arbitrarily set at 100. Results are mean ±S.E.M. of three independent experiments (FIG. 3). The half-lives obtained for apoAI mRNAs following the addition of actinomycin D in the absence or presence of gramoxone were approximately 12.5±1.5 hours and 3.0±0.4 hours, respectively (FIG. 3). Thus, there was a 4-fold increase in the rate of degradation of apoAI mRNA when HepG2 cells were subjected to oxidative stress.

Example 4

Transient Transfection Studies

Figures 4A, 4B:
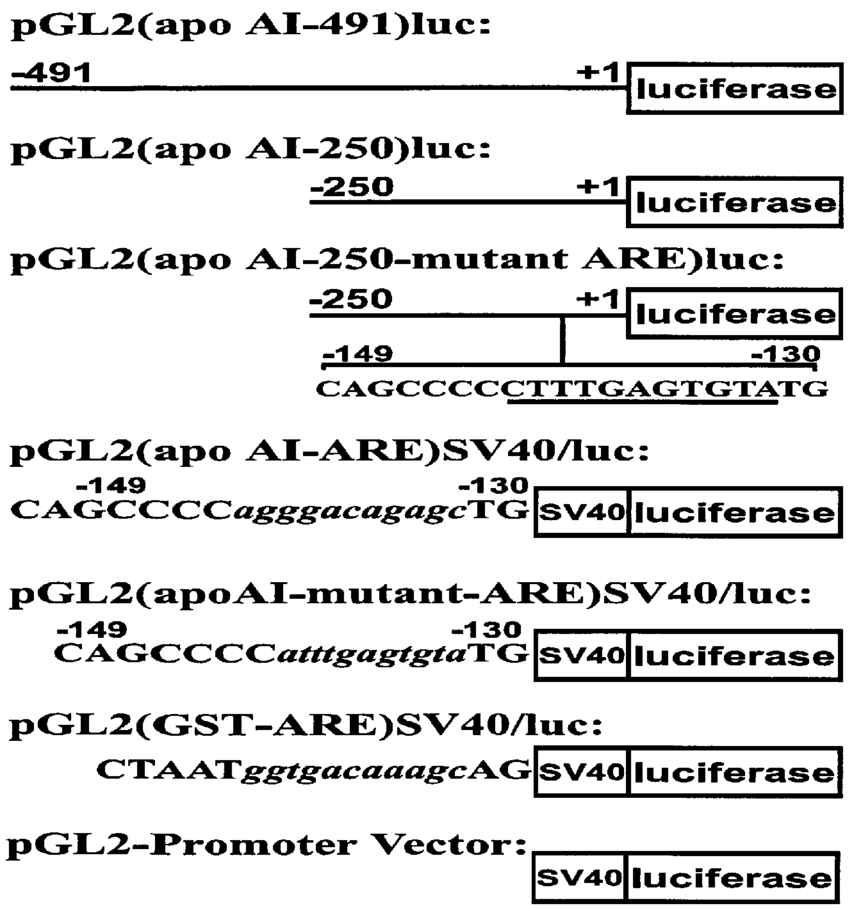

To further investigate the increase in transcription detected by nuclear run-off assays, transient transfection experiments were carried out using a series of pGL2-derived luciferase reporter plasmids. As shown in FIG. 4, both pGL2(apoAI-491)luc and pGL2(apoAI-250)luc constructs showed a significant 2-fold induction of luciferase activity in HepG2 cells cultured in the presence of gramoxone for 8 h. The 2-fold increase in apoAI promoter activity could involve a potential ARE detected by sequence comparison with the GST Ya subunit and NADP(H) quinone reductase genes. To test this hypothesis, pGL2 (apoAI-250 mutant ARE) was constructed in which the entire ARE consensus sequence was replaced (G→T, C→A, T→G, A→C). Results from these studies demonstrated that pGL2 (apoAI-250 mutant ARE) showed no increase in luciferase activity in response to gramoxone treatment. To confirm that the ARE was able to confer responsiveness to gramoxone, transient transfection experiments were carried out using a series of pGL2-P/luc constructs. The control vector pGL2-P/Luc demonstrated no change in luciferase activity in response to gramoxone treatment. Plasmids with one copy of the ARE derived from the apoAI or GST promoters pGL2(apoAI-ARE)/luc and pGL2(GST-ARE)/luc inserted upstream of the SV40 promoter, displayed a 4-fold increase in luciferase expression relative to the control vector. This suggests that the ARE enhances the basal rate of transcription of the reporter gene. Furthermore, the luciferase activity of pGL2 (apoAI-ARE)/luc and pGL2(GST-ARE)/luc was increased by an additional 2-fold in the presence of gramoxone. However, a plasmid comprising one copy of the mutant apoAI-ARE, pGL2P(apoAI-mutant ARE)/luc, had a basal rate of expression similar to the control vector and displayed no responsiveness to gramoxone.

Example 5

Protein-DNA Interaction at the ARE of the Human apoAI Proximal Promoter

Mobility shift experiments were performed to further examine the mechanism by which the ARE confers responsiveness to gramoxone. A double-stranded oligonucleotide, (apoAI-ARE) corresponding to the apoAI promoter between nucleotides −149 to −130, was end-labelled with $^{32}$p and analyzed for its ability to bind to nuclear proteins isolated from HepG2 cells cultured in the presence and absence of gramoxone.

Synthetic double-stranded oligonucleotides corresponding to either apoAI-ARE or GST-ARE were used as probes to study protein-DNA interactions. In addition, unlabelled synthetic double-stranded apoAI-ARE, GST-ARE, XRE and mutant ARE (mARE) were used as competitors. $^{32}$P-labelled apoAI-ARE (FIG. 5A) or GST-ARE (FIG. 5B) were incubated with no protein (blank) or with nuclear extracts isolated from untreated cells (control) or cells treated with gramoxone (0.1 $\mu$M) for 1 h. Competition studies were performed using gramoxone-treated nuclear extract and $^{32}$P-labelled apoAI-ARE (FIG. 5A) or GST-ARE (FIG. 5B) together with 25-, 50- and 100-fold molar excesses of unlabelled apoAI-ARE, GST-ARE, XRE and mARE oligomers, as shown. Similar results were observed in three independent experiments.

Figure 5A:
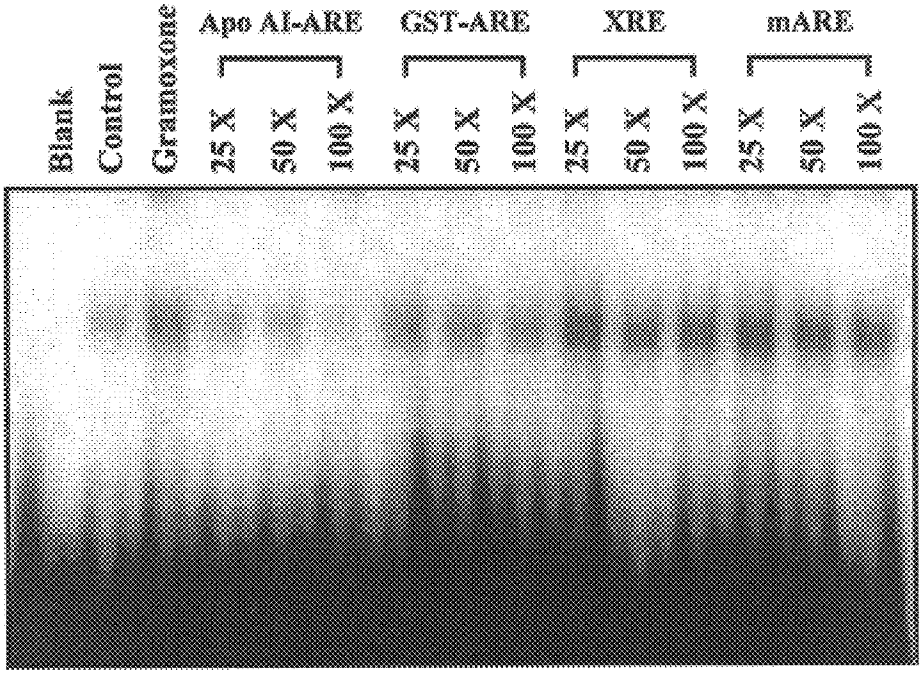

As shown in FIG. 5A, a retardation complex was detected with extracts prepared from control HepG2 cells. After 1 h of gramoxone treatment, the levels of this complex increased 2-fold. This induction was not blocked by inhibiting protein synthesis with cycloheximide. In nuclear extracts from gramoxone-treated HepG2 cells, binding to the labelled apoAI-ARE was efficiently blocked by competition with 50- to 100-fold molar excess of unlabelled apoAI-ARE and to a lesser extent with unlabelled GST-ARE. No competition was observed with up to 100-fold molar excess of the xenobiotic response element (XRE) or the mutant ARE oligomer.

Figure 5B:
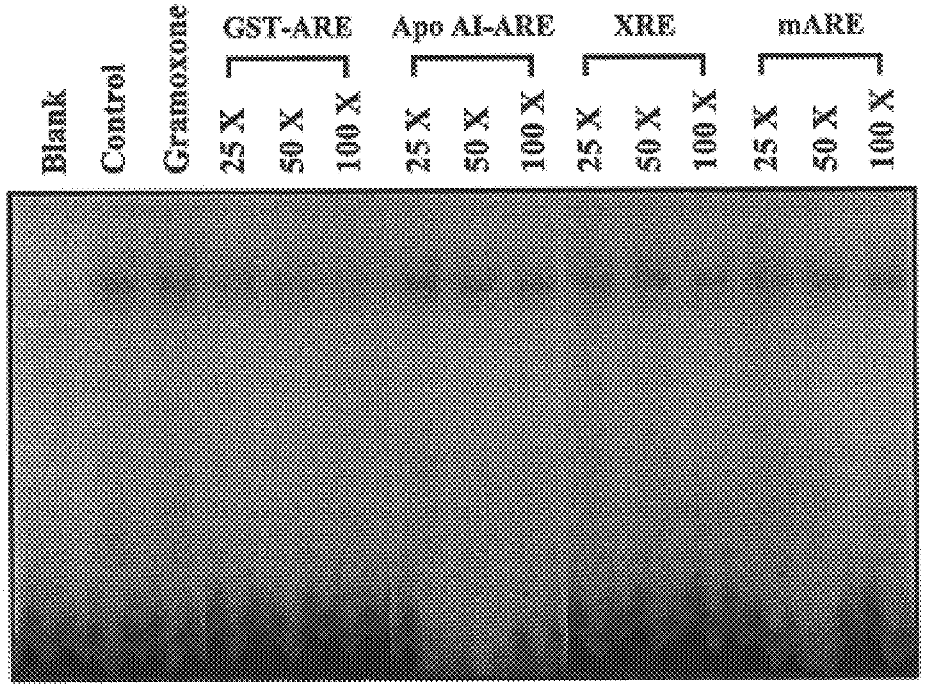

In contrast, when mobility shift assays were carried out using the GST-ARE as a probe, similar levels of binding activity were observed using nuclear extracts isolated from control and gramoxone-treated HepG2 cells (FIG. 5B). Binding to the labelled GST-ARE probe was also effectively inhibited by competition with 50- to 100-fold molar excess of unlabelled GST-ARE. However, unlabelled apoAI-ARE was not able to block the formation of the protein-DNA complex efficiently. Both negative control oligomers (XRE and mutant ARE) showed no competition for binding (FIG. 5B).

Example 6

Identification of the Trans-Acting Factor by UV Cross-Linking Experiments

Double-stranded apoAI-ARE and GST-ARE were labelled with $^{32}$p and used in binding reactions under the conditions of the gel mobility shift assays. After UV-irradiation for 30 min., equal amounts of 2× SDS sample buffer were added to the reactions. They were heated and applied to an 8% SDS-polyacrylamide gel.

Figure 6A:
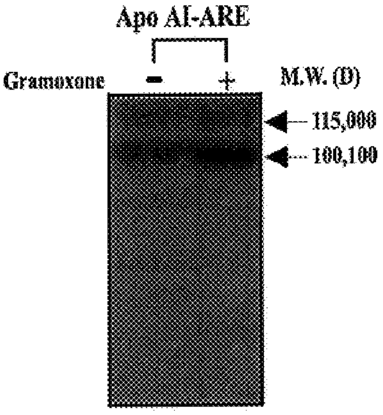
Figure 6B:
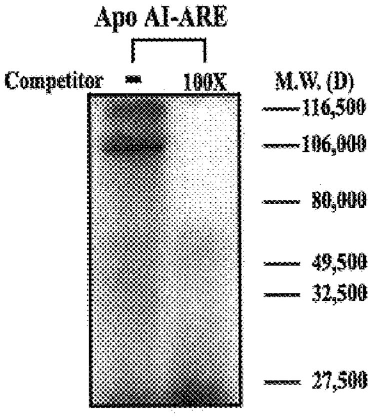
Figure 6C:
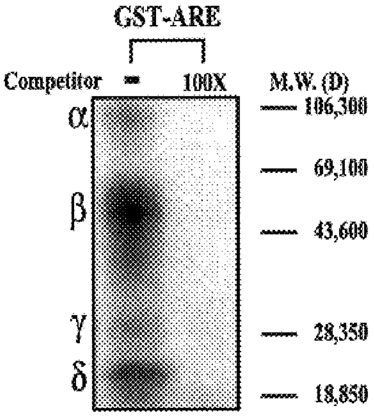
Figure 8:
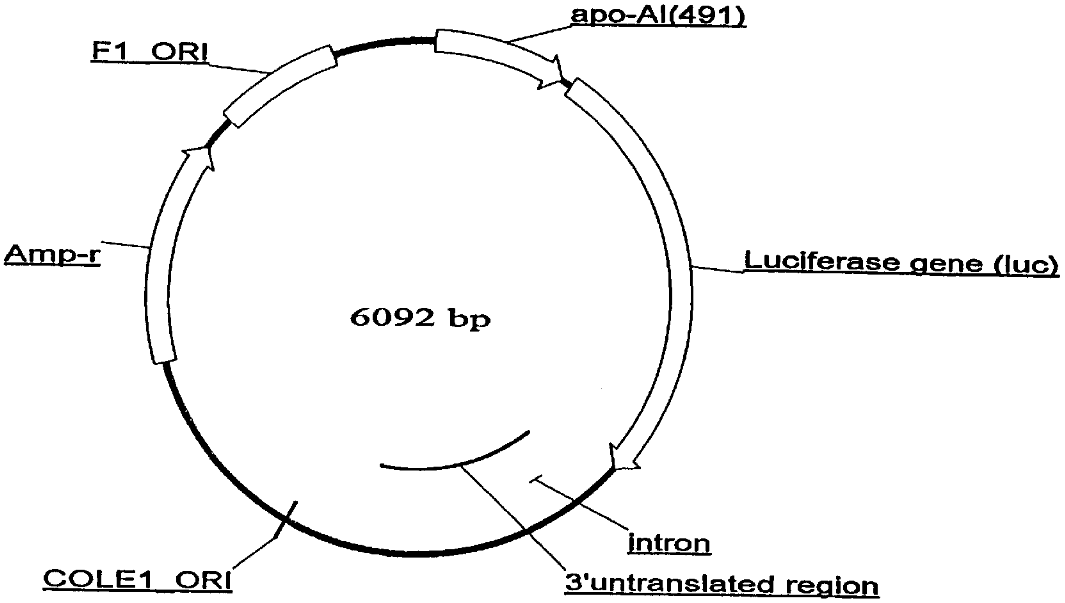
Figure 9:
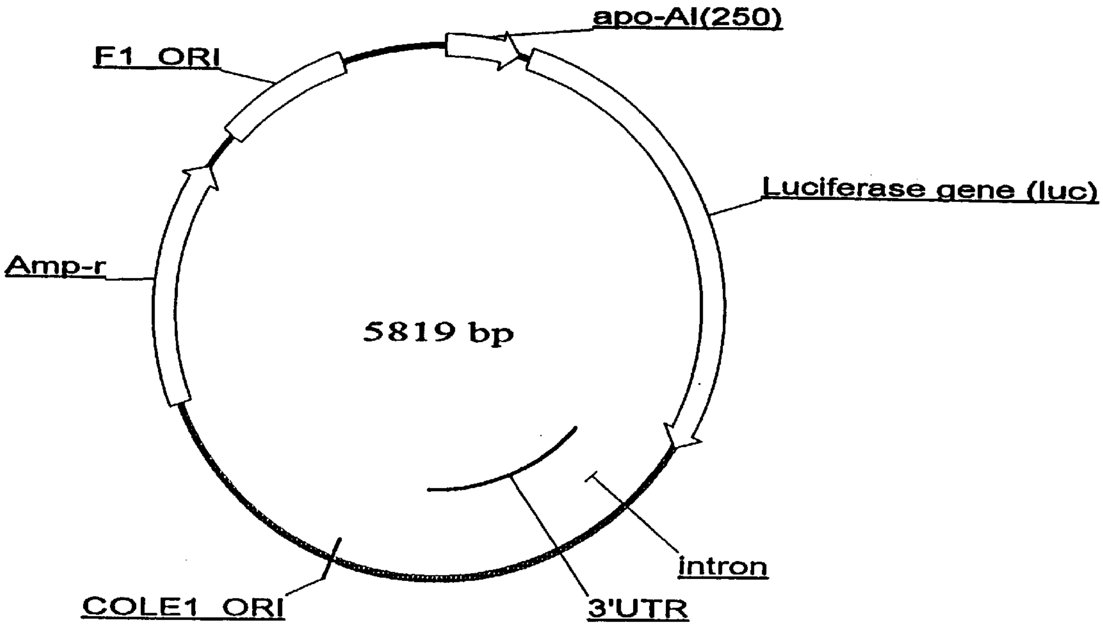
Figure 10:
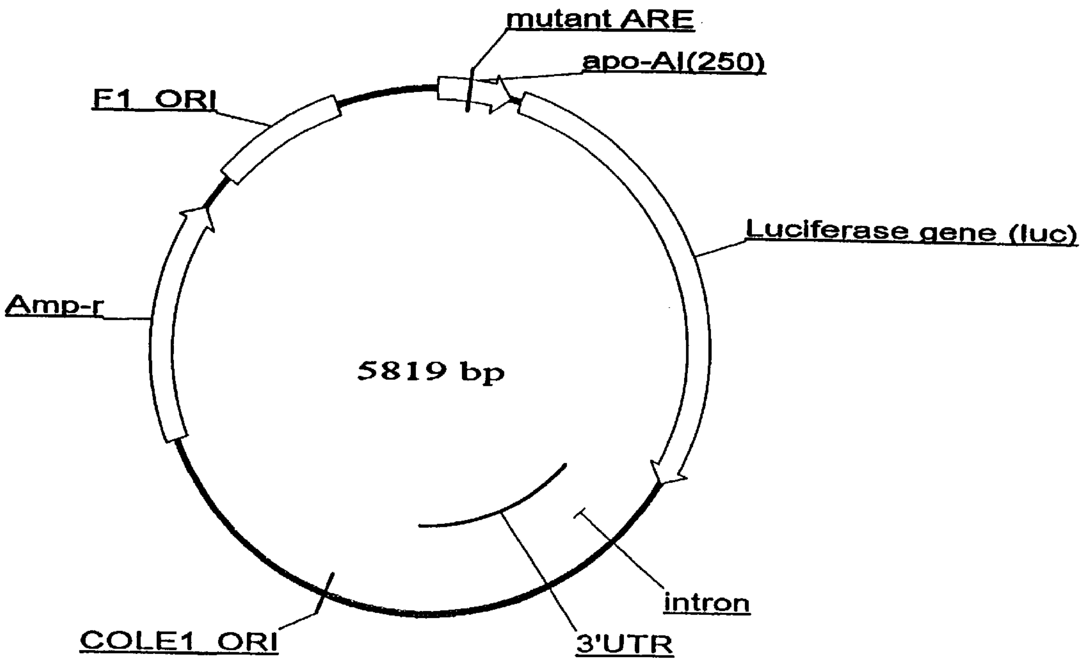
Figure 11:
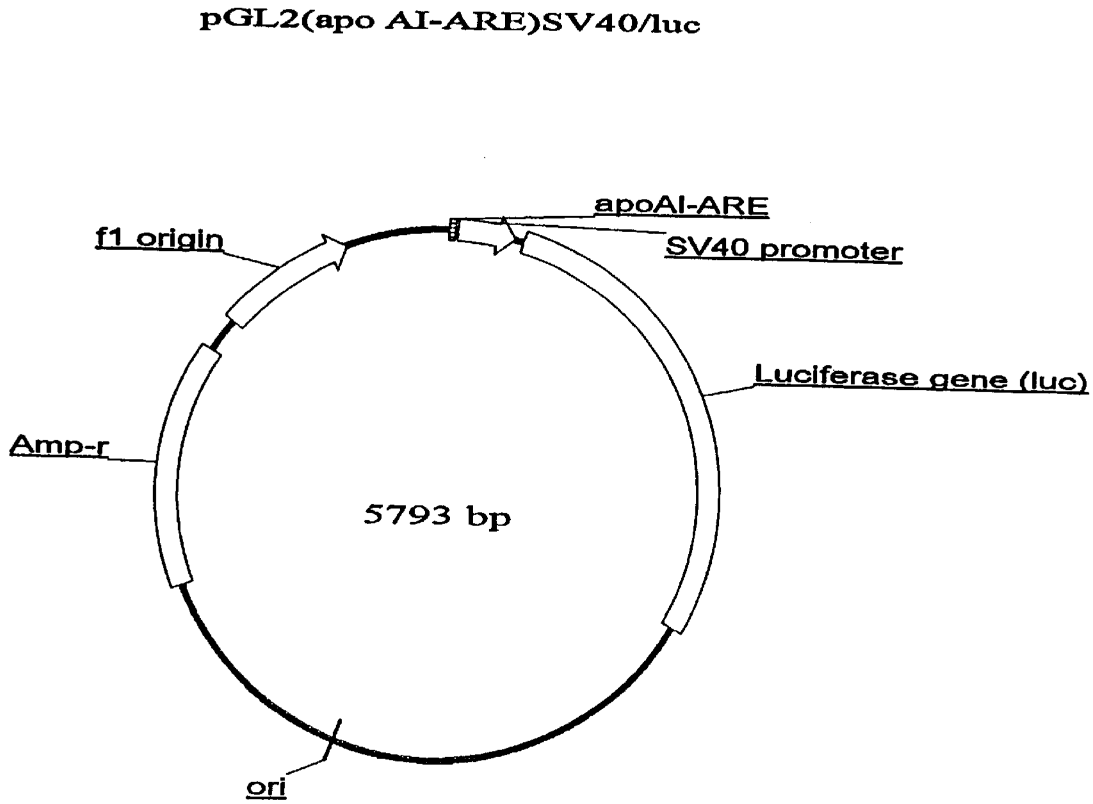
Figure 12:
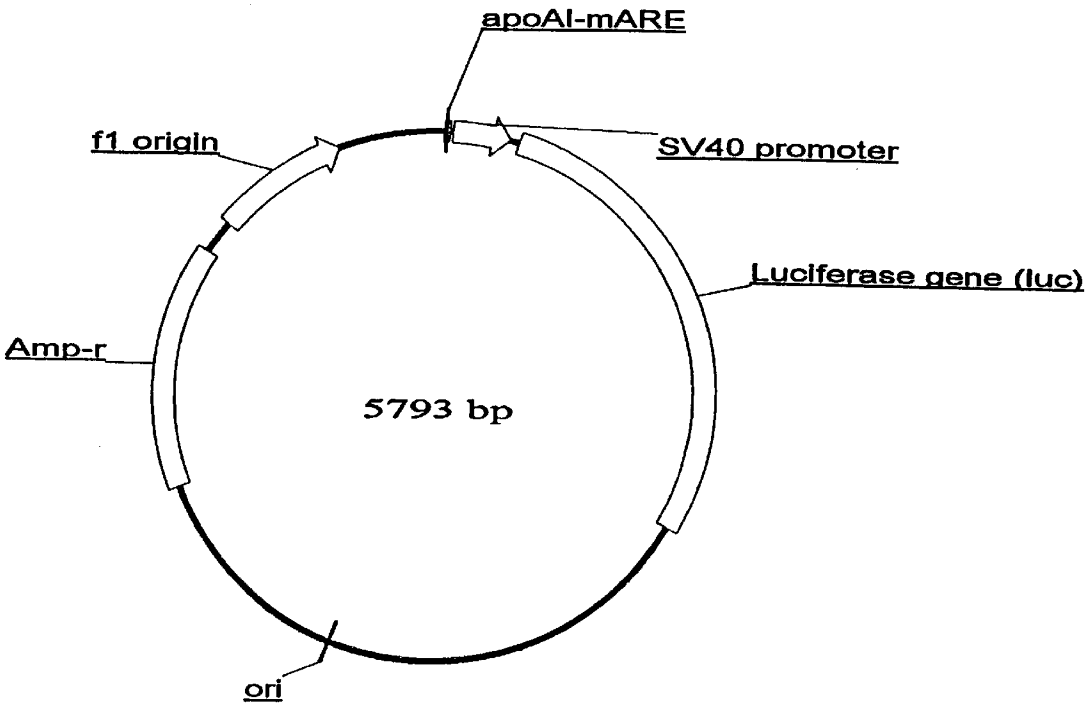
Figure 13:
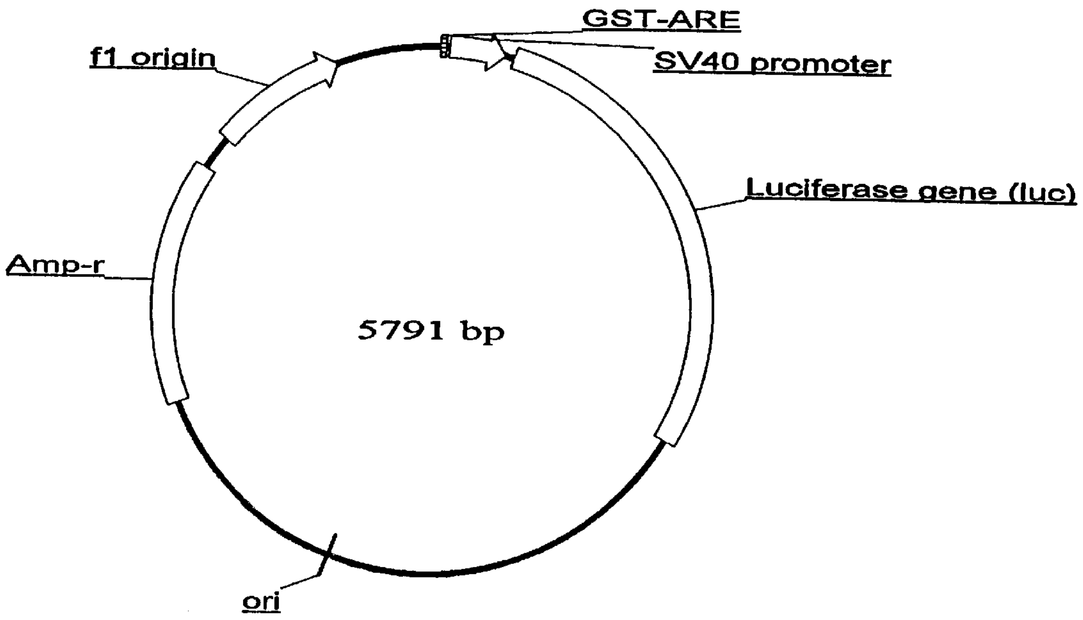
Figure 14:
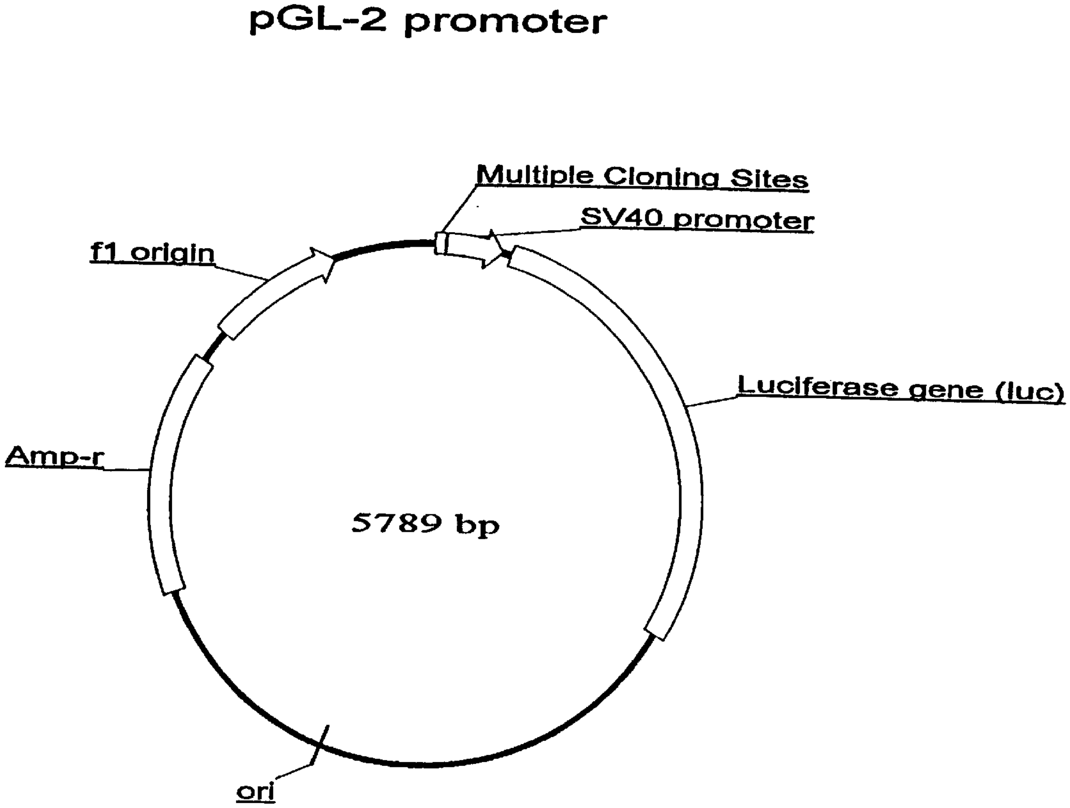

UV cross-linking experiments were carried out using labelled apoAI-ARE as a probe (FIGS. 6A and B). − and + represent nuclear extracts isolated from untreated or gramoxone-treated HepG2 cells, respectively (FIG. 6A). In FIG. 6B and C, only nuclear extracts isolated from gramoxone-treated HepG2 cells were utilized. Competition studies were performed using $^{32}$P-labelled apoAI-ARE (FIG. 6B) and GST-ARE (FIG. 6C) together with 100-fold molar excesses of unlabelled apoAI-ARE and GST-ARE, respectively. α, β, γ, and δ correspond to apparent molecular masses of approximately 98, 57, 28 and 21 kDa, respectively (FIG. 6C).

UV cross-linking studies indicated binding of two polypeptides of apparent molecular masses of approximately 115 and 100 kDa to the apoAI-ARE in both untreated and gramoxone-treated nuclear extracts (FIG. 6A), with the 100 kDa species being the predominant one bound in both extracts. Densitometry demonstrated that gramoxone treatment increased labelling of the 115 and 100 kDa proteins by approximately 71% and approximately 105%, respectively. Neither polypeptide was detected when binding reactions were supplemented with a 100-fold molar excess of unlabelled apoAI-ARE (FIG. 6B).

UV cross-linking experiments were also carried out by using labelled GST-ARE as a probe to determine whether or not proteins with similar apparent molecular masses were bound. As shown in FIG. 6C, four polypeptides of approximately 21, 28, 57 and 98 kDa were labelled using gramoxone-treated nuclear extracts and the GST-ARE. Similar results were also observed when control nuclear extracts were utilized. Densitometric analyses indicated that the 57 kDa protein was the predominant species bound, followed by the 21 kDa, 98 kDa and 28 kDa protein bands. Binding of these four polypeptides to the labelled GST-ARE probe was efficiently blocked by competition with a 100-fold molar excess of unlabelled GST-ARE.

Discussion

It has been reported that hyperoxic conditions increase steady state mRNA levels of catalase, Cu/Zn superoxide dismutase, and glutathione peroxidase in human endothelial cells (Maitre, B., et al., *Am. J. Physiol.* 265:L635–L643 (1993); Cowan, D. B., et al., *J. Biol. Chem.* 268:26904–26910 (1993)). In HepG2 cells, oxidative stress induced by treatment with gramoxone resulted in a 10-fold increase in steady state levels of catalase mRNA and a 2-fold increase in levels of Cu/Zn superoxide dismutase mRNA. Consistent with the proposed mechanism of action of gramoxone, this response was eliminated by the addition of the free radical scavenger, dimethyl sulfoxide (Maitre, B., et al., *Am. J. Physiol.* 265:L635–L643 (1993)). In contrast, as demonstrated herein, gramoxone treatment decreased the steady state levels of apoAI mRNA 2-fold without affecting the levels of mRNAs for other major apolipoproteins such as apoB and apoE. This down-regulation of apoAI mRNA in response to oxidant treatment suggests that decreased apoAI synthesis may contribute to the observed reduction in plasma HDL seen in cigarette smokers (Haffner, S. M., et al., *Arteriosclerosis* 5:169–177 (1985); Assmann, G., et al., *J. Clin. Chem. & Clin. Biochem.* 22:397–402 (1984); Pryor, W. A., et al., *Environ. Health Perspect.* 47:345–355 (1983); Wilhelmsson, C., et al., *Lancet* 1:415–420 (1975)).

These studies demonstrate for the first time that oxidative stress may act by selectively decreasing hepatic apoAI mRNA levels. Although the molecular mechanisms by which gramoxone modulates apoAI are not completely understood, it has been shown that the 2-fold reduction in apoAI mRNA level results from a combination of a 4-fold increase in apoAI mRNA degradation and a 2-fold increase in apoAI gene transcription. This apparently paradoxical effect on mRNA synthesis and stability is not without precedent. For instance, apoAI gene transcription decreases during chronic hyperthyroidism while the hepatic abundance of apoAI increases 3-fold, by a mechanism that involves stabilization and/or more efficient processing of the nuclear apoAI mRNA precursors (Lin-Lee, Y- C., et al., *J. Lipid Res.* 34:249–259 (1993); Strobl, W., et al., *J. Clin. Invest.* 85:659–667 (1990)). This observation has prompted the suggestion that apoAI gene transcription may be subject to feedback regulation and that degradation of nuclear apoAI RNA could have a positive effect on apoAI gene transcription (Lin-Lee, Y- C., et al., *J. Lipid Res.* 34:249–259 (1993); Strobl, W., et al., *J. Clin. Invest.* 85:659–667 (1990)). While the suggestion remains a hypothesis, the data presented here are also consistent with the possibility that the increase in transcription is a compensatory response to the decrease in apoAI mRNA levels. In addition to the perturbations of thyroid horrnone status, dietary cholesterol and saturated fat can also affect apoAI gene expression at both transcriptional and post-transcriptional levels (Srivastava, R. A. K., et al., *Biochim. Biophys. Acta.* 1125:251–261 (1992); Sorci-Thomas, M., et al., *J. Biol. Chem.* 263:5183–5189 (1988); Go, M. F., et al., *J. Clin. Invest.* 81:1615–1620 (1988); Hayek, T., et al., *J. Clin. Invest.* 91:1665–1671 (1993); Azrolan, N., et al., *J. Biol. Chem.* 270:19833–19838 (1995)).

In addition to the proposed autoregulation of apoAI transcription described above, as demonstrated herein apoAI gene expression appears to be directly responsive to oxidative stress. The apoAI promoter comprises an ARE having a different sequence from the putative ARE of the rat GST Ya subunit gene and the rat NAD(P)H:quinone reductase genes (Rushmore, T. H., et al., *J. Biol. Chem.* 266:11632–11639 (1991); Favreau, L. V. and Pickett, C. B., *J. Biol. Chem.* 266:4556–4561 (1991)) (See FIG. 7). Band shift assays demonstrate that both untreated and gramoxone-treated HepG2 nuclear extracts comprise factors that bind specifically to the ARE and these factors can be induced by gramoxone treatment. The increase in protein-DNA complex formation was apparent within 1 h of gramoxone exposure and was not blocked by inhibiting protein synthesis, suggesting that the increased binding activity was attributable to modification of a pre-existing factor. UV cross-linking experiments identified two proteins with apparent molecular masses of approximately 100 and 115 kDa (FIG. 6A). Although present in control HepG2 nuclear extracts, gramoxone treatment resulted in an increase in binding of both proteins.

These data differ from a report by Nguyen and Pickett which indicates that proteins UV cross-linked to the GST-ARE have apparent molecular masses of approximately 28 and 45 kDa and that the DNA binding activity of these proteins are not increased by t-butylhydroquinone treatment in HepG2 cells (Nguyen, T. and Pickett, C. B., *J. Biol. Chem.* 267:13535–13539 (1992)). To examine this difference, UV cross-linking experiments were performed as described herein, using labelled GST-ARE as a probe together with either control or gramoxone-treated nuclear extracts. These results demonstrated four polypeptides (apparent molecular masses of 21, 28, 57 and 98 kDa) were cross-linked to the GST-ARE after UV irradiation (FIG. 6C). In contrast to apoAI-ARE UV cross-linked proteins, the DNA binding activity of these proteins was not increased by gramoxone treatment in HepG2 cells. The 28 and 57 kDa proteins may *1 correspond to the two species described by Pickett and co-workers (Nguyen, T. and Pickett, C. B., *J. Biol. Chem.* 267:13535–13539 (1992)). However, at present it is not clear why these investigators did not also observe the 21 and 98 kDa polypeptides. Although the 98 kDa protein cross-linked to the GST-ARE has a very similar size to the smaller and more predominant species cross-linked to the apoAI-ARE, the lack of inducibility of the 98 kDa protein by gramoxone treatment suggests that these two proteins are different. This suggestion is supported by competition band-shift experiments which also indicate differences between the protein binding to the apo Al-ARE and the GST-ARE (FIGS. 5A and B).

Transient transfection experiments using pGL2-P-derived luciferase reporter plasmids confirmed a functional role for the ARE in apoAI gene transcription in response to gramoxone. Constructs which comprise nucleotides −491 to +1 and −250 to +1 upstream from the transcription start site (+1) of the human apoAI gene show a significant 2-fold increase in luciferase activity in the presence of gramoxone (FIG. 4). The involvement of the ARE in gramoxone-mediated induction of apoAI gene expression was demonstrated by using plasmid PGL2 (apoAI -250 mutant ARE) in which the consensus ARE was eliminated by multiple point mutations. Results from these studies indicated that this construct had lost gramoxone inducibility.

In addition, it was also examined whether or not the ARE could function independently as a regulatory element using a heterologous promoter. These studies demonstrated that the plasmids pGL2P (apoAI-ARE)/luc and pGL2P(GST-ARE)/luc, where one copy of either the apoAI-ARE or the GST-ARE was inserted upstream of the SV40 promoter, conferred gramoxone inducibility. However, a plasmid comprising one copy of the mutated apoAI-ARE pGL2P (apoAI mutated ARE)/luc displayed no response to gramoxone treatment. These data indicate that the ARE located in the apoAI promoter region can function independently as a bonafide regulatory element that is responsive to oxidative stress.

All of the above experiments (examples 1 to 6) have also been carried out using Hep3B cells as well as HH02, a long term culture of non-transformed human hepatocytes (kindly provided by Dr. Eve Roberts, Hospital for Sick Children, Toronto). Similar results were observed when Hep3B and HH02 cells were utilized. Initially, two human hepatoma cell lines, HepG2 and Hep3B, which have provided the best human in vitro hepatic models available to date, were utilized, as described herein, to investigate molecular mechanisms by which oxidative stress modulates HDL synthesis. Because these cells are derived from a human hepatoblastoma, they could possess different features from those of human hepatocytes in vivo. Consequently, the above observations were confirmed using HH02 cells to minimize the possibility that the response of HepG2 and Hep3B cells is due to their malignant phenotype.

In summary, gramoxone-inducible nuclear proteins were identified which bind specifically to the ARE region of the human apoAI gene. These protein-DNA interactions appear to be involved in the mechanism by which oxidant or antioxidant-inducible trans-acting nuclear factors modulate apoAI gene transcription. Taken together, this data demonstrate that gramoxone affects hepatic apoAI mRNA abundance by both transcriptional and post-transcriptional mechanisms.

The abbreviations used are: apoAI, apolipoprotein AI; ARE, antioxidant response element; DMSO, dimethyl sulfoxide; FBS, fetal bovine serum; GST, glutathione S-transferase; HDL, high density lipoprotein; LDL, low density lipoprotein; MEM, minimal essential medium; PBS, phosphate buffered saline; SDS, sodium dodecyl sulfate; XRE, xenobiotic response element.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A method of screening for a compound that increases transcription of an mRNA regulated by an antioxidant responsive element, comprising:

(a) assaying a first cellular extract for the amount of product from transcription of said mRNA wherein said mRNA is expressed from a DNA construct, said transcription being in the absence of a candidate compound and said DNA construct comprising:

an antioxidant responsive element (ARE) having a DNA sequence 5'-RGR AC NNN GCT-3' (SEQ ID NO:1) operably linked to a protein coding sequence;

(b) assaying a second cellular extract for the amount of product from transcription of said mRNA wherein said mRNA is expressed from said DNA construct, said transcription being in the presence of said candidate compound; and (c) comparing th e amounts of products from transcription of said first extract and said second extract, wherein a greater amount of product from transcription in said second extract as compared to said first extract indicates that said candidate compound increases transcription of said mRNA regulated by said antioxidant responsive element.

2. The method according to claim 1, wherein said protein coding sequence is a heterologous protein coding sequence.

3. The method according to claim 1, wherein said protein coding sequence is a reporter gene.

4. The method according to claim 1, wherein said DNA construct further comprises an untranslated region including a functional polyadenylation signal.

5. The method according to claim 1, wherein said ARE has the sequence 5'-GGGACNNNGCT-3' (SEQ ID NO:2).

6. The method according to claim 1, wherein said ARE has the sequence 5'-GGGACAGAGCT-3' (SEQ ID NO:3).

7. The method of claim 1, wherein said product from transcription is mRNA.

8. The method of claim 1, wherein said product from transcription is protein.

* * * * *

```
SEQUENCE LISTING

(1) GENERAL INFORMATION:

   (iii) NUMBER OF SEQUENCES: 51


(2) INFORMATION FOR SEQ ID NO:1:

     (i) SEQUENCE CHARACTERISTICS:
          (A) LENGTH: 11 base pairs
          (B) TYPE: nucleic acid
          (C) STRANDEDNESS: single
          (D) TOPOLOGY: linear
```

-continued (xi) SEQUENCE DESCRIPTION: SEQ ID NO:1:

RGRACNNNGC T 11

(2) INFORMATION FOR SEQ ID NO:2:

(i) SEQUENCE CHARACTERISTICS:
(A) LENGTH: 11 base pairs
(B) TYPE: nucleic acid
(C) STRANDEDNESS: single
(D) TOPOLOGY: linear (xi) SEQUENCE DESCRIPTION: SEQ ID NO:2:

GGGACNNNGC T 11

(2) INFORMATION FOR SEQ ID NO:3:

(i) SEQUENCE CHARACTERISTICS:
(A) LENGTH: 11 base pairs
(B) TYPE: nucleic acid
(C) STRANDEDNESS: single
(D) TOPOLOGY: linear (xi) SEQUENCE DESCRIPTION: SEQ ID NO:3:

GGGACAGAGC T 11

(2) INFORMATION FOR SEQ ID NO:4:

(i) SEQUENCE CHARACTERISTICS:
(A) LENGTH: 11 base pairs
(B) TYPE: nucleic acid
(C) STRANDEDNESS: single
(D) TOPOLOGY: linear (xi) SEQUENCE DESCRIPTION: SEQ ID NO:4:

RGGACNNNGC T 11

(2) INFORMATION FOR SEQ ID NO:5:

(i) SEQUENCE CHARACTERISTICS:
(A) LENGTH: 11 base pairs
(B) TYPE: nucleic acid
(C) STRANDEDNESS: single
(D) TOPOLOGY: linear (xi) SEQUENCE DESCRIPTION: SEQ ID NO:5:

GGRACNNNGC T 11

(2) INFORMATION FOR SEQ ID NO:6:

(i) SEQUENCE CHARACTERISTICS:
(A) LENGTH: 11 base pairs
(B) TYPE: nucleic acid
(C) STRANDEDNESS: single
(D) TOPOLOGY: linear (xi) SEQUENCE DESCRIPTION: SEQ ID NO:6:

RRGRACNNNG C 11

(2) INFORMATION FOR SEQ ID NO:7:

(i) SEQUENCE CHARACTERISTICS:
(A) LENGTH: 12 base pairs
(B) TYPE: nucleic acid
(C) STRANDEDNESS: single
(D) TOPOLOGY: linear -continued (xi) SEQUENCE DESCRIPTION: SEQ ID NO:7:

RRGRACNNNG CT 12

(2) INFORMATION FOR SEQ ID NO:8:

(i) SEQUENCE CHARACTERISTICS:
(A) LENGTH: 12 base pairs
(B) TYPE: nucleic acid
(C) STRANDEDNESS: single
(D) TOPOLOGY: linear (xi) SEQUENCE DESCRIPTION: SEQ ID NO:8:

YRRGRACNNN GC 12

(2) INFORMATION FOR SEQ ID NO:9:

(i) SEQUENCE CHARACTERISTICS:
(A) LENGTH: 13 base pairs
(B) TYPE: nucleic acid
(C) STRANDEDNESS: single
(D) TOPOLOGY: linear (xi) SEQUENCE DESCRIPTION: SEQ ID NO:9:

YRRGRACNNN GCT 13

(2) INFORMATION FOR SEQ ID NO:10:

(i) SEQUENCE CHARACTERISTICS:
(A) LENGTH: 11 base pairs
(B) TYPE: nucleic acid
(C) STRANDEDNESS: single
(D) TOPOLOGY: linear (xi) SEQUENCE DESCRIPTION: SEQ ID NO:10:

AGGGACAGAG C 11

(2) INFORMATION FOR SEQ ID NO:11:

(i) SEQUENCE CHARACTERISTICS:
(A) LENGTH: 12 base pairs
(B) TYPE: nucleic acid
(C) STRANDEDNESS: single
(D) TOPOLOGY: linear (xi) SEQUENCE DESCRIPTION: SEQ ID NO:11:

AGGGACAGAG CT 12

(2) INFORMATION FOR SEQ ID NO:12:

(i) SEQUENCE CHARACTERISTICS:
(A) LENGTH: 12 base pairs
(B) TYPE: nucleic acid
(C) STRANDEDNESS: single
(D) TOPOLOGY: linear (xi) SEQUENCE DESCRIPTION: SEQ ID NO:12:

CAGGGACAGA GC 12

(2) INFORMATION FOR SEQ ID NO:13:

(i) SEQUENCE CHARACTERISTICS:
(A) LENGTH: 13 base pairs
(B) TYPE: nucleic acid
(C) STRANDEDNESS: single
(D) TOPOLOGY: linear (xi) SEQUENCE DESCRIPTION: SEQ ID NO:13:

-continued

CAGGGACAGA GCT 13

(2) INFORMATION FOR SEQ ID NO:14:

(i) SEQUENCE CHARACTERISTICS:
(A) LENGTH: 11 base pairs
(B) TYPE: nucleic acid
(C) STRANDEDNESS: single
(D) TOPOLOGY: linear (xi) SEQUENCE DESCRIPTION: SEQ ID NO:14:

AGGACAGAGC T 11

(2) INFORMATION FOR SEQ ID NO:15:

(i) SEQUENCE CHARACTERISTICS:
(A) LENGTH: 11 base pairs
(B) TYPE: nucleic acid
(C) STRANDEDNESS: single
(D) TOPOLOGY: linear (xi) SEQUENCE DESCRIPTION: SEQ ID NO:15:

AAGGACAGAG C 11

(2) INFORMATION FOR SEQ ID NO:16:

(i) SEQUENCE CHARACTERISTICS:
(A) LENGTH: 12 base pairs
(B) TYPE: nucleic acid
(C) STRANDEDNESS: single
(D) TOPOLOGY: linear (xi) SEQUENCE DESCRIPTION: SEQ ID NO:16:

AAGGACAGAG CT 12

(2) INFORMATION FOR SEQ ID NO:17:

(i) SEQUENCE CHARACTERISTICS:
(A) LENGTH: 12 base pairs
(B) TYPE: nucleic acid
(C) STRANDEDNESS: single
(D) TOPOLOGY: linear (xi) SEQUENCE DESCRIPTION: SEQ ID NO:17:

CAAGGACAGA GC 12

(2) INFORMATION FOR SEQ ID NO:18:

(i) SEQUENCE CHARACTERISTICS:
(A) LENGTH: 11 base pairs
(B) TYPE: nucleic acid
(C) STRANDEDNESS: single
(D) TOPOLOGY: linear (xi) SEQUENCE DESCRIPTION: SEQ ID NO:18:

GGGACAAAGC T 11

(2) INFORMATION FOR SEQ ID NO:19:

(i) SEQUENCE CHARACTERISTICS:
(A) LENGTH: 12 base pairs
(B) TYPE: nucleic acid
(C) STRANDEDNESS: single
(D) TOPOLOGY: linear (xi) SEQUENCE DESCRIPTION: SEQ ID NO:19:

-continued

AGGGACAAAG CT 12

(2) INFORMATION FOR SEQ ID NO:20:

(i) SEQUENCE CHARACTERISTICS:
(A) LENGTH: 13 base pairs
(B) TYPE: nucleic acid
(C) STRANDEDNESS: single
(D) TOPOLOGY: linear (xi) SEQUENCE DESCRIPTION: SEQ ID NO:20:

CAGGGACAAA GCT 13

(2) INFORMATION FOR SEQ ID NO:21:

(i) SEQUENCE CHARACTERISTICS:
(A) LENGTH: 11 base pairs
(B) TYPE: nucleic acid
(C) STRANDEDNESS: single
(D) TOPOLOGY: linear (xi) SEQUENCE DESCRIPTION: SEQ ID NO:21:

GGAACAGAGC T 11

(2) INFORMATION FOR SEQ ID NO:22:

(i) SEQUENCE CHARACTERISTICS:
(A) LENGTH: 12 base pairs
(B) TYPE: nucleic acid
(C) STRANDEDNESS: single
(D) TOPOLOGY: linear (xi) SEQUENCE DESCRIPTION: SEQ ID NO:22:

GGGAACAGAG CT 12

(2) INFORMATION FOR SEQ ID NO:23:

(i) SEQUENCE CHARACTERISTICS:
(A) LENGTH: 13 base pairs
(B) TYPE: nucleic acid
(C) STRANDEDNESS: single
(D) TOPOLOGY: linear (xi) SEQUENCE DESCRIPTION: SEQ ID NO:23:

CGGGAACAGA GCT 13

(2) INFORMATION FOR SEQ ID NO:24:

(i) SEQUENCE CHARACTERISTICS:
(A) LENGTH: 12 base pairs
(B) TYPE: nucleic acid
(C) STRANDEDNESS: single
(D) TOPOLOGY: linear (xi) SEQUENCE DESCRIPTION: SEQ ID NO:24:

AGGAACAGAG CT 12

(2) INFORMATION FOR SEQ ID NO:25:

(i) SEQUENCE CHARACTERISTICS:
(A) LENGTH: 13 base pairs
(B) TYPE: nucleic acid
(C) STRANDEDNESS: single
(D) TOPOLOGY: linear (xi) SEQUENCE DESCRIPTION: SEQ ID NO:25:

CAGGAACAGA GCT 13

-continued (2) INFORMATION FOR SEQ ID NO:26:

(i) SEQUENCE CHARACTERISTICS:
(A) LENGTH: 6092 base pairs
(B) TYPE: nucleic acid
(C) STRANDEDNESS: double
(D) TOPOLOGY: circular (xi) SEQUENCE DESCRIPTION: SEQ ID NO:26:

CCCGGGAGGT ACCGAGCTCT TACGCGTGCT AGCTCGGAGG CCTGAGGACC TGCTGGGGAC 60

TAAAGAAGAG CACTGGTGGG AGGACAGGGC GGGGGAAGGG GGAGGGGAGT GAAGTAGTCT 120

CCCTGGAATG CTGGTGGTGG GGGAGGCAGT CTCCTTGGTG GAGGAGTCCC AGCGTCCCTC 180

CCCTCCCCTC CTCTGCCAAC ACAATGGACA ATGGCAACTG CCCACACACT CCCATGGAGG 240

GGAAGGGGAT GAGTGCAGGG AACCCCGACC CCACCCGGGA GACCTGCAAG CCTGCAGACA 300

CTCCCCTCCC GCCCCCACTG AACCCTTGAC CCCTGCCCTG CAGCCCCCGC AGCTTGCTGT 360

TTGCCCACTC TATTTGCCCA GCCCCAGGGA CAGAGCTGAT CCTTGAACTC TTAAGTTCCA 420

CATTGCCAGG ACCAGTGAGC AGCAACAGGG CCGGGGCTGG CTTATCAGCC TCCCAGCCCA 480

GACCCTGGCT GCAGACATAA ATAGGCCCTG CAAGAGCTGG CTGCTTAGTC GAGATCTAAG 540

TAAGCTTGGC ATTCCGGTAC TGTTGGTAAA ATGGAAGACG CCAAAAACAT AAAGAAAGGC 600

CCGGCGCCAT TCTATCCTCT AGAGGATGGA ACCGCTGGAG AGCAACTGCA TAAGGCTATG 660

AAGAGATACG CCCTGGTTCC TGGAACAATT GCTTTTACAG ATGCACATAT CGAGGTGAAC 720

ATCACGTACG CGGAATACTT CGAAATGTCC GTTCGGTTGG CAGAAGCTAT GAAACGATAT 780

GGGCTGAATA CAAATCACAG AATCGTCGTA TGCAGTGAAA ACTCTCTTCA ATTCTTTATG 840

CCGGTGTTGG GCGCGTTATT TATCGGAGTT GCAGTTGCGC CCGCGAACGA CATTTATAAT 900

GAACGTGAAT TGCTCAACAG TATGAACATT TCGCAGCCTA CCGTAGTGTT TGTTTCCAAA 960

AAGGGGTTGC AAAAAATTTT GAACGTGCAA AAAAAATTAC CAATAATCCA GAAAATTATT 1020

ATCATGGATT CTAAAACGGA TTACCAGGGA TTTCAGTCGA TGTACACGTT CGTCACATCT 1080

CATCTACCTC CCGGTTTTAA TGAATACGAT TTTGTACCAG AGTCCTTTGA TCGTGACAAA 1140

ACAATTGCAC TGATAATGAA TTCCTCTGGA TCTACTGGGT TACCTAAGGG TGTGGCCCTT 1200

CCGCATAGAA CTGCCTGCGT CAGATTCTCG CATGCCAGAG ATCCTATTTT TGGCAATCAA 1260

ATCATTCCGG ATACTGCGAT TTTAAGTGTT GTTCCATTCC ATCACGGTTT TGGAATGTTT 1320

ACTACACTCG GATATTTGAT ATGTGGATTT CGAGTCGTCT TAATGTATAG ATTTGAAGAA 1380

GAGCTGTTTT TACGATCCCT TCAGGATTAC AAAATTCAAA GTGCGTTGCT AGTACCAACC 1440

CTATTTTCAT TCTTCGCCAA AAGCACTCTG ATTGACAAAT ACGATTTATC TAATTTACAC 1500

GAAATTGCTT CTGGGGGCGC ACCTCTTTCG AAAGAAGTCG GGGAAGCGGT TGCAAAACGC 1560

TTCCATCTTC CAGGGATACG ACAAGGATAT GGGCTCACTG AGACTACATC AGCTATTCTG 1620

ATTACACCCG AGGGGGATGA TAAACCGGGC GCGGTCGGTA AAGTTGTTCC ATTTTTTGAA 1680

GCGAAGGTTG TGGATCTGGA TACCGGGAAA ACGCTGGGCG TTAATCAGAG AGGCGAATTA 1740

TGTGTCAGAG GACCTATGAT TATGTCCGGT TATGTAAACA ATCCGGAAGC GACCAACGCC 1800

TTGATTGACA AGGATGGATG GCTACATTCT GGAGACATAG CTTACTGGGA CGAAGACGAA 1860

CACTTCTTCA TAGTTGACCG CTTGAAGTCT TTAATTAAAT ACAAAGGATA TCAGGTGGCC 1920

CCCGCTGAAT TGGAATCGAT ATTGTTACAA CACCCCAACA TCTTCGACGC GGGCGTGGCA 1980

GGTCTTCCCG ACGATGACGC CGGTGAACTT CCCGCCGCCG TTGTTGTTTT GGAGCACGGA 2040

-continued

```
AAGACGATGA CGGAAAAAGA GATCGTGGAT TACGTCGCCA GTCAAGTAAC AACCGCGAAA   2100
AAGTTGCGCG GAGGAGTTGT GTTTGTGGAC GAAGTACCGA AAGGTCTTAC CGGAAAACTC   2160
GACGCAAGAA AAATCAGAGA GATCCTCATA AAGGCCAAGA AGGGCGGAAA GTCCAAATTG   2220
TAAAATGTAA CTGTATTCAG CGATGACGAA ATTCTTAGCT ATTGTAATAC TGCGATGAGT   2280
GGCAGGGCGG GGCGTAATTT TTTTAAGGCA GTTATTGGTG CCCTTAAACG CCTGGTGCTA   2340
CGCCTGAATA AGTGATAATA AGCGGATGAA TGGCAGAAAT TCGCCGGATC TTTGTGAAGG   2400
AACCTTACTT CTGTGGTGTG ACATAATTGG ACAAACTACC TACAGAGATT TAAAGCTCTA   2460
AGGTAAATAT AAAATTTTTA AGTGTATAAT GTGTTAAACT ACTGATTCTA ATTGTTTGTG   2520
TATTTTAGAT TCCAACCTAT GGAACTGATG AATGGGAGCA GTGGTGGAAT GCCTTTAATG   2580
AGGAAAACCT GTTTTGCTCA GAAGAAATGC CATCTAGTGA TGATGAGGCT ACTGCTGACT   2640
CTCAACATTC TACTCCTCCA AAAAAGAAGA GAAAGGTAGA AGACCCCAAG GACTTTCCTT   2700
CAGAATTGCT AAGTTTTTTG AGTCATGCTG TGTTTAGTAA TAGAACTCTT GCTTGCTTTG   2760
CTATTTACAC CACAAAGGAA AAAGCTGCAC TGCTATACAA GAAAATTATG GAAAAATATT   2820
CTGTAACCTT TATAAGTAGG CATAACAGTT ATAATCATAA CATACTGTTT TTTCTTACTC   2880
CACACAGGCA TAGAGTGTCT GCTATTAATA ACTATGCTCA AAAATTGTGT ACCTTTAGCT   2940
TTTTAATTTG TAAAGGGGTT AATAAGGAAT ATTTGATGTA TAGTGCCTTG ACTAGAGATC   3000
ATAATCAGCC ATACCACATT TGTAGAGGTT TTACTTGCTT TAAAAAACCT CCCACACCTC   3060
CCCCTGAACC TGAAACATAA AATGAATGCA ATTGTTGTTG TTAACTTGTT TATTGCAGCT   3120
TATAATGGTT ACAAATAAAG CAATAGCATC ACAAATTTCA CAAATAAAGC ATTTTTTTCA   3180
CTGCATTCTA GTTGTGGTTT GTCCAAACTC ATCAATGTAT CTTATCATGT CTGGATCCGT   3240
CGACCGATGC CCTTGAGAGC CTTCAACCCA GTCAGCTCCT TCCGGTGGGC GCGGGGCATG   3300
ACTATCGTCG CCGCACTTAT GACTGTCTTC TTTATCATGC AACTCGTAGG ACAGGTGCCG   3360
GCAGCGCTCT TCCGCTTCCT CGCTCACTGA CTCGCTGCGC TCGGTCGTTC GGCTGCGGCG   3420
AGCGGTATCA GCTCACTCAA AGGCGGTAAT ACGGTTATCC ACAGAATCAG GGGATAACGC   3480
AGGAAAGAAC ATGTGAGCAA AAGGCCAGCA AAAGGCCAGG AACCGTAAAA AGGCCGCGTT   3540
GCTGGCGTTT TTCCATAGGC TCCGCCCCCC TGACGAGCAT CACAAAAATC GACGCTCAAG   3600
TCAGAGGTGG CGAAACCCGA CAGGACTATA AAGATACCAG GCGTTTCCCC CTGGAAGCTC   3660
CCTCGTGCGC TCTCCTGTTC CGACCCTGCC GCTTACCGGA TACCTGTCCG CCTTTCTCCC   3720
TTCGGGAAGC GTGGCGCTTT CTCAATGCTC ACGCTGTAGG TATCTCAGTT CGGTGTAGGT   3780
CGTTCGCTCC AAGCTGGGCT GTGTGCACGA ACCCCCCGTT CAGCCCGACC GCTGCGCCTT   3840
ATCCGGTAAC TATCGTCTTG AGTCCAACCC GGTAAGACAC GACTTATCGC CACTGGCAGC   3900
AGCCACTGGT AACAGGATTA GCAGAGCGAG GTATGTAGGC GGTGCTACAG AGTTCTTGAA   3960
GTGGTGGCCT AACTACGGCT ACACTAGAAG GACAGTATTT GGTATCTGCG CTCTGCTGAA   4020
GCCAGTTACC TTCGGAAAAA GAGTTGGTAG CTCTTGATCC GGCAAACAAA CCACCGCTGG   4080
TAGCGGTGGT TTTTTTGTTT GCAAGCAGCA GATTACGCGC AGAAAAAAAG GATCTCAAGA   4140
AGATCCTTTG ATCTTTTCTA CGGGGTCTGA CGCTCAGTGG AACGAAAACT CACGTTAAGG   4200
GATTTTGGTC ATGAGATTAT CAAAAAGGAT CTTCACCTAG ATCCTTTTAA ATTAAAAATG   4260
AAGTTTTAAA TCAATCTAAA GTATATATGA GTAAACTTGG TCTGACAGTT ACCAATGCTT   4320
AATCAGTGAG GCACCTATCT CAGCGATCTG TCTATTTCGT TCATCCATAG TTGCCTGACT   4380
```

-continued

```
CCCCGTCGTG TAGATAACTA CGATACGGGA GGGCTTACCA TCTGGCCCCA GTGCTGCAAT   4440

GATACCGCGA GACCCACGCT CACCGGCTCC AGATTTATCA GCAATAAACC AGCCAGCCGG   4500

AAGGGCCGAG CGCAGAAGTG GTCCTGCAAC TTTATCCGCC TCCATCCAGT CTATTAATTG   4560

TTGCCGGGAA GCTAGAGTAA GTAGTTCGCC AGTTAATAGT TTGCGCAACG TTGTTGCCAT   4620

TGCTACAGGC ATCGTGGTGT CACGCTCGTC GTTTGGTATG GCTTCATTCA GCTCCGGTTC   4680

CCAACGATCA AGGCGAGTTA CATGATCCCC CATGTTGTGC AAAAAAGCGG TTAGCTCCTT   4740

CGGTCCTCCG ATCGTTGTCA GAAGTAAGTT GGCCGCAGTG TTATCACTCA TGGTTATGGC   4800

AGCACTGCAT AATTCTCTTA CTGTCATGCC ATCCGTAAGA TGCTTTTCTG TGACTGGTGA   4860

GTACTCAACC AAGTCATTCT GAGAATAGTG TATGCGGCGA CCGAGTTGCT CTTGCCCGGC   4920

GTCAATACGG GATAATACCG CGCCACATAG CAGAACTTTA AAAGTGCTCA TCATTGGAAA   4980

ACGTTCTTCG GGGCGAAAAC TCTCAAGGAT CTTACCGCTG TTGAGATCCA GTTCGATGTA   5040

ACCCACTCGT GCACCCAACT GATCTTCAGC ATCTTTTACT TTCACCAGCG TTTCTGGGTG   5100

AGCAAAAACA GGAAGGCAAA ATGCCGCAAA AAAGGGAATA AGGGCGACAC GGAAATGTTG   5160

AATACTCATA CTCTTCCTTT TTCAATATTA TTGAAGCATT TATCAGGGTT ATTGTCTCAT   5220

GAGCGGATAC ATATTTGAAT GTATTTAGAA AAATAAACAA ATAGGGGTTC CGCGCACATT   5280

TCCCCGAAAA GTGCCACCTG ACGCGCCCTG TAGCGGCGCA TTAAGCGCGG CGGGTGTGGT   5340

GGTTACGCGC AGCGTGACCG CTACACTTGC CAGCGCCCTA GCGCCCGCTC CTTTCGCTTT   5400

CTTCCCTTCC TTTCTCGCCA CGTTCGCCGG CTTTCCCCGT CAAGCTCTAA ATCGGGGGCT   5460

CCCTTTAGGG TTCCGATTTA GTGCTTTACG GCACCTCGAC CCCAAAAAAC TTGATTAGGG   5520

TGATGGTTCA CGTAGTGGGC CATCGCCCTG ATAGACGGTT TTTCGCCCTT TGACGTTGGA   5580

GTCCACGTTC TTTAATAGTG GACTCTTGTT CCAAACTGGA ACAACACTCA ACCCTATCTC   5640

GGTCTATTCT TTTGATTTAT AAGGGATTTT GCCGATTTCG GCCTATTGGT TAAAAAATGA   5700

GCTGATTTAA CAAAAATTTA ACGCGAATTT TAACAAAATA TTAACGTTTA CAATTTCCCA   5760

TTCGCCATTC AGGCTGCGCA ACTGTTGGGA AGGGCGATCG GTGCGGGCCT CTTCGCTATT   5820

ACGCCAGCCC AAGCTACCAT GATAAGTAAG TAATATTAAG GTACGTGGAG GTTTTACTTG   5880

CTTTAAAAAA CCTCCCACAC CTCCCCCTGA ACCTGAAACA TAAAATGAAT GCAATTGTTG   5940

TTGTTAACTT GTTTATTGCA GCTTATAATG GTTACAAATA AAGCAATAGC ATCACAAATT   6000

TCACAAATAA AGCATTTTTT TCACTGCATT CTAGTTGTGG TTTGTCCAAA CTCATCAATG   6060

TATCTTATGG TACTGTAACT GAGCTAACAT AA                                 6092
```

(2) INFORMATION FOR SEQ ID NO:27:

(i) SEQUENCE CHARACTERISTICS:
(A) LENGTH: 5819 base pairs
(B) TYPE: nucleic acid
(C) STRANDEDNESS: double
(D) TOPOLOGY: circular (xi) SEQUENCE DESCRIPTION: SEQ ID NO:27:

```
CCCGGGAGAC CTGCAAGCCT GCAGACACTC CCCTCCCGCC CCCACTGAAC CCTTGACCCC     60

TGCCCTGCAG CCCCCGCAGC TTGCTGTTTG CCCACTCTAT TTGCCCAGCC CCAGGGACAG    120

AGCTGATCCT TGAACTCTTA AGTTCCACAT TGCCAGGACC AGTGAGCAGC AACAGGGCCG    180

GGGCTGGCTT ATCAGCCTCC CAGCCCAGAC CCTGGCTGCA GACATAAATA GGCCCTGCAA    240

GAGCTGGCTG CTTAGTCGAG ATCTAAGTAA GCTTGGCATT CCGGTACTGT TGGTAAAATG    300
```

-continued

```
GAAGACGCCA AAAACATAAA GAAAGGCCCG GCGCCATTCT ATCCTCTAGA GGATGGAACC    360
GCTGGAGAGC AACTGCATAA GGCTATGAAG AGATACGCCC TGGTTCCTGG AACAATTGCT    420
TTTACAGATG CACATATCGA GGTGAACATC ACGTACGCGG AATACTTCGA AATGTCCGTT    480
CGGTTGGCAG AAGCTATGAA ACGATATGGG CTGAATACAA ATCACAGAAT CGTCGTATGC    540
AGTGAAAACT CTCTTCAATT CTTTATGCCG GTGTTGGGCG CGTTATTTAT CGGAGTTGCA    600
GTTGCGCCCG CGAACGACAT TTATAATGAA CGTGAATTGC TCAACAGTAT GAACATTTCG    660
CAGCCTACCG TAGTGTTTGT TTCCAAAAAG GGGTTGCAAA AAATTTTGAA CGTGCAAAAA    720
AAATTACCAA TAATCCAGAA AATTATTATC ATGGATTCTA AAACGGATTA CCAGGGATTT    780
CAGTCGATGT ACACGTTCGT CACATCTCAT CTACCTCCCG GTTTTAATGA ATACGATTTT    840
GTACCAGAGT CCTTTGATCG TGACAAAACA ATTGCACTGA TAATGAATTC CTCTGGATCT    900
ACTGGGTTAC CTAAGGGTGT GGCCCTTCCG CATAGAACTG CCTGCGTCAG ATTCTCGCAT    960
GCCAGAGATC CTATTTTTGG CAATCAAATC ATTCCGGATA CTGCGATTTT AAGTGTTGTT   1020
CCATTCCATC ACGGTTTTGG AATGTTTACT ACACTCGGAT ATTTGATATG TGGATTTCGA   1080
GTCGTCTTAA TGTATAGATT TGAAGAAGAG CTGTTTTTAC GATCCCTTCA GGATTACAAA   1140
ATTCAAAGTG CGTTGCTAGT ACCAACCCTA TTTTCATTCT TCGCCAAAAG CACTCTGATT   1200
GACAAATACG ATTTATCTAA TTTACACGAA ATTGCTTCTG GGGGCGCACC TCTTTCGAAA   1260
GAAGTCGGGG AAGCGGTTGC AAAACGCTTC CATCTTCCAG GGATACGACA AGGATATGGG   1320
CTCACTGAGA CTACATCAGC TATTCTGATT ACACCCGAGG GGGATGATAA ACCGGGCGCG   1380
GTCGGTAAAG TTGTTCCATT TTTTGAAGCG AAGGTTGTGG ATCTGGATAC CGGGAAAACG   1440
CTGGGCGTTA ATCAGAGAGG CGAATTATGT GTCAGAGGAC CTATGATTAT GTCCGGTTAT   1500
GTAAACAATC CGGAAGCGAC CAACGCCTTG ATTGACAAGG ATGGATGGCT ACATTCTGGA   1560
GACATAGCTT ACTGGGACGA AGACGAACAC TTCTTCATAG TTGACCGCTT GAAGTCTTTA   1620
ATTAAATACA AAGGATATCA GGTGGCCCCC GCTGAATTGG AATCGATATT GTTACAACAC   1680
CCCAACATCT TCGACGCGGG CGTGGCAGGT CTTCCCGACG ATGACGCCGG TGAACTTCCC   1740
GCCGCCGTTG TTGTTTTGGA GCACGGAAAG ACGATGACGG AAAAAGAGAT CGTGGATTAC   1800
GTCGCCAGTC AAGTAACAAC CGCGAAAAAG TTGCGCGGAG GAGTTGTGTT TGTGGACGAA   1860
GTACCGAAAG GTCTTACCGG AAAACTCGAC GCAAGAAAAA TCAGAGAGAT CCTCATAAAG   1920
GCCAAGAAGG GCGGAAAGTC CAAATTGTAA AATGTAACTG TATTCAGCGA TGACGAAATT   1980
CTTAGCTATT GTAATACTGC GATGAGTGGC AGGGCGGGGC GTAATTTTTT TAAGGCAGTT   2040
ATTGGTGCCC TTAAACGCCT GGTGCTACGC CTGAATAAGT GATAATAAGC GGATGAATGG   2100
CAGAAATTCG CCGGATCTTT GTGAAGGAAC CTTACTTCTG TGGTGTGACA TAATTGGACA   2160
AACTACCTAC AGAGATTTAA AGCTCTAAGG TAAATATAAA ATTTTTAAGT GTATAATGTG   2220
TTAAACTACT GATTCTAATT GTTTGTGTAT TTTAGATTCC AACCTATGGA ACTGATGAAT   2280
GGGAGCAGTG GTGGAATGCC TTTAATGAGG AAAACCTGTT TTGCTCAGAA GAAATGCCAT   2340
CTAGTGATGA TGAGGCTACT GCTGACTCTC AACATTCTAC TCCTCCAAAA AAGAAGAGAA   2400
AGGTAGAAGA CCCCAAGGAC TTTCCTTCAG AATTGCTAAG TTTTTTGAGT CATGCTGTGT   2460
TTAGTAATAG AACTCTTGCT TGCTTTGCTA TTTACACCAC AAAGGAAAAA GCTGCACTGC   2520
TATACAAGAA AATTATGGAA AAATATTCTG TAACCTTTAT AAGTAGGCAT AACAGTTATA   2580
ATCATAACAT ACTGTTTTTT CTTACTCCAC ACAGGCATAG AGTGTCTGCT ATTAATAACT   2640
ATGCTCAAAA ATTGTGTACC TTTAGCTTTT TAATTTGTAA AGGGGTTAAT AAGGAATATT   2700
```

-continued

TGATGTATAG TGCCTTGACT AGAGATCATA ATCAGCCATA CCACATTTGT AGAGGTTTTA 2760

CTTGCTTTAA AAAACCTCCC ACACCTCCCC CTGAACCTGA AACATAAAAT GAATGCAATT 2820

GTTGTTGTTA ACTTGTTTAT TGCAGCTTAT AATGGTTACA AATAAAGCAA TAGCATCACA 2880

AATTTCACAA ATAAAGCATT TTTTTCACTG CATTCTAGTT GTGGTTTGTC CAAACTCATC 2940

AATGTATCTT ATCATGTCTG GATCCGTCGA CCGATGCCCT TGAGAGCCTT CAACCCAGTC 3000

AGCTCCTTCC GGTGGGCGCG GGGCATGACT ATCGTCGCCG CACTTATGAC TGTCTTCTTT 3060

ATCATGCAAC TCGTAGGACA GGTGCCGGCA GCGCTCTTCC GCTTCCTCGC TCACTGACTC 3120

GCTGCGCTCG GTCGTTCGGC TGCGGCGAGC GGTATCAGCT CACTCAAAGG CGGTAATACG 3180

GTTATCCACA GAATCAGGGG ATAACGCAGG AAAGAACATG TGAGCAAAAG GCCAGCAAAA 3240

GGCCAGGAAC CGTAAAAAGG CCGCGTTGCT GGCGTTTTTC CATAGGCTCC GCCCCCCTGA 3300

CGAGCATCAC AAAAATCGAC GCTCAAGTCA GAGGTGGCGA AACCCGACAG GACTATAAAG 3360

ATACCAGGCG TTTCCCCCTG GAAGCTCCCT CGTGCGCTCT CCTGTTCCGA CCCTGCCGCT 3420

TACCGGATAC CTGTCCGCCT TTCTCCCTTC GGGAAGCGTG GCGCTTTCTC AATGCTCACG 3480

CTGTAGGTAT CTCAGTTCGG TGTAGGTCGT TCGCTCCAAG CTGGGCTGTG TGCACGAACC 3540

CCCCGTTCAG CCCGACCGCT GCGCCTTATC CGGTAACTAT CGTCTTGAGT CCAACCCGGT 3600

AAGACACGAC TTATCGCCAC TGGCAGCAGC CACTGGTAAC AGGATTAGCA GAGCGAGGTA 3660

TGTAGGCGGT GCTACAGAGT TCTTGAAGTG GTGGCCTAAC TACGGCTACA CTAGAAGGAC 3720

AGTATTTGGT ATCTGCGCTC TGCTGAAGCC AGTTACCTTC GGAAAAAGAG TTGGTAGCTC 3780

TTGATCCGGC AAACAAACCA CCGCTGGTAG CGGTGGTTTT TTTGTTTGCA AGCAGCAGAT 3840

TACGCGCAGA AAAAAAGGAT CTCAAGAAGA TCCTTTGATC TTTTCTACGG GGTCTGACGC 3900

TCAGTGGAAC GAAAACTCAC GTTAAGGGAT TTTGGTCATG AGATTATCAA AAAGGATCTT 3960

CACCTAGATC CTTTTAAATT AAAAATGAAG TTTTAAATCA ATCTAAAGTA TATATGAGTA 4020

AACTTGGTCT GACAGTTACC AATGCTTAAT CAGTGAGGCA CCTATCTCAG CGATCTGTCT 4080

ATTTCGTTCA TCCATAGTTG CCTGACTCCC CGTCGTGTAG ATAACTACGA TACGGGAGGG 4140

CTTACCATCT GGCCCCAGTG CTGCAATGAT ACCGCGAGAC CCACGCTCAC CGGCTCCAGA 4200

TTTATCAGCA ATAAACCAGC CAGCCGGAAG GGCCGAGCGC AGAAGTGGTC CTGCAACTTT 4260

ATCCGCCTCC ATCCAGTCTA TTAATTGTTG CCGGGAAGCT AGAGTAAGTA GTTCGCCAGT 4320

TAATAGTTTG CGCAACGTTG TTGCCATTGC TACAGGCATC GTGGTGTCAC GCTCGTCGTT 4380

TGGTATGGCT TCATTCAGCT CCGGTTCCCA ACGATCAAGG CGAGTTACAT GATCCCCCAT 4440

GTTGTGCAAA AAAGCGGTTA GCTCCTTCGG TCCTCCGATC GTTGTCAGAA GTAAGTTGGC 4500

CGCAGTGTTA TCACTCATGG TTATGGCAGC ACTGCATAAT TCTCTTACTG TCATGCCATC 4560

CGTAAGATGC TTTTCTGTGA CTGGTGAGTA CTCAACCAAG TCATTCTGAG AATAGTGTAT 4620

GCGGCGACCG AGTTGCTCTT GCCCGGCGTC AATACGGGAT AATACCGCGC CACATAGCAG 4680

AACTTTAAAA GTGCTCATCA TTGGAAAACG TTCTTCGGGG CGAAAACTCT CAAGGATCTT 4740

ACCGCTGTTG AGATCCAGTT CGATGTAACC CACTCGTGCA CCCAACTGAT CTTCAGCATC 4800

TTTTACTTTC ACCAGCGTTT CTGGGTGAGC AAAAACAGGA AGGCAAAATG CCGCAAAAAA 4860

GGGAATAAGG GCGACACGGA AATGTTGAAT ACTCATACTC TTCCTTTTTC AATATTATTG 4920

AAGCATTTAT CAGGGTTATT GTCTCATGAG CGGATACATA TTTGAATGTA TTTAGAAAAA 4980

TAAACAAATA GGGGTTCCGC GCACATTTCC CCGAAAAGTG CCACCTGACG CGCCCTGTAG 5040

-continued

CGGCGCATTA AGCGCGGCGG GTGTGGTGGT TACGCGCAGC GTGACCGCTA CACTTGCCAG 5100

CGCCCTAGCG CCCGCTCCTT TCGCTTTCTT CCCTTCCTTT CTCGCCACGT TCGCCGGCTT 5160

TCCCCGTCAA GCTCTAAATC GGGGGCTCCC TTTAGGGTTC CGATTTAGTG CTTTACGGCA 5220

CCTCGACCCC AAAAAACTTG ATTAGGGTGA TGGTTCACGT AGTGGGCCAT CGCCCTGATA 5280

GACGGTTTTT CGCCCTTTGA CGTTGGAGTC CACGTTCTTT AATAGTGGAC TCTTGTTCCA 5340

AACTGGAACA ACACTCAACC CTATCTCGGT CTATTCTTTT GATTTATAAG GGATTTTGCC 5400

GATTTCGGCC TATTGGTTAA AAAATGAGCT GATTTAACAA AAATTTAACG CGAATTTTAA 5460

CAAAATATTA ACGTTTACAA TTTCCCATTC GCCATTCAGG CTGCGCAACT GTTGGGAAGG 5520

GCGATCGGTG CGGGCCTCTT CGCTATTACG CCAGCCCAAG CTACCATGAT AAGTAAGTAA 5580

TATTAAGGTA CGTGGAGGTT TTACTTGCTT TAAAAAACCT CCCACACCTC CCCCTGAACC 5640

TGAAACATAA AATGAATGCA ATTGTTGTTG TTAACTTGTT TATTGCAGCT TATAATGGTT 5700

ACAAATAAAG CAATAGCATC ACAAATTTCA CAAATAAAGC ATTTTTTTCA CTGCATTCTA 5760

GTTGTGGTTT GTCCAAACTC ATCAATGTAT CTTATGGTAC TGTAACTGAG CTAACATAA 5819

(2) INFORMATION FOR SEQ ID NO:28:

(i) SEQUENCE CHARACTERISTICS:
(A) LENGTH: 5819 base pairs
(B) TYPE: nucleic acid
(C) STRANDEDNESS: double
(D) TOPOLOGY: circular (xi) SEQUENCE DESCRIPTION: SEQ ID NO:28:

CCCGGGAGAC CTGCAAGCCT GCAGACACTC CCCTCCCGCC CCCACTGAAC CCTTGACCCC 60

TGCCCTGCAG CCCCCGCAGC TTGCTGTTTG CCCACTCTAT TTGCCCAGCC CCATTTGAGT 120

GTATGATCCT TGAACTCTTA AGTTCCACAT TGCCAGGACC AGTGAGCAGC AACAGGGCCG 180

GGGCTGGCTT ATCAGCCTCC CAGCCCAGAC CCTGGCTGCA GACATAAATA GGCCCTGCAA 240

GAGCTGGCTG CTTAGTCGAG ATCTAAGTAA GCTTGGCATT CCGGTACTGT TGGTAAAATG 300

GAAGACGCCA AAAACATAAA GAAAGGCCCG GCGCCATTCT ATCCTCTAGA GGATGGAACC 360

GCTGGAGAGC AACTGCATAA GGCTATGAAG AGATACGCCC TGGTTCCTGG AACAATTGCT 420

TTTACAGATG CACATATCGA GGTGAACATC ACGTACGCGG AATACTTCGA AATGTCCGTT 480

CGGTTGGCAG AAGCTATGAA ACGATATGGG CTGAATACAA ATCACAGAAT CGTCGTATGC 540

AGTGAAAACT CTCTTCAATT CTTTATGCCG GTGTTGGGCG CGTTATTTAT CGGAGTTGCA 600

GTTGCGCCCG CGAACGACAT TTATAATGAA CGTGAATTGC TCAACAGTAT GAACATTTCG 660

CAGCCTACCG TAGTGTTTGT TTCCAAAAAG GGGTTGCAAA AAATTTTGAA CGTGCAAAAA 720

AAATTACCAA TAATCCAGAA AATTATTATC ATGGATTCTA AAACGGATTA CCAGGGATTT 780

CAGTCGATGT ACACGTTCGT CACATCTCAT CTACCTCCCG GTTTTAATGA ATACGATTTT 840

GTACCAGAGT CCTTTGATCG TGACAAAACA ATTGCACTGA TAATGAATTC CTCTGGATCT 900

ACTGGGTTAC CTAAGGGTGT GGCCCTTCCG CATAGAACTG CCTGCGTCAG ATTCTCGCAT 960

GCCAGAGATC CTATTTTTGG CAATCAAATC ATTCCGGATA CTGCGATTTT AAGTGTTGTT 1020

CCATTCCATC ACGGTTTTGG AATGTTTACT ACACTCGGAT ATTTGATATG TGGATTTCGA 1080

GTCGTCTTAA TGTATAGATT TGAAGAAGAG CTGTTTTTAC GATCCCTTCA GGATTACAAA 1140

ATTCAAAGTG CGTTGCTAGT ACCAACCCTA TTTTCATTCT TCGCCAAAAG CACTCTGATT 1200

GACAAATACG ATTTATCTAA TTTACACGAA ATTGCTTCTG GGGGCGCACC TCTTTCGAAA 1260

-continued

GAAGTCGGGG AAGCGGTTGC AAAACGCTTC CATCTTCCAG GGATACGACA AGGATATGGG 1320

CTCACTGAGA CTACATCAGC TATTCTGATT ACACCCGAGG GGGATGATAA ACCGGGCGCG 1380

GTCGGTAAAG TTGTTCCATT TTTTGAAGCG AAGGTTGTGG ATCTGGATAC CGGGAAAACG 1440

CTGGGCGTTA ATCAGAGAGG CGAATTATGT GTCAGAGGAC CTATGATTAT GTCCGGTTAT 1500

GTAAACAATC CGGAAGCGAC CAACGCCTTG ATTGACAAGG ATGGATGGCT ACATTCTGGA 1560

GACATAGCTT ACTGGGACGA AGACGAACAC TTCTTCATAG TTGACCGCTT GAAGTCTTTA 1620

ATTAAATACA AAGGATATCA GGTGGCCCCC GCTGAATTGG AATCGATATT GTTACAACAC 1680

CCCAACATCT TCGACGCGGG CGTGGCAGGT CTTCCCGACG ATGACGCCGG TGAACTTCCC 1740

GCCGCCGTTG TTGTTTTGGA GCACGGAAAG ACGATGACGG AAAAAGAGAT CGTGGATTAC 1800

GTCGCCAGTC AAGTAACAAC CGCGAAAAAG TTGCGCGGAG GAGTTGTGTT TGTGGACGAA 1860

GTACCGAAAG GTCTTACCGG AAAACTCGAC GCAAGAAAAA TCAGAGAGAT CCTCATAAAG 1920

GCCAAGAAGG GCGGAAAGTC CAAATTGTAA AATGTAACTG TATTCAGCGA TGACGAAATT 1980

CTTAGCTATT GTAATACTGC GATGAGTGGC AGGGCGGGGC GTAATTTTTT TAAGGCAGTT 2040

ATTGGTGCCC TTAAACGCCT GGTGCTACGC CTGAATAAGT GATAATAAGC GGATGAATGG 2100

CAGAAATTCG CCGGATCTTT GTGAAGGAAC CTTACTTCTG TGGTGTGACA TAATTGGACA 2160

AACTACCTAC AGAGATTTAA AGCTCTAAGG TAAATATAAA ATTTTTAAGT GTATAATGTG 2220

TTAAACTACT GATTCTAATT GTTTGTGTAT TTTAGATTCC AACCTATGGA ACTGATGAAT 2280

GGGAGCAGTG GTGGAATGCC TTTAATGAGG AAAACCTGTT TTGCTCAGAA GAAATGCCAT 2340

CTAGTGATGA TGAGGCTACT GCTGACTCTC AACATTCTAC TCCTCCAAAA AAGAAGAGAA 2400

AGGTAGAAGA CCCCAAGGAC TTTCCTTCAG AATTGCTAAG TTTTTTGAGT CATGCTGTGT 2460

TTAGTAATAG AACTCTTGCT TGCTTTGCTA TTTACACCAC AAAGGAAAAA GCTGCACTGC 2520

TATACAAGAA AATTATGGAA AAATATTCTG TAACCTTTAT AAGTAGGCAT AACAGTTATA 2580

ATCATAACAT ACTGTTTTTT CTTACTCCAC ACAGGCATAG AGTGTCTGCT ATTAATAACT 2640

ATGCTCAAAA ATTGTGTACC TTTAGCTTTT TAATTTGTAA AGGGGTTAAT AAGGAATATT 2700

TGATGTATAG TGCCTTGACT AGAGATCATA ATCAGCCATA CCACATTTGT AGAGGTTTTA 2760

CTTGCTTTAA AAAACCTCCC ACACCTCCCC CTGAACCTGA AACATAAAAT GAATGCAATT 2820

GTTGTTGTTA ACTTGTTTAT TGCAGCTTAT AATGGTTACA AATAAAGCAA TAGCATCACA 2880

AATTTCACAA ATAAAGCATT TTTTTCACTG CATTCTAGTT GTGGTTTGTC CAAACTCATC 2940

AATGTATCTT ATCATGTCTG GATCCGTCGA CCGATGCCCT TGAGAGCCTT CAACCCAGTC 3000

AGCTCCTTCC GGTGGGCGCG GGGCATGACT ATCGTCGCCG CACTTATGAC TGTCTTCTTT 3060

ATCATGCAAC TCGTAGGACA GGTGCCGGCA GCGCTCTTCC GCTTCCTCGC TCACTGACTC 3120

GCTGCGCTCG GTCGTTCGGC TGCGGCGAGC GGTATCAGCT CACTCAAAGG CGGTAATACG 3180

GTTATCCACA GAATCAGGGG ATAACGCAGG AAAGAACATG TGAGCAAAAG GCCAGCAAAA 3240

GGCCAGGAAC CGTAAAAAGG CCGCGTTGCT GGCGTTTTTC CATAGGCTCC GCCCCCCTGA 3300

CGAGCATCAC AAAAATCGAC GCTCAAGTCA GAGGTGGCGA AACCCGACAG GACTATAAAG 3360

ATACCAGGCG TTTCCCCCTG GAAGCTCCCT CGTGCGCTCT CCTGTTCCGA CCCTGCCGCT 3420

TACCGGATAC CTGTCCGCCT TTCTCCCTTC GGGAAGCGTG GCGCTTTCTC AATGCTCACG 3480

CTGTAGGTAT CTCAGTTCGG TGTAGGTCGT TCGCTCCAAG CTGGGCTGTG TGCACGAACC 3540

CCCCGTTCAG CCCGACCGCT GCGCCTTATC CGGTAACTAT CGTCTTGAGT CCAACCCGGT 3600

AAGACACGAC TTATCGCCAC TGGCAGCAGC CACTGGTAAC AGGATTAGCA GAGCGAGGTA 3660

-continued

```
TGTAGGCGGT GCTACAGAGT TCTTGAAGTG GTGGCCTAAC TACGGCTACA CTAGAAGGAC   3720

AGTATTTGGT ATCTGCGCTC TGCTGAAGCC AGTTACCTTC GGAAAAAGAG TTGGTAGCTC   3780

TTGATCCGGC AAACAAACCA CCGCTGGTAG CGGTGGTTTT TTTGTTTGCA AGCAGCAGAT   3840

TACGCGCAGA AAAAAAGGAT CTCAAGAAGA TCCTTTGATC TTTTCTACGG GGTCTGACGC   3900

TCAGTGGAAC GAAAACTCAC GTTAAGGGAT TTTGGTCATG AGATTATCAA AAAGGATCTT   3960

CACCTAGATC CTTTTAAATT AAAAATGAAG TTTTAAATCA ATCTAAAGTA TATATGAGTA   4020

AACTTGGTCT GACAGTTACC AATGCTTAAT CAGTGAGGCA CCTATCTCAG CGATCTGTCT   4080

ATTTCGTTCA TCCATAGTTG CCTGACTCCC CGTCGTGTAG ATAACTACGA TACGGGAGGG   4140

CTTACCATCT GGCCCCAGTG CTGCAATGAT ACCGCGAGAC CCACGCTCAC CGGCTCCAGA   4200

TTTATCAGCA ATAAACCAGC CAGCCGGAAG GGCCGAGCGC AGAAGTGGTC CTGCAACTTT   4260

ATCCGCCTCC ATCCAGTCTA TTAATTGTTG CCGGGAAGCT AGAGTAAGTA GTTCGCCAGT   4320

TAATAGTTTG CGCAACGTTG TTGCCATTGC TACAGGCATC GTGGTGTCAC GCTCGTCGTT   4380

TGGTATGGCT TCATTCAGCT CCGGTTCCCA ACGATCAAGG CGAGTTACAT GATCCCCCAT   4440

GTTGTGCAAA AAAGCGGTTA GCTCCTTCGG TCCTCCGATC GTTGTCAGAA GTAAGTTGGC   4500

CGCAGTGTTA TCACTCATGG TTATGGCAGC ACTGCATAAT TCTCTTACTG TCATGCCATC   4560

CGTAAGATGC TTTTCTGTGA CTGGTGAGTA CTCAACCAAG TCATTCTGAG AATAGTGTAT   4620

GCGGCGACCG AGTTGCTCTT GCCCGGCGTC AATACGGGAT AATACCGCGC CACATAGCAG   4680

AACTTTAAAA GTGCTCATCA TTGGAAAACG TTCTTCGGGG CGAAAACTCT CAAGGATCTT   4740

ACCGCTGTTG AGATCCAGTT CGATGTAACC CACTCGTGCA CCCAACTGAT CTTCAGCATC   4800

TTTTACTTTC ACCAGCGTTT CTGGGTGAGC AAAAACAGGA AGGCAAAATG CCGCAAAAAA   4860

GGGAATAAGG GCGACACGGA AATGTTGAAT ACTCATACTC TTCCTTTTTC AATATTATTG   4920

AAGCATTTAT CAGGGTTATT GTCTCATGAG CGGATACATA TTTGAATGTA TTTAGAAAAA   4980

TAAACAAATA GGGGTTCCGC GCACATTTCC CCGAAAAGTG CCACCTGACG CGCCCTGTAG   5040

CGGCGCATTA AGCGCGGCGG GTGTGGTGGT TACGCGCAGC GTGACCGCTA CACTTGCCAG   5100

CGCCCTAGCG CCCGCTCCTT TCGCTTTCTT CCCTTCCTTT CTCGCCACGT TCGCCGGCTT   5160

TCCCCGTCAA GCTCTAAATC GGGGGCTCCC TTTAGGGTTC CGATTTAGTG CTTTACGGCA   5220

CCTCGACCCC AAAAAACTTG ATTAGGGTGA TGGTTCACGT AGTGGGCCAT CGCCCTGATA   5280

GACGGTTTTT CGCCCTTTGA CGTTGGAGTC CACGTTCTTT AATAGTGGAC TCTTGTTCCA   5340

AACTGGAACA ACACTCAACC CTATCTCGGT CTATTCTTTT GATTTATAAG GGATTTTGCC   5400

GATTTCGGCC TATTGGTTAA AAAATGAGCT GATTTAACAA AAATTTAACG CGAATTTTAA   5460

CAAAATATTA ACGTTTACAA TTTCCCATTC GCCATTCAGG CTGCGCAACT GTTGGGAAGG   5520

GCGATCGGTG CGGGCCTCTT CGCTATTACG CCAGCCCAAG CTACCATGAT AAGTAAGTAA   5580

TATTAAGGTA CGTGGAGGTT TTACTTGCTT TAAAAAACCT CCCACACCTC CCCCTGAACC   5640

TGAAACATAA AATGAATGCA ATTGTTGTTG TTAACTTGTT TATTGCAGCT TATAATGGTT   5700

ACAAATAAAG CAATAGCATC ACAAATTTCA CAAATAAAGC ATTTTTTTCA CTGCATTCTA   5760

GTTGTGGTTT GTCCAAACTC ATCAATGTAT CTTATGGTAC TGTAACTGAG CTAACATAA    5819
```

(2) INFORMATION FOR SEQ ID NO:29:

(i) SEQUENCE CHARACTERISTICS:
(A) LENGTH: 5793 base pairs
(B) TYPE: nucleic acid -continued (C) STRANDEDNESS: double
(D) TOPOLOGY: circular (xi) SEQUENCE DESCRIPTION: SEQ ID NO:29:

CCCGGGAGGT ACCAGCCCCA GGGACAGAGC TGCTAGCTCG AGATCTGCAT CTCAATTAGT 60

CAGCAACCAT AGTCCCGCCC CTAACTCCGC CCATCCCGCC CCTAACTCCG CCCAGTTCCG 120

CCCATTCTCC GCCCCATGGC TGACTAATTT TTTTTATTTA TGCAGAGGCC GAGGCCGCCT 180

CGGCCTCTGA GCTATTCCAG AAGTAGTGAG GAGGCTTTTT TGGAGGCCTA GGCTTTTGCA 240

AAAAGCTTGG CATTCCGGTA CTGTTGGTAA AATGGAAGAC GCCAAAAACA TAAAGAAAGG 300

CCCGGCGCCA TTCTATCCTC TAGAGGATGG AACCGCTGGA GAGCAACTGC ATAAGGCTAT 360

GAAGAGATAC GCCCTGGTTC CTGGAACAAT TGCTTTTACA GATGCACATA TCGAGGTGAA 420

CATCACGTAC GCGGAATACT TCGAAATGTC CGTTCGGTTG GCAGAAGCTA TGAAACGATA 480

TGGGCTGAAT ACAAATCACA GAATCGTCGT ATGCAGTGAA AACTCTCTTC AATTCTTTAT 540

GCCGGTGTTG GGCGCGTTAT TTATCGGAGT TGCAGTTGCG CCCGCGAACG ACATTTATAA 600

TGAACGTGAA TTGCTCAACA GTATGAACAT TTCGCAGCCT ACCGTAGTGT TTGTTTCCAA 660

AAAGGGGTTG CAAAAAATTT TGAACGTGCA AAAAAAATTA CCAATAATCC AGAAAATTAT 720

TATCATGGAT TCTAAAACGG ATTACCAGGG ATTTCAGTCG ATGTACACGT TCGTCACATC 780

TCATCTACCT CCCGGTTTTA ATGAATACGA TTTTGTACCA GAGTCCTTTG ATCGTGACAA 840

AACAATTGCA CTGATAATGA ATTCCTCTGG ATCTACTGGG TTACCTAAGG GTGTGGCCCT 900

TCCGCATAGA ACTGCCTGCG TCAGATTCTC GCATGCCAGA GATCCTATTT TTGGCAATCA 960

AATCATTCCG GATACTGCGA TTTTAAGTGT TGTTCCATTC CATCACGGTT TTGGAATGTT 1020

TACTACACTC GGATATTTGA TATGTGGATT TCGAGTCGTC TTAATGTATA GATTTGAAGA 1080

AGAGCTGTTT TTACGATCCC TTCAGGATTA CAAAATTCAA AGTGCGTTGC TAGTACCAAC 1140

CCTATTTTCA TTCTTCGCCA AAAGCACTCT GATTGACAAA TACGATTTAT CTAATTTACA 1200

CGAAATTGCT TCTGGGGGCG CACCTCTTTC GAAAGAAGTC GGGGAAGCGG TTGCAAAACG 1260

CTTCCATCTT CCAGGGATAC GACAAGGATA TGGGCTCACT GAGACTACAT CAGCTATTCT 1320

GATTACACCC GAGGGGGATG ATAAACCGGG CGCGGTCGGT AAAGTTGTTC CATTTTTTGA 1380

AGCGAAGGTT GTGGATCTGG ATACCGGGAA AACGCTGGGC GTTAATCAGA GAGGCGAATT 1440

ATGTGTCAGA GGACCTATGA TTATGTCCGG TTATGTAAAC AATCCGGAAG CGACCAACGC 1500

CTTGATTGAC AAGGATGGAT GGCTACATTC TGGAGACATA GCTTACTGGG ACGAAGACGA 1560

ACACTTCTTC ATAGTTGACC GCTTGAAGTC TTTAATTAAA TACAAAGGAT ATCAGGTGGC 1620

CCCCGCTGAA TTGGAATCGA TATTGTTACA ACACCCCAAC ATCTTCGACG CGGGCGTGGC 1680

AGGTCTTCCC GACGATGACG CCGGTGAACT TCCCGCCGCC GTTGTTGTTT TGGAGCACGG 1740

AAAGACGATG ACGGAAAAAG AGATCGTGGA TTACGTCGCC AGTCAAGTAA CAACCGCGAA 1800

AAAGTTGCGC GGAGGAGTTG TGTTTGTGGA CGAAGTACCG AAAGGTCTTA CCGGAAAACT 1860

CGACGCAAGA AAAATCAGAG AGATCCTCAT AAAGGCCAAG AAGGGCGGAA AGTCCAAATT 1920

GTAAAATGTA ACTGTATTCA GCGATGACGA AATTCTTAGC TATTGTAATA CTGCGATGAG 1980

TGGCAGGGCG GGGCGTAATT TTTTTAAGGC AGTTATTGGT GCCCTTAAAC GCCTGGTGCT 2040

ACGCCTGAAT AAGTGATAAT AAGCGGATGA ATGGCAGAAA TTCGCCGGAT CTTTGTGAAG 2100

GAACCTTACT TCTGTGGTGT GACATAATTG GACAAACTAC CTACAGAGAT TTAAAGCTCT 2160

AAGGTAAATA TAAAATTTTT AAGTGTATAA TGTGTTAAAC TACTGATTCT AATTGTTTGT 2220

-continued

```
GTATTTTAGA TTCCAACCTA TGGAACTGAT GAATGGGAGC AGTGGTGGAA TGCCTTTAAT   2280
GAGGAAAACC TGTTTTGCTC AGAAGAAATG CCATCTAGTG ATGATGAGGC TACTGCTGAC   2340
TCTCAACATT CTACTCCTCC AAAAAAGAAG AGAAAGGTAG AAGACCCCAA GGACTTTCCT   2400
TCAGAATTGC TAAGTTTTTT GAGTCATGCT GTGTTTAGTA ATAGAACTCT TGCTTGCTTT   2460
GCTATTTACA CCACAAAGGA AAAAGCTGCA CTGCTATACA AGAAAATTAT GGAAAAATAT   2520
TCTGTAACCT TTATAAGTAG GCATAACAGT TATAATCATA ACATACTGTT TTTTCTTACT   2580
CCACACAGGC ATAGAGTGTC TGCTATTAAT AACTATGCTC AAAAATTGTG TACCTTTAGC   2640
TTTTTAATTT GTAAAGGGGT TAATAAGGAA TATTTGATGT ATAGTGCCTT GACTAGAGAT   2700
CATAATCAGC CATACCACAT TTGTAGAGGT TTTACTTGCT TTAAAAAACC TCCCACACCT   2760
CCCCCTGAAC CTGAAACATA AAATGAATGC AATTGTTGTT GTTAACTTGT TTATTGCAGC   2820
TTATAATGGT TACAAATAAA GCAATAGCAT CACAAATTTC ACAAATAAAG CATTTTTTTC   2880
ACTGCATTCT AGTTGTGGTT TGTCCAAACT CATCAATGTA TCTTATCATG TCTGGATCCG   2940
TCGACCGATG CCCTTGAGAG CCTTCAACCC AGTCAGCTCC TTCCGGTGGG CGCGGGGCAT   3000
GACTATCGTC GCCGCACTTA TGACTGTCTT CTTTATCATG CAACTCGTAG GACAGGTGCC   3060
GGCAGCGCTC TTCCGCTTCC TCGCTCACTG ACTCGCTGCG CTCGGTCGTT CGGCTGCGGC   3120
GAGCGGTATC AGCTCACTCA AAGGCGGTAA TACGGTTATC CACAGAATCA GGGGATAACG   3180
CAGGAAAGAA CATGTGAGCA AAAGGCCAGC AAAAGGCCAG GAACCGTAAA AAGGCCGCGT   3240
TGCTGGCGTT TTTCCATAGG CTCCGCCCCC CTGACGAGCA TCACAAAAAT CGACGCTCAA   3300
GTCAGAGGTG GCGAAACCCG ACAGGACTAT AAAGATACCA GGCGTTTCCC CCTGGAAGCT   3360
CCCTCGTGCG CTCTCCTGTT CCGACCCTGC CGCTTACCGG ATACCTGTCC GCCTTTCTCC   3420
CTTCGGGAAG CGTGGCGCTT TCTCAATGCT CACGCTGTAG GTATCTCAGT TCGGTGTAGG   3480
TCGTTCGCTC CAAGCTGGGC TGTGTGCACG AACCCCCCGT TCAGCCCGAC CGCTGCGCCT   3540
TATCCGGTAA CTATCGTCTT GAGTCCAACC CGGTAAGACA CGACTTATCG CCACTGGCAG   3600
CAGCCACTGG TAACAGGATT AGCAGAGCGA GGTATGTAGG CGGTGCTACA GAGTTCTTGA   3660
AGTGGTGGCC TAACTACGGC TACACTAGAA GGACAGTATT TGGTATCTGC GCTCTGCTGA   3720
AGCCAGTTAC CTTCGGAAAA AGAGTTGGTA GCTCTTGATC CGGCAAACAA ACCACCGCTG   3780
GTAGCGGTGG TTTTTTTGTT TGCAAGCAGC AGATTACGCG CAGAAAAAAA GGATCTCAAG   3840
AAGATCCTTT GATCTTTTCT ACGGGGTCTG ACGCTCAGTG GAACGAAAAC TCACGTTAAG   3900
GGATTTTGGT CATGAGATTA TCAAAAAGGA TCTTCACCTA GATCCTTTTA AATTAAAAAT   3960
GAAGTTTTAA ATCAATCTAA AGTATATATG AGTAAACTTG GTCTGACAGT TACCAATGCT   4020
TAATCAGTGA GGCACCTATC TCAGCGATCT GTCTATTTCG TTCATCCATA GTTGCCTGAC   4080
TCCCCGTCGT GTAGATAACT ACGATACGGG AGGGCTTACC ATCTGGCCCC AGTGCTGCAA   4140
TGATACCGCG AGACCCACGC TCACCGGCTC CAGATTTATC AGCAATAAAC CAGCCAGCCG   4200
GAAGGGCCGA GCGCAGAAGT GGTCCTGCAA CTTTATCCGC CTCCATCCAG TCTATTAATT   4260
GTTGCCGGGA AGCTAGAGTA AGTAGTTCGC CAGTTAATAG TTTGCGCAAC GTTGTTGCCA   4320
TTGCTACAGG CATCGTGGTG TCACGCTCGT CGTTTGGTAT GGCTTCATTC AGCTCCGGTT   4380
CCCAACGATC AAGGCGAGTT ACATGATCCC CCATGTTGTG CAAAAAAGCG GTTAGCTCCT   4440
TCGGTCCTCC GATCGTTGTC AGAAGTAAGT TGGCCGCAGT GTTATCACTC ATGGTTATGG   4500
CAGCACTGCA TAATTCTCTT ACTGTCATGC CATCCGTAAG ATGCTTTTCT GTGACTGGTG   4560
AGTACTCAAC CAAGTCATTC TGAGAATAGT GTATGCGGCG ACCGAGTTGC TCTTGCCCGG   4620
```

-continued

CGTCAATACG GGATAATACC GCGCCACATA GCAGAACTTT AAAAGTGCTC ATCATTGGAA 4680

AACGTTCTTC GGGGCGAAAA CTCTCAAGGA TCTTACCGCT GTTGAGATCC AGTTCGATGT 4740

AACCCACTCG TGCACCCAAC TGATCTTCAG CATCTTTTAC TTTCACCAGC GTTTCTGGGT 4800

GAGCAAAAAC AGGAAGGCAA AATGCCGCAA AAAAGGGAAT AAGGGCGACA CGGAAATGTT 4860

GAATACTCAT ACTCTTCCTT TTTCAATATT ATTGAAGCAT TTATCAGGGT TATTGTCTCA 4920

TGAGCGGATA CATATTTGAA TGTATTTAGA AAAATAAACA AATAGGGGTT CCGCGCACAT 4980

TTCCCCGAAA AGTGCCACCT GACGCGCCCT GTAGCGGCGC ATTAAGCGCG GCGGGTGTGG 5040

TGGTTACGCG CAGCGTGACC GCTACACTTG CCAGCGCCCT AGCGCCCGCT CCTTTCGCTT 5100

TCTTCCCTTC CTTTCTCGCC ACGTTCGCCG GCTTTCCCCG TCAAGCTCTA AATCGGGGGC 5160

TCCCTTTAGG GTTCCGATTT AGTGCTTTAC GGCACCTCGA CCCCAAAAAA CTTGATTAGG 5220

GTGATGGTTC ACGTAGTGGG CCATCGCCCT GATAGACGGT TTTTCGCCCT TTGACGTTGG 5280

AGTCCACGTT CTTTAATAGT GGACTCTTGT TCCAAACTGG AACAACACTC AACCCTATCT 5340

CGGTCTATTC TTTTGATTTA TAAGGGATTT TGCCGATTTC GGCCTATTGG TTAAAAAATG 5400

AGCTGATTTA ACAAAAATTT AACGCGAATT TTAACAAAAT ATTAACGTTT ACAATTTCCC 5460

ATTCGCCATT CAGGCTGCGC AACTGTTGGG AAGGGCGATC GGTGCGGGCC TCTTCGCTAT 5520

TACGCCAGCC CAAGCTACCA TGATAAGTAA GTAATATTAA GGTACGTGGA GGTTTTACTT 5580

GCTTTAAAAA ACCTCCCACA CCTCCCCCTG AACCTGAAAC ATAAAATGAA TGCAATTGTT 5640

GTTGTTAACT TGTTTATTGC AGCTTATAAT GGTTACAAAT AAAGCAATAG CATCACAAAT 5700

TTCACAAATA AAGCATTTTT TTCACTGCAT TCTAGTTGTG GTTTGTCCAA ACTCATCAAT 5760

GTATCTTATG GTACTGTAAC TGAGCTAACA TAA 5793

(2) INFORMATION FOR SEQ ID NO:30:

(i) SEQUENCE CHARACTERISTICS:
(A) LENGTH: 5793 base pairs
(B) TYPE: nucleic acid
(C) STRANDEDNESS: double
(D) TOPOLOGY: circular (xi) SEQUENCE DESCRIPTION: SEQ ID NO:30:

CCCGGGAGGT ACCAGCCCCA TTTGAGTGTA TGCTAGCTCG AGATCTGCAT CTCAATTAGT 60

CAGCAACCAT AGTCCCGCCC CTAACTCCGC CCATCCCGCC CCTAACTCCG CCCAGTTCCG 120

CCCATTCTCC GCCCCATGGC TGACTAATTT TTTTTATTTA TGCAGAGGCC GAGGCCGCCT 180

CGGCCTCTGA GCTATTCCAG AAGTAGTGAG GAGGCTTTTT TGGAGGCCTA GGCTTTTGCA 240

AAAAGCTTGG CATTCCGGTA CTGTTGGTAA AATGGAAGAC GCCAAAAACA TAAAGAAAGG 300

CCCGGCGCCA TTCTATCCTC TAGAGGATGG AACCGCTGGA GAGCAACTGC ATAAGGCTAT 360

GAAGAGATAC GCCCTGGTTC CTGGAACAAT TGCTTTTACA GATGCACATA TCGAGGTGAA 420

CATCACGTAC GCGGAATACT TCGAAATGTC CGTTCGGTTG GCAGAAGCTA TGAAACGATA 480

TGGGCTGAAT ACAAATCACA GAATCGTCGT ATGCAGTGAA AACTCTCTTC AATTCTTTAT 540

GCCGGTGTTG GGCGCGTTAT TTATCGGAGT TGCAGTTGCG CCCGCGAACG ACATTTATAA 600

TGAACGTGAA TTGCTCAACA GTATGAACAT TTCGCAGCCT ACCGTAGTGT TTGTTTCCAA 660

AAAGGGGTTG CAAAAAATTT TGAACGTGCA AAAAAAATTA CCAATAATCC AGAAAATTAT 720

TATCATGGAT TCTAAAACGG ATTACCAGGG ATTTCAGTCG ATGTACACGT TCGTCACATC 780

TCATCTACCT CCCGGTTTTA ATGAATACGA TTTTGTACCA GAGTCCTTTG ATCGTGACAA 840

-continued

```
AACAATTGCA CTGATAATGA ATTCCTCTGG ATCTACTGGG TTACCTAAGG GTGTGGCCCT    900
TCCGCATAGA ACTGCCTGCG TCAGATTCTC GCATGCCAGA GATCCTATTT TTGGCAATCA    960
AATCATTCCG GATACTGCGA TTTTAAGTGT TGTTCCATTC CATCACGGTT TTGGAATGTT   1020
TACTACACTC GGATATTTGA TATGTGGATT TCGAGTCGTC TTAATGTATA GATTTGAAGA   1080
AGAGCTGTTT TTACGATCCC TTCAGGATTA CAAAATTCAA AGTGCGTTGC TAGTACCAAC   1140
CCTATTTTCA TTCTTCGCCA AAAGCACTCT GATTGACAAA TACGATTTAT CTAATTTACA   1200
CGAAATTGCT TCTGGGGGCG CACCTCTTTC GAAAGAAGTC GGGGAAGCGG TTGCAAAACG   1260
CTTCCATCTT CCAGGGATAC GACAAGGATA TGGGCTCACT GAGACTACAT CAGCTATTCT   1320
GATTACACCC GAGGGGGATG ATAAACCGGG CGCGGTCGGT AAAGTTGTTC CATTTTTTGA   1380
AGCGAAGGTT GTGGATCTGG ATACCGGGAA AACGCTGGGC GTTAATCAGA GAGGCGAATT   1440
ATGTGTCAGA GGACCTATGA TTATGTCCGG TTATGTAAAC AATCCGGAAG CGACCAACGC   1500
CTTGATTGAC AAGGATGGAT GGCTACATTC TGGAGACATA GCTTACTGGG ACGAAGACGA   1560
ACACTTCTTC ATAGTTGACC GCTTGAAGTC TTTAATTAAA TACAAAGGAT ATCAGGTGGC   1620
CCCCGCTGAA TTGGAATCGA TATTGTTACA ACACCCCAAC ATCTTCGACG CGGGCGTGGC   1680
AGGTCTTCCC GACGATGACG CCGGTGAACT TCCCGCCGCC GTTGTTGTTT TGGAGCACGG   1740
AAAGACGATG ACGGAAAAAG AGATCGTGGA TTACGTCGCC AGTCAAGTAA CAACCGCGAA   1800
AAAGTTGCGC GGAGGAGTTG TGTTTGTGGA CGAAGTACCG AAAGGTCTTA CCGGAAAACT   1860
CGACGCAAGA AAAATCAGAG AGATCCTCAT AAAGGCCAAG AAGGGCGGAA AGTCCAAATT   1920
GTAAAATGTA ACTGTATTCA GCGATGACGA AATTCTTAGC TATTGTAATA CTGCGATGAG   1980
TGGCAGGGCG GGGCGTAATT TTTTTAAGGC AGTTATTGGT GCCCTTAAAC GCCTGGTGCT   2040
ACGCCTGAAT AAGTGATAAT AAGCGGATGA ATGGCAGAAA TTCGCCGGAT CTTTGTGAAG   2100
GAACCTTACT TCTGTGGTGT GACATAATTG GACAAACTAC CTACAGAGAT TTAAAGCTCT   2160
AAGGTAAATA TAAAATTTTT AAGTGTATAA TGTGTTAAAC TACTGATTCT AATTGTTTGT   2220
GTATTTTAGA TTCCAACCTA TGGAACTGAT GAATGGGAGC AGTGGTGGAA TGCCTTTAAT   2280
GAGGAAAACC TGTTTTGCTC AGAAGAAATG CCATCTAGTG ATGATGAGGC TACTGCTGAC   2340
TCTCAACATT CTACTCCTCC AAAAAAGAAG AGAAAGGTAG AAGACCCCAA GGACTTTCCT   2400
TCAGAATTGC TAAGTTTTTT GAGTCATGCT GTGTTTAGTA ATAGAACTCT TGCTTGCTTT   2460
GCTATTTACA CCACAAAGGA AAAAGCTGCA CTGCTATACA AGAAAATTAT GGAAAAATAT   2520
TCTGTAACCT TTATAAGTAG GCATAACAGT TATAATCATA ACATACTGTT TTTTCTTACT   2580
CCACACAGGC ATAGAGTGTC TGCTATTAAT AACTATGCTC AAAAATTGTG TACCTTTAGC   2640
TTTTTAATTT GTAAAGGGGT TAATAAGGAA TATTTGATGT ATAGTGCCTT GACTAGAGAT   2700
CATAATCAGC CATACCACAT TTGTAGAGGT TTTACTTGCT TTAAAAAACC TCCCACACCT   2760
CCCCCTGAAC CTGAAACATA AAATGAATGC AATTGTTGTT GTTAACTTGT TTATTGCAGC   2820
TTATAATGGT TACAAATAAA GCAATAGCAT CACAAATTTC ACAAATAAAG CATTTTTTTC   2880
ACTGCATTCT AGTTGTGGTT TGTCCAAACT CATCAATGTA TCTTATCATG TCTGGATCCG   2940
TCGACCGATG CCCTTGAGAG CCTTCAACCC AGTCAGCTCC TTCCGGTGGG CGCGGGGCAT   3000
GACTATCGTC GCCGCACTTA TGACTGTCTT CTTTATCATG CAACTCGTAG GACAGGTGCC   3060
GGCAGCGCTC TTCCGCTTCC TCGCTCACTG ACTCGCTGCG CTCGGTCGTT CGGCTGCGGC   3120
GAGCGGTATC AGCTCACTCA AAGGCGGTAA TACGGTTATC CACAGAATCA GGGGATAACG   3180
```

-continued

```
CAGGAAAGAA CATGTGAGCA AAAGGCCAGC AAAAGGCCAG GAACCGTAAA AAGGCCGCGT   3240
TGCTGGCGTT TTTCCATAGG CTCCGCCCCC CTGACGAGCA TCACAAAAAT CGACGCTCAA   3300
GTCAGAGGTG GCGAAACCCG ACAGGACTAT AAAGATACCA GGCGTTTCCC CCTGGAAGCT   3360
CCCTCGTGCG CTCTCCTGTT CCGACCCTGC CGCTTACCGG ATACCTGTCC GCCTTTCTCC   3420
CTTCGGGAAG CGTGGCGCTT TCTCAATGCT CACGCTGTAG GTATCTCAGT TCGGTGTAGG   3480
TCGTTCGCTC CAAGCTGGGC TGTGTGCACG AACCCCCCGT TCAGCCCGAC CGCTGCGCCT   3540
TATCCGGTAA CTATCGTCTT GAGTCCAACC CGGTAAGACA CGACTTATCG CCACTGGCAG   3600
CAGCCACTGG TAACAGGATT AGCAGAGCGA GGTATGTAGG CGGTGCTACA GAGTTCTTGA   3660
AGTGGTGGCC TAACTACGGC TACACTAGAA GGACAGTATT TGGTATCTGC GCTCTGCTGA   3720
AGCCAGTTAC CTTCGGAAAA AGAGTTGGTA GCTCTTGATC CGGCAAACAA ACCACCGCTG   3780
GTAGCGGTGG TTTTTTTGTT TGCAAGCAGC AGATTACGCG CAGAAAAAAA GGATCTCAAG   3840
AAGATCCTTT GATCTTTTCT ACGGGGTCTG ACGCTCAGTG GAACGAAAAC TCACGTTAAG   3900
GGATTTTGGT CATGAGATTA TCAAAAAGGA TCTTCACCTA GATCCTTTTA AATTAAAAAT   3960
GAAGTTTTAA ATCAATCTAA AGTATATATG AGTAAACTTG GTCTGACAGT TACCAATGCT   4020
TAATCAGTGA GGCACCTATC TCAGCGATCT GTCTATTTCG TTCATCCATA GTTGCCTGAC   4080
TCCCCGTCGT GTAGATAACT ACGATACGGG AGGGCTTACC ATCTGGCCCC AGTGCTGCAA   4140
TGATACCGCG AGACCCACGC TCACCGGCTC CAGATTTATC AGCAATAAAC CAGCCAGCCG   4200
GAAGGGCCGA GCGCAGAAGT GGTCCTGCAA CTTTATCCGC CTCCATCCAG TCTATTAATT   4260
GTTGCCGGGA AGCTAGAGTA AGTAGTTCGC CAGTTAATAG TTTGCGCAAC GTTGTTGCCA   4320
TTGCTACAGG CATCGTGGTG TCACGCTCGT CGTTTGGTAT GGCTTCATTC AGCTCCGGTT   4380
CCCAACGATC AAGGCGAGTT ACATGATCCC CCATGTTGTG CAAAAAAGCG GTTAGCTCCT   4440
TCGGTCCTCC GATCGTTGTC AGAAGTAAGT TGGCCGCAGT GTTATCACTC ATGGTTATGG   4500
CAGCACTGCA TAATTCTCTT ACTGTCATGC CATCCGTAAG ATGCTTTTCT GTGACTGGTG   4560
AGTACTCAAC CAAGTCATTC TGAGAATAGT GTATGCGGCG ACCGAGTTGC TCTTGCCCGG   4620
CGTCAATACG GGATAATACC GCGCCACATA GCAGAACTTT AAAAGTGCTC ATCATTGGAA   4680
AACGTTCTTC GGGGCGAAAA CTCTCAAGGA TCTTACCGCT GTTGAGATCC AGTTCGATGT   4740
AACCCACTCG TGCACCCAAC TGATCTTCAG CATCTTTTAC TTTCACCAGC GTTTCTGGGT   4800
GAGCAAAAAC AGGAAGGCAA AATGCCGCAA AAAAGGGAAT AAGGGCGACA CGGAAATGTT   4860
GAATACTCAT ACTCTTCCTT TTTCAATATT ATTGAAGCAT TTATCAGGGT TATTGTCTCA   4920
TGAGCGGATA CATATTTGAA TGTATTTAGA AAAATAAACA AATAGGGGTT CCGCGCACAT   4980
TTCCCCGAAA AGTGCCACCT GACGCGCCCT GTAGCGGCGC ATTAAGCGCG GCGGGTGTGG   5040
TGGTTACGCG CAGCGTGACC GCTACACTTG CCAGCGCCCT AGCGCCCGCT CCTTTCGCTT   5100
TCTTCCCTTC CTTTCTCGCC ACGTTCGCCG GCTTTCCCCG TCAAGCTCTA AATCGGGGGC   5160
TCCCTTTAGG GTTCCGATTT AGTGCTTTAC GGCACCTCGA CCCCAAAAAA CTTGATTAGG   5220
GTGATGGTTC ACGTAGTGGG CCATCGCCCT GATAGACGGT TTTTCGCCCT TTGACGTTGG   5280
AGTCCACGTT CTTTAATAGT GGACTCTTGT TCCAAACTGG AACAACACTC AACCCTATCT   5340
CGGTCTATTC TTTTGATTTA TAAGGGATTT TGCCGATTTC GGCCTATTGG TTAAAAAATG   5400
AGCTGATTTA ACAAAAATTT AACGCGAATT TTAACAAAAT ATTAACGTTT ACAATTTCCC   5460
ATTCGCCATT CAGGCTGCGC AACTGTTGGG AAGGGCGATC GGTGCGGGCC TCTTCGCTAT   5520
TACGCCAGCC CAAGCTACCA TGATAAGTAA GTAATATTAA GGTACGTGGA GGTTTTACTT   5580
```

-continued

```
GCTTTAAAAA ACCTCCCACA CCTCCCCCTG AACCTGAAAC ATAAAATGAA TGCAATTGTT   5640
GTTGTTAACT TGTTTATTGC AGCTTATAAT GGTTACAAAT AAAGCAATAG CATCACAAAT   5700
TTCACAAATA AAGCATTTTT TTCACTGCAT TCTAGTTGTG GTTTGTCCAA ACTCATCAAT   5760
GTATCTTATG GTACTGTAAC TGAGCTAACA TAA                                5793
```

(2) INFORMATION FOR SEQ ID NO:31:

(i) SEQUENCE CHARACTERISTICS:
(A) LENGTH: 5791 base pairs
(B) TYPE: nucleic acid
(C) STRANDEDNESS: double
(D) TOPOLOGY: circular (xi) SEQUENCE DESCRIPTION: SEQ ID NO:31:

```
CCCGGGAGGT ACCTAATGGT GACAAAGCAG CTAGCTCGAG ATCTGCATCT CAATTAGTCA     60
GCAACCATAG TCCCGCCCCT AACTCCGCCC ATCCCGCCCC TAACTCCGCC CAGTTCCGCC    120
CATTCTCCGC CCCATGGCTG ACTAATTTTT TTTATTTATG CAGAGGCCGA GGCCGCCTCG    180
GCCTCTGAGC TATTCCAGAA GTAGTGAGGA GGCTTTTTTG GAGGCCTAGG CTTTTGCAAA    240
AAGCTTGGCA TTCCGGTACT GTTGGTAAAA TGGAAGACGC CAAAAACATA AAGAAAGGCC    300
CGGCGCCATT CTATCCTCTA GAGGATGGAA CCGCTGGAGA GCAACTGCAT AAGGCTATGA    360
AGAGATACGC CCTGGTTCCT GGAACAATTG CTTTTACAGA TGCACATATC GAGGTGAACA    420
TCACGTACGC GGAATACTTC GAAATGTCCG TTCGGTTGGC AGAAGCTATG AAACGATATG    480
GGCTGAATAC AAATCACAGA ATCGTCGTAT GCAGTGAAAA CTCTCTTCAA TTCTTTATGC    540
CGGTGTTGGG CGCGTTATTT ATCGGAGTTG CAGTTGCGCC CGCGAACGAC ATTTATAATG    600
AACGTGAATT GCTCAACAGT ATGAACATTT CGCAGCCTAC CGTAGTGTTT GTTTCCAAAA    660
AGGGGTTGCA AAAAATTTTG AACGTGCAAA AAAAATTACC AATAATCCAG AAAATTATTA    720
TCATGGATTC TAAAACGGAT TACCAGGGAT TTCAGTCGAT GTACACGTTC GTCACATCTC    780
ATCTACCTCC CGGTTTTAAT GAATACGATT TTGTACCAGA GTCCTTTGAT CGTGACAAAA    840
CAATTGCACT GATAATGAAT TCCTCTGGAT CTACTGGGTT ACCTAAGGGT GTGGCCCTTC    900
CGCATAGAAC TGCCTGCGTC AGATTCTCGC ATGCCAGAGA TCCTATTTTT GGCAATCAAA    960
TCATTCCGGA TACTGCGATT TTAAGTGTTG TTCCATTCCA TCACGGTTTT GGAATGTTTA   1020
CTACACTCGG ATATTTGATA TGTGGATTTC GAGTCGTCTT AATGTATAGA TTTGAAGAAG   1080
AGCTGTTTTT ACGATCCCTT CAGGATTACA AAATTCAAAG TGCGTTGCTA GTACCAACCC   1140
TATTTTCATT CTTCGCCAAA AGCACTCTGA TTGACAAATA CGATTTATCT AATTTACACG   1200
AAATTGCTTC TGGGGGCGCA CCTCTTTCGA AAGAAGTCGG GGAAGCGGTT GCAAAACGCT   1260
TCCATCTTCC AGGGATACGA CAAGGATATG GGCTCACTGA GACTACATCA GCTATTCTGA   1320
TTACACCCGA GGGGGATGAT AAACCGGGCG CGGTCGGTAA AGTTGTTCCA TTTTTTGAAG   1380
CGAAGGTTGT GGATCTGGAT ACCGGGAAAA CGCTGGGCGT TAATCAGAGA GGCGAATTAT   1440
GTGTCAGAGG ACCTATGATT ATGTCCGGTT ATGTAAACAA TCCGGAAGCG ACCAACGCCT   1500
TGATTGACAA GGATGGATGG CTACATTCTG GAGACATAGC TTACTGGGAC GAAGACGAAC   1560
ACTTCTTCAT AGTTGACCGC TTGAAGTCTT TAATTAAATA CAAAGGATAT CAGGTGGCCC   1620
CCGCTGAATT GGAATCGATA TTGTTACAAC ACCCCAACAT CTTCGACGCG GGCGTGGCAG   1680
GTCTTCCCGA CGATGACGCC GGTGAACTTC CCGCCGCCGT TGTTGTTTTG GAGCACGGAA   1740
AGACGATGAC GGAAAAAGAG ATCGTGGATT ACGTCGCCAG TCAAGTAACA ACCGCGAAAA   1800
```

-continued

```
AGTTGCGCGG AGGAGTTGTG TTTGTGGACG AAGTACCGAA AGGTCTTACC GGAAAACTCG   1860
ACGCAAGAAA AATCAGAGAG ATCCTCATAA AGGCCAAGAA GGGCGGAAAG TCCAAATTGT   1920
AAAATGTAAC TGTATTCAGC GATGACGAAA TTCTTAGCTA TTGTAATACT GCGATGAGTG   1980
GCAGGGCGGG GCGTAATTTT TTTAAGGCAG TTATTGGTGC CCTTAAACGC CTGGTGCTAC   2040
GCCTGAATAA GTGATAATAA GCGGATGAAT GGCAGAAATT CGCCGGATCT TTGTGAAGGA   2100
ACCTTACTTC TGTGGTGTGA CATAATTGGA CAAACTACCT ACAGAGATTT AAAGCTCTAA   2160
GGTAAATATA AAATTTTTAA GTGTATAATG TGTTAAACTA CTGATTCTAA TTGTTTGTGT   2220
ATTTTAGATT CCAACCTATG GAACTGATGA ATGGGAGCAG TGGTGGAATG CCTTTAATGA   2280
GGAAAACCTG TTTTGCTCAG AAGAAATGCC ATCTAGTGAT GATGAGGCTA CTGCTGACTC   2340
TCAACATTCT ACTCCTCCAA AAAAGAAGAG AAAGGTAGAA GACCCCAAGG ACTTTCCTTC   2400
AGAATTGCTA AGTTTTTTGA GTCATGCTGT GTTTAGTAAT AGAACTCTTG CTTGCTTTGC   2460
TATTTACACC ACAAAGGAAA AAGCTGCACT GCTATACAAG AAAATTATGG AAAAATATTC   2520
TGTAACCTTT ATAAGTAGGC ATAACAGTTA TAATCATAAC ATACTGTTTT TTCTTACTCC   2580
ACACAGGCAT AGAGTGTCTG CTATTAATAA CTATGCTCAA AAATTGTGTA CCTTTAGCTT   2640
TTTAATTTGT AAAGGGGTTA ATAAGGAATA TTTGATGTAT AGTGCCTTGA CTAGAGATCA   2700
TAATCAGCCA TACCACATTT GTAGAGGTTT TACTTGCTTT AAAAAACCTC CCACACCTCC   2760
CCCTGAACCT GAAACATAAA ATGAATGCAA TTGTTGTTGT TAACTTGTTT ATTGCAGCTT   2820
ATAATGGTTA CAAATAAAGC AATAGCATCA CAAATTTCAC AAATAAAGCA TTTTTTTCAC   2880
TGCATTCTAG TTGTGGTTTG TCCAAACTCA TCAATGTATC TTATCATGTC TGGATCCGTC   2940
GACCGATGCC CTTGAGAGCC TTCAACCCAG TCAGCTCCTT CCGGTGGGCG CGGGGCATGA   3000
CTATCGTCGC CGCACTTATG ACTGTCTTCT TTATCATGCA ACTCGTAGGA CAGGTGCCGG   3060
CAGCGCTCTT CCGCTTCCTC GCTCACTGAC TCGCTGCGCT CGGTCGTTCG GCTGCGGCGA   3120
GCGGTATCAG CTCACTCAAA GGCGGTAATA CGGTTATCCA CAGAATCAGG GGATAACGCA   3180
GGAAAGAACA TGTGAGCAAA AGGCCAGCAA AAGGCCAGGA ACCGTAAAAA GGCCGCGTTG   3240
CTGGCGTTTT TCCATAGGCT CCGCCCCCCT GACGAGCATC ACAAAAATCG ACGCTCAAGT   3300
CAGAGGTGGC GAAACCCGAC AGGACTATAA AGATACCAGG CGTTTCCCCC TGGAAGCTCC   3360
CTCGTGCGCT CTCCTGTTCC GACCCTGCCG CTTACCGGAT ACCTGTCCGC CTTTCTCCCT   3420
TCGGGAAGCG TGGCGCTTTC TCAATGCTCA CGCTGTAGGT ATCTCAGTTC GGTGTAGGTC   3480
GTTCGCTCCA AGCTGGGCTG TGTGCACGAA CCCCCCGTTC AGCCCGACCG CTGCGCCTTA   3540
TCCGGTAACT ATCGTCTTGA GTCCAACCCG GTAAGACACG ACTTATCGCC ACTGGCAGCA   3600
GCCACTGGTA ACAGGATTAG CAGAGCGAGG TATGTAGGCG GTGCTACAGA GTTCTTGAAG   3660
TGGTGGCCTA ACTACGGCTA CACTAGAAGG ACAGTATTTG GTATCTGCGC TCTGCTGAAG   3720
CCAGTTACCT TCGGAAAAAG AGTTGGTAGC TCTTGATCCG GCAAACAAAC CACCGCTGGT   3780
AGCGGTGGTT TTTTTGTTTG CAAGCAGCAG ATTACGCGCA GAAAAAAAGG ATCTCAAGAA   3840
GATCCTTTGA TCTTTTCTAC GGGGTCTGAC GCTCAGTGGA ACGAAAACTC ACGTTAAGGG   3900
ATTTTGGTCA TGAGATTATC AAAAAGGATC TTCACCTAGA TCCTTTTAAA TTAAAAATGA   3960
AGTTTTAAAT CAATCTAAAG TATATATGAG TAAACTTGGT CTGACAGTTA CCAATGCTTA   4020
ATCAGTGAGG CACCTATCTC AGCGATCTGT CTATTTCGTT CATCCATAGT TGCCTGACTC   4080
CCCGTCGTGT AGATAACTAC GATACGGGAG GGCTTACCAT CTGGCCCCAG TGCTGCAATG   4140
```

-continued

```
ATACCGCGAG ACCCACGCTC ACCGGCTCCA GATTTATCAG CAATAAACCA GCCAGCCGGA   4200
AGGGCCGAGC GCAGAAGTGG TCCTGCAACT TTATCCGCCT CCATCCAGTC TATTAATTGT   4260
TGCCGGGAAG CTAGAGTAAG TAGTTCGCCA GTTAATAGTT TGCGCAACGT TGTTGCCATT   4320
GCTACAGGCA TCGTGGTGTC ACGCTCGTCG TTTGGTATGG CTTCATTCAG CTCCGGTTCC   4380
CAACGATCAA GGCGAGTTAC ATGATCCCCC ATGTTGTGCA AAAAAGCGGT TAGCTCCTTC   4440
GGTCCTCCGA TCGTTGTCAG AAGTAAGTTG GCCGCAGTGT TATCACTCAT GGTTATGGCA   4500
GCACTGCATA ATTCTCTTAC TGTCATGCCA TCCGTAAGAT GCTTTTCTGT GACTGGTGAG   4560
TACTCAACCA AGTCATTCTG AGAATAGTGT ATGCGGCGAC CGAGTTGCTC TTGCCCGGCG   4620
TCAATACGGG ATAATACCGC GCCACATAGC AGAACTTTAA AAGTGCTCAT CATTGGAAAA   4680
CGTTCTTCGG GGCGAAAACT CTCAAGGATC TTACCGCTGT TGAGATCCAG TTCGATGTAA   4740
CCCACTCGTG CACCCAACTG ATCTTCAGCA TCTTTTACTT TCACCAGCGT TTCTGGGTGA   4800
GCAAAAACAG GAAGGCAAAA TGCCGCAAAA AAGGGAATAA GGGCGACACG GAAATGTTGA   4860
ATACTCATAC TCTTCCTTTT TCAATATTAT TGAAGCATTT ATCAGGGTTA TTGTCTCATG   4920
AGCGGATACA TATTTGAATG TATTTAGAAA AATAAACAAA TAGGGGTTCC GCGCACATTT   4980
CCCCGAAAAG TGCCACCTGA CGCGCCCTGT AGCGGCGCAT TAAGCGCGGC GGGTGTGGTG   5040
GTTACGCGCA GCGTGACCGC TACACTTGCC AGCGCCCTAG CGCCCGCTCC TTTCGCTTTC   5100
TTCCCTTCCT TTCTCGCCAC GTTCGCCGGC TTTCCCCGTC AAGCTCTAAA TCGGGGGCTC   5160
CCTTTAGGGT TCCGATTTAG TGCTTTACGG CACCTCGACC CCAAAAAACT TGATTAGGGT   5220
GATGGTTCAC GTAGTGGGCC ATCGCCCTGA TAGACGGTTT TTCGCCCTTT GACGTTGGAG   5280
TCCACGTTCT TTAATAGTGG ACTCTTGTTC CAAACTGGAA CAACACTCAA CCCTATCTCG   5340
GTCTATTCTT TTGATTTATA AGGGATTTTG CCGATTTCGG CCTATTGGTT AAAAAATGAG   5400
CTGATTTAAC AAAAATTTAA CGCGAATTTT AACAAAATAT TAACGTTTAC AATTTCCCAT   5460
TCGCCATTCA GGCTGCGCAA CTGTTGGGAA GGGCGATCGG TGCGGGCCTC TTCGCTATTA   5520
CGCCAGCCCA AGCTACCATG ATAAGTAAGT AATATTAAGG TACGTGGAGG TTTTACTTGC   5580
TTTAAAAAAC CTCCCACACC TCCCCCTGAA CCTGAAACAT AAAATGAATG CAATTGTTGT   5640
TGTTAACTTG TTTATTGCAG CTTATAATGG TTACAAATAA AGCAATAGCA TCACAAATTT   5700
CACAAATAAA GCATTTTTTT CACTGCATTC TAGTTGTGGT TTGTCCAAAC TCATCAATGT   5760
ATCTTATGGT ACTGTAACTG AGCTAACATA A                                  5791
```

(2) INFORMATION FOR SEQ ID NO:32:

(i) SEQUENCE CHARACTERISTICS:
(A) LENGTH: 5789 base pairs
(B) TYPE: nucleic acid
(C) STRANDEDNESS: double
(D) TOPOLOGY: circular (xi) SEQUENCE DESCRIPTION: SEQ ID NO:32:

```
CCCGGGAGGT ACCGAGCTCT TACGCGTGCT AGCTCGAGAT CTGCATCTCA ATTAGTCAGC     60
AACCATAGTC CCGCCCCTAA CTCCGCCCAT CCCGCCCCTA ACTCCGCCCA GTTCCGCCCA    120
TTCTCCGCCC CATGGCTGAC TAATTTTTTT TATTTATGCA GAGGCCGAGG CCGCCTCGGC    180
CTCTGAGCTA TTCCAGAAGT AGTGAGGAGG CTTTTTTGGA GGCCTAGGCT TTTGCAAAAA    240
GCTTGGCATT CCGGTACTGT TGGTAAAATG GAAGACGCCA AAAACATAAA GAAAGGCCCG    300
GCGCCATTCT ATCCTCTAGA GGATGGAACC GCTGGAGAGC AACTGCATAA GGCTATGAAG    360
```

-continued

```
AGATACGCCC TGGTTCCTGG AACAATTGCT TTTACAGATG CACATATCGA GGTGAACATC    420
ACGTACGCGG AATACTTCGA AATGTCCGTT CGGTTGGCAG AAGCTATGAA ACGATATGGG    480
CTGAATACAA ATCACAGAAT CGTCGTATGC AGTGAAAACT CTCTTCAATT CTTTATGCCG    540
GTGTTGGGCG CGTTATTTAT CGGAGTTGCA GTTGCGCCCG CGAACGACAT TTATAATGAA    600
CGTGAATTGC TCAACAGTAT GAACATTTCG CAGCCTACCG TAGTGTTTGT TTCCAAAAAG    660
GGGTTGCAAA AAATTTTGAA CGTGCAAAAA AAATTACCAA TAATCCAGAA AATTATTATC    720
ATGGATTCTA AAACGGATTA CCAGGGATTT CAGTCGATGT ACACGTTCGT CACATCTCAT    780
CTACCTCCCG GTTTTAATGA ATACGATTTT GTACCAGAGT CCTTTGATCG TGACAAAACA    840
ATTGCACTGA TAATGAATTC CTCTGGATCT ACTGGGTTAC CTAAGGGTGT GGCCCTTCCG    900
CATAGAACTG CCTGCGTCAG ATTCTCGCAT GCCAGAGATC CTATTTTTGG CAATCAAATC    960
ATTCCGGATA CTGCGATTTT AAGTGTTGTT CCATTCCATC ACGGTTTTGG AATGTTTACT   1020
ACACTCGGAT ATTTGATATG TGGATTTCGA GTCGTCTTAA TGTATAGATT TGAAGAAGAG   1080
CTGTTTTTAC GATCCCTTCA GGATTACAAA ATTCAAAGTG CGTTGCTAGT ACCAACCCTA   1140
TTTTCATTCT TCGCCAAAAG CACTCTGATT GACAAATACG ATTTATCTAA TTTACACGAA   1200
ATTGCTTCTG GGGGCGCACC TCTTTCGAAA GAAGTCGGGG AAGCGGTTGC AAAACGCTTC   1260
CATCTTCCAG GGATACGACA AGGATATGGG CTCACTGAGA CTACATCAGC TATTCTGATT   1320
ACACCCGAGG GGGATGATAA ACCGGGCGCG GTCGGTAAAG TTGTTCCATT TTTTGAAGCG   1380
AAGGTTGTGG ATCTGGATAC CGGGAAAACG CTGGGCGTTA ATCAGAGAGG CGAATTATGT   1440
GTCAGAGGAC CTATGATTAT GTCCGGTTAT GTAAACAATC CGGAAGCGAC CAACGCCTTG   1500
ATTGACAAGG ATGGATGGCT ACATTCTGGA GACATAGCTT ACTGGGACGA AGACGAACAC   1560
TTCTTCATAG TTGACCGCTT GAAGTCTTTA ATTAAATACA AAGGATATCA GGTGGCCCCC   1620
GCTGAATTGG AATCGATATT GTTACAACAC CCCAACATCT TCGACGCGGG CGTGGCAGGT   1680
CTTCCCGACG ATGACGCCGG TGAACTTCCC GCCGCCGTTG TTGTTTTGGA GCACGGAAAG   1740
ACGATGACGG AAAAAGAGAT CGTGGATTAC GTCGCCAGTC AAGTAACAAC CGCGAAAAAG   1800
TTGCGCGGAG GAGTTGTGTT TGTGGACGAA GTACCGAAAG GTCTTACCGG AAAACTCGAC   1860
GCAAGAAAAA TCAGAGAGAT CCTCATAAAG GCCAAGAAGG GCGGAAAGTC CAAATTGTAA   1920
AATGTAACTG TATTCAGCGA TGACGAAATT CTTAGCTATT GTAATACTGC GATGAGTGGC   1980
AGGGCGGGGC GTAATTTTTT TAAGGCAGTT ATTGGTGCCC TTAAACGCCT GGTGCTACGC   2040
CTGAATAAGT GATAATAAGC GGATGAATGG CAGAAATTCG CCGGATCTTT GTGAAGGAAC   2100
CTTACTTCTG TGGTGTGACA TAATTGGACA AACTACCTAC AGAGATTTAA AGCTCTAAGG   2160
TAAATATAAA ATTTTTAAGT GTATAATGTG TTAAACTACT GATTCTAATT GTTTGTGTAT   2220
TTTAGATTCC AACCTATGGA ACTGATGAAT GGGAGCAGTG GTGGAATGCC TTTAATGAGG   2280
AAAACCTGTT TTGCTCAGAA GAAATGCCAT CTAGTGATGA TGAGGCTACT GCTGACTCTC   2340
AACATTCTAC TCCTCCAAAA AAGAAGAGAA AGGTAGAAGA CCCCAAGGAC TTTCCTTCAG   2400
AATTGCTAAG TTTTTTGAGT CATGCTGTGT TTAGTAATAG AACTCTTGCT TGCTTTGCTA   2460
TTTACACCAC AAAGGAAAAA GCTGCACTGC TATACAAGAA AATTATGGAA AAATATTCTG   2520
TAACCTTTAT AAGTAGGCAT AACAGTTATA ATCATAACAT ACTGTTTTTT CTTACTCCAC   2580
ACAGGCATAG AGTGTCTGCT ATTAATAACT ATGCTCAAAA ATTGTGTACC TTTAGCTTTT   2640
TAATTTGTAA AGGGGTTAAT AAGGAATATT TGATGTATAG TGCCTTGACT AGAGATCATA   2700
ATCAGCCATA CCACATTTGT AGAGGTTTTA CTTGCTTTAA AAAACCTCCC ACACCTCCCC   2760
```

-continued

```
CTGAACCTGA AACATAAAAT GAATGCAATT GTTGTTGTTA ACTTGTTTAT TGCAGCTTAT   2820
AATGGTTACA AATAAAGCAA TAGCATCACA AATTTCACAA ATAAAGCATT TTTTTCACTG   2880
CATTCTAGTT GTGGTTTGTC CAAACTCATC AATGTATCTT ATCATGTCTG GATCCGTCGA   2940
CCGATGCCCT TGAGAGCCTT CAACCCAGTC AGCTCCTTCC GGTGGGCGCG GGGCATGACT   3000
ATCGTCGCCG CACTTATGAC TGTCTTCTTT ATCATGCAAC TCGTAGGACA GGTGCCGGCA   3060
GCGCTCTTCC GCTTCCTCGC TCACTGACTC GCTGCGCTCG GTCGTTCGGC TGCGGCGAGC   3120
GGTATCAGCT CACTCAAAGG CGGTAATACG GTTATCCACA GAATCAGGGG ATAACGCAGG   3180
AAAGAACATG TGAGCAAAAG GCCAGCAAAA GGCCAGGAAC CGTAAAAAGG CCGCGTTGCT   3240
GGCGTTTTTC CATAGGCTCC GCCCCCCTGA CGAGCATCAC AAAAATCGAC GCTCAAGTCA   3300
GAGGTGGCGA AACCCGACAG GACTATAAAG ATACCAGGCG TTTCCCCCTG GAAGCTCCCT   3360
CGTGCGCTCT CCTGTTCCGA CCCTGCCGCT TACCGGATAC CTGTCCGCCT TTCTCCCTTC   3420
GGGAAGCGTG GCGCTTTCTC AATGCTCACG CTGTAGGTAT CTCAGTTCGG TGTAGGTCGT   3480
TCGCTCCAAG CTGGGCTGTG TGCACGAACC CCCCGTTCAG CCCGACCGCT GCGCCTTATC   3540
CGGTAACTAT CGTCTTGAGT CCAACCCGGT AAGACACGAC TTATCGCCAC TGGCAGCAGC   3600
CACTGGTAAC AGGATTAGCA GAGCGAGGTA TGTAGGCGGT GCTACAGAGT TCTTGAAGTG   3660
GTGGCCTAAC TACGGCTACA CTAGAAGGAC AGTATTTGGT ATCTGCGCTC TGCTGAAGCC   3720
AGTTACCTTC GGAAAAAGAG TTGGTAGCTC TTGATCCGGC AAACAAACCA CCGCTGGTAG   3780
CGGTGGTTTT TTTGTTTGCA AGCAGCAGAT TACGCGCAGA AAAAAAGGAT CTCAAGAAGA   3840
TCCTTTGATC TTTTCTACGG GGTCTGACGC TCAGTGGAAC GAAAACTCAC GTTAAGGGAT   3900
TTTGGTCATG AGATTATCAA AAAGGATCTT CACCTAGATC CTTTTAAATT AAAAATGAAG   3960
TTTTAAATCA ATCTAAAGTA TATATGAGTA AACTTGGTCT GACAGTTACC AATGCTTAAT   4020
CAGTGAGGCA CCTATCTCAG CGATCTGTCT ATTTCGTTCA TCCATAGTTG CCTGACTCCC   4080
CGTCGTGTAG ATAACTACGA TACGGGAGGG CTTACCATCT GGCCCCAGTG CTGCAATGAT   4140
ACCGCGAGAC CCACGCTCAC CGGCTCCAGA TTTATCAGCA ATAAACCAGC CAGCCGGAAG   4200
GGCCGAGCGC AGAAGTGGTC CTGCAACTTT ATCCGCCTCC ATCCAGTCTA TTAATTGTTG   4260
CCGGGAAGCT AGAGTAAGTA GTTCGCCAGT TAATAGTTTG CGCAACGTTG TTGCCATTGC   4320
TACAGGCATC GTGGTGTCAC GCTCGTCGTT TGGTATGGCT TCATTCAGCT CCGGTTCCCA   4380
ACGATCAAGG CGAGTTACAT GATCCCCCAT GTTGTGCAAA AAGCGGTTA GCTCCTTCGG   4440
TCCTCCGATC GTTGTCAGAA GTAAGTTGGC CGCAGTGTTA TCACTCATGG TTATGGCAGC   4500
ACTGCATAAT TCTCTTACTG TCATGCCATC CGTAAGATGC TTTTCTGTGA CTGGTGAGTA   4560
CTCAACCAAG TCATTCTGAG AATAGTGTAT GCGGCGACCG AGTTGCTCTT GCCCGGCGTC   4620
AATACGGGAT AATACCGCGC CACATAGCAG AACTTTAAAA GTGCTCATCA TTGGAAAACG   4680
TTCTTCGGGG CGAAAACTCT CAAGGATCTT ACCGCTGTTG AGATCCAGTT CGATGTAACC   4740
CACTCGTGCA CCCAACTGAT CTTCAGCATC TTTTACTTTC ACCAGCGTTT CTGGGTGAGC   4800
AAAAACAGGA AGGCAAAATG CCGCAAAAAA GGGAATAAGG GCGACACGGA AATGTTGAAT   4860
ACTCATACTC TTCCTTTTTC AATATTATTG AAGCATTTAT CAGGGTTATT GTCTCATGAG   4920
CGGATACATA TTTGAATGTA TTTAGAAAAA TAAACAAATA GGGGTTCCGC GCACATTTCC   4980
CCGAAAAGTG CCACCTGACG CGCCCTGTAG CGGCGCATTA AGCGCGGCGG GTGTGGTGGT   5040
TACGCGCAGC GTGACCGCTA CACTTGCCAG CGCCCTAGCG CCCGCTCCTT TCGCTTTCTT   5100
```

-continued

CCCTTCCTTT CTCGCCACGT TCGCCGGCTT TCCCCGTCAA GCTCTAAATC GGGGGCTCCC 5160

TTTAGGGTTC CGATTTAGTG CTTTACGGCA CCTCGACCCC AAAAAACTTG ATTAGGGTGA 5220

TGGTTCACGT AGTGGGCCAT CGCCCTGATA GACGGTTTTT CGCCCTTTGA CGTTGGAGTC 5280

CACGTTCTTT AATAGTGGAC TCTTGTTCCA AACTGGAACA ACACTCAACC CTATCTCGGT 5340

CTATTCTTTT GATTTATAAG GGATTTTGCC GATTTCGGCC TATTGGTTAA AAAATGAGCT 5400

GATTTAACAA AAATTTAACG CGAATTTTAA CAAAATATTA ACGTTTACAA TTTCCCATTC 5460

GCCATTCAGG CTGCGCAACT GTTGGGAAGG GCGATCGGTG CGGGCCTCTT CGCTATTACG 5520

CCAGCCCAAG CTACCATGAT AAGTAAGTAA TATTAAGGTA CGTGGAGGTT TTACTTGCTT 5580

TAAAAAACCT CCCACACCTC CCCCTGAACC TGAAACATAA AATGAATGCA ATTGTTGTTG 5640

TTAACTTGTT TATTGCAGCT TATAATGGTT ACAAATAAAG CAATAGCATC ACAAATTTCA 5700

CAAATAAAGC ATTTTTTTCA CTGCATTCTA GTTGTGGTTT GTCCAAACTC ATCAATGTAT 5760

CTTATGGTAC TGTAACTGAG CTAACATAA 5789

(2) INFORMATION FOR SEQ ID NO:33:

(i) SEQUENCE CHARACTERISTICS:
(A) LENGTH: 11 base pairs
(B) TYPE: nucleic acid
(C) STRANDEDNESS: single
(D) TOPOLOGY: linear (xi) SEQUENCE DESCRIPTION: SEQ ID NO:33:

RGTGACNNNG C 11

(2) INFORMATION FOR SEQ ID NO:34:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:34:

CAGCCCCAGG GACAGAGCTG 20

(2) INFORMATION FOR SEQ ID NO:35:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:35:

CAGCCCCATT TGAGTGTATG 20

(2) INFORMATION FOR SEQ ID NO:36:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:36:

CTAATGGTGA CAAAGCAG 18

(2) INFORMATION FOR SEQ ID NO:37:

-continued (i) SEQUENCE CHARACTERISTICS:
(A) LENGTH: 16 base pairs
(B) TYPE: nucleic acid
(C) STRANDEDNESS: single
(D) TOPOLOGY: linear (xi) SEQUENCE DESCRIPTION: SEQ ID NO:37:

AGTGCTGTCA CGCTAG 16

(2) INFORMATION FOR SEQ ID NO:38:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO:38:

TGTATCTTAT GGTACTGTAA CTG 23

(2) INFORMATION FOR SEQ ID NO:39:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO:39:

GATCATACAC TCAAATGGGG CTGGG 25

(2) INFORMATION FOR SEQ ID NO:40:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:40:

CCCATTTGAG TGTATGATCC TTGAAC 26

(2) INFORMATION FOR SEQ ID NO:41:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:41:

GGCGTCTTCC ATTTTACC 18

(2) INFORMATION FOR SEQ ID NO:42:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:42:

CAGCCCCCTT TGAGTGTATG 20

(2) INFORMATION FOR SEQ ID NO:43:

(i) SEQUENCE CHARACTERISTICS:

-continued (A) LENGTH: 32 base pairs
(B) TYPE: nucleic acid
(C) STRANDEDNESS: single
(D) TOPOLOGY: linear (xi) SEQUENCE DESCRIPTION: SEQ ID NO:43:

GCAGTCACAG TGACTCAGCA GAATCTGAGC CT 32

(2) INFORMATION FOR SEQ ID NO:44:

(i) SEQUENCE CHARACTERISTICS:
(A) LENGTH: 32 base pairs
(B) TYPE: nucleic acid
(C) STRANDEDNESS: single
(D) TOPOLOGY: linear (xi) SEQUENCE DESCRIPTION: SEQ ID NO:44:

AGAGTCACAG TGACTTGGCA AAATCTGAGC CG 32

(2) INFORMATION FOR SEQ ID NO:45:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:45:

TGGCATTGCT AATGGTGACA AAGCAACTTT 30

(2) INFORMATION FOR SEQ ID NO:46:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:46:

TGACATTGCT AATGGTGACA AAGCAACTTT 30

(2) INFORMATION FOR SEQ ID NO:47:

(i) SEQUENCE CHARACTERISTICS:
(A) LENGTH: 37 base pairs
(B) TYPE: nucleic acid
(C) STRANDEDNESS: single
(D) TOPOLOGY: linear (xi) SEQUENCE DESCRIPTION: SEQ ID NO:47:

TGCCCAGCCC CAGGGACAGA GCTGATCCTT GAACTCT 37

(2) INFORMATION FOR SEQ ID NO:48:

(i) SEQUENCE CHARACTERISTICS:
(A) LENGTH: 37 base pairs
(B) TYPE: nucleic acid
(C) STRANDEDNESS: single
(D) TOPOLOGY: linear (xi) SEQUENCE DESCRIPTION: SEQ ID NO:48:

TGCCCAGCCC CAAGGACAGA GCTGATCCTT GAACTCT 37

(2) INFORMATION FOR SEQ ID NO:49:

(i) SEQUENCE CHARACTERISTICS:
(A) LENGTH: 37 base pairs

-continued

```
        (B) TYPE: nucleic acid
        (C) STRANDEDNESS: single
        (D) TOPOLOGY: linear

   (xi) SEQUENCE DESCRIPTION: SEQ ID NO:49:

TGCCCGGCCC CAGGGACAAA GCTGATCCTT GAACTCT                         37


(2) INFORMATION FOR SEQ ID NO:50:

     (i) SEQUENCE CHARACTERISTICS:
        (A) LENGTH: 37 base pairs
        (B) TYPE: nucleic acid
        (C) STRANDEDNESS: single
        (D) TOPOLOGY: linear

   (xi) SEQUENCE DESCRIPTION: SEQ ID NO:50:

TGCCTAGCCT CGGGAACAGA GCTGATCCTT GAACTCT                         37


(2) INFORMATION FOR SEQ ID NO:51:

     (i) SEQUENCE CHARACTERISTICS:
        (A) LENGTH: 37 base pairs
        (B) TYPE: nucleic acid
        (C) STRANDEDNESS: single
        (D) TOPOLOGY: linear

   (xi) SEQUENCE DESCRIPTION: SEQ ID NO:51:

TGCCCAGCCT CAGGAACAGA GCTGATCCTT GAACTCT                         37
```